(12) United States Patent
Boger

(10) Patent No.: US 6,653,087 B1
(45) Date of Patent: Nov. 25, 2003

(54) CONVERGENT SYNTHESIS OF COMBINATORIAL LIBRARY

(75) Inventor: Dale L. Boger, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/367,199

(22) PCT Filed: Feb. 6, 1998

(86) PCT No.: PCT/US98/02351

§ 371 (c)(1),
(2), (4) Date: Aug. 9, 1999

(87) PCT Pub. No.: WO98/35231

PCT Pub. Date: Aug. 13, 1998

Related U.S. Application Data

(60) Provisional application No. 60/037,867, filed on Feb. 7, 1997.

(51) Int. Cl.$^7$ ............................................. G01N 33/53
(52) U.S. Cl. ..................... 435/7.1; 436/501; 436/518; 564/133; 564/488
(58) Field of Search ................ 430/264; 435/69.1, 435/7.1, 174; 436/518, 501; 530/402; 564/133, 488

(56) References Cited

U.S. PATENT DOCUMENTS 5,770,344 A * 6/1998 Yamada et al. ............. 430/264

OTHER PUBLICATIONS

Carell et al. 1994. A novel procedure for the synthesis of libraries containing small organic molecules. Angew. Chem. Ed. Engl. 33:2059–2061. 1994.*
Boger, et al., "Generalized Dipeptidomimetic Template: Solution Phase Parallel Synthesis of Combinatorial Libraries", *J. Am. Chem. Soc.* 118:2109–2110 (1996).
Cheng, et al., "Novel Solution Phase Strategy for the Synthesis of Chemical Libraries Containing Small Organic Molecules", *J. Am. Chem. Soc.* 118:2567–2573 (1996).
Keating, et al., "Postcondensation Modifications of Ugi Four–Component Condensation Products: 1–Isocyanocyclohexene as a Convertible Isocyanide. Mechanism of Conversion, Synthesis of Diverse Structures, and Demonstration of Resin Capture", *J. Am. Chem. Soc.* 118:2574–2583 (1996).
Shipps, Jr., et al., "Solution–Phase Generation of Tetraurea Libraries", *Bioorg. Med. Chem.* 4:655–657 (1996).
Cheng, et al., "A Solution–Phase Strategy for the Synthesis of Chemical Libraries Containing Small Organic Molecules: A Universal and Dipeptide Mimetic Template", *Bioorg. Med. Chem.* 4: 727–737 (1996).
Konings, et al., "Strategies for Rapid Deconvolution of Combinatorial Libraries: Comparative Evaluation Using a Model System", *J. Med. Chem.* 40: 4386–4395 (1997).
Ugi, et al., "Multicomponent Reactions in Organic Chemistry", *Endeavour* 18: 115–122 (1994).
Carell, et al., "A Novel Procedure for the Synthesis of Libraries Containing Small Organic Molecules", *Angew. Chem. Int. Ed. Engl.* 33: 2059–2061 (1994).
Smith, et al., "Synthesis and Biological Evaluation of a Library Containing Potentially 1600 Amides/Esters. A Strategy for Rapid Compound Generation and Screening.", *Bioorg. Med. Chem. Lett.* 4: 2821–2824 (1994).
Freier, et al., "Deconvolution of Combinatorial Libraries for Drug Discovery: A Model System", *J. Med. Chem.* 38: 344–352 (1995).
Pirrung, et al., "Preparation and Screening against Acetylcholinesterase of a Non–Peptide "Indexed" Combinatorial Library", *J. Am. Chem. Soc.* 117: 1240–1245 (1995).
Carell, et al., "New Promise in Combinatorial Chemistry: Synthesis, Characterization, and Screening of Small–Molecule Libraries in Solution", *Chem. Biol.* 2: 171–183 (1995).
Han, et al., "Liquid–Phase Combinatorial Synthesis", *Proc. Natl. Acad. Sci. USA* 92: 6419–6423 (1995).
Pirrung, et al., "Discovery of a Novel Tetrahydroacridine Acetylcholinesterase Inhibitor Through an Indexed Combinatorial Library", *Chem. Biol.* 2: 621–626 (1995).
Dunayevskiy, et al., "Characterization of the Complexity of Small–Molecule Libraries by Electrospray Ionization Mass Spectroscopy", *Anal. Chem.* 67: 2906–2915 (1995).
Früchtel, et al., "Organic Chemistry on Solid Supports", *Angew. Chem. Int. Ed. Engl.* 35: 17–42 (1996).
Armstrong, et al., "Multiple–Component Condensation Strategies for Combinatorial Library Synthesis", *Acc. Chem. Res* 29: 123–131 (1996).

* cited by examiner

*Primary Examiner*—Bennett Celsa
*Assistant Examiner*—Jon D. Epperson
(74) *Attorney, Agent, or Firm*—Donald G. Lewis

(57) ABSTRACT

Targeted C2-symmetric and unsymmetric chemical libraries for use in protein and receptor homodimerization and heterodimerization are constructed by solution phase methodologies. Exemplary libraries are prepared in a 60 to 10 sub-library format by symmetrical coupling of the constructed fragments with a mixture of tethering dicarboxylic acids. In each step of the 3-step reaction sequence, the reactants, unreacted starting material, reagents and their byproducts were removed by simple liquid-liquid or liquid-solid extractions providing the desired intermediates and final libraries in multi-milligram quantities in high purities ($\geq$90–100%) independent of the reaction yields and without deliberate reaction optimization. The synthesis of a second prototypical library employed the olefin metathesis reaction to join and combinatorially randomize the length of linker tether. This approach provides a unique opportunity to rapidly generate a statistically controlled mixture of homo and heterodimers of remarkable diversity.

2 Claims, 25 Drawing Sheets

| Entry | A1 | A2 | A3 | A4 | A5 | A6 |
|---|---|---|---|---|---|---|
| B1 | 49 mg, 99% | 49 mg, 99% | 48 mg, 99% | 49 mg, 99% | 50 mg, 99% | 36 mg, 74% |
| B2 | 10 mg, 24% | 13 mg, 29% | 37 mg, 84% | 10 mg, 21% | 14 mg, 32% | 6 mg, 13% |
| B3 | 36 mg, 79% | 46 mg, 93% | 20 mg, 41% | 4 mg, 9% | 26 mg, 56% | 38 mg, 59% |
| B4 | 36 mg, 74% | 39 mg, 76% | 22 mg, 46% | 37 mg, 73% | 28 mg, 57% | 36 mg, 73% |
| B5 | 47 mg, 99% | 50 mg, 99% | 49 mg, 99% | 50 mg, 99% | 31 mg, 59% | 42 mg, 82% |
| B6 | 18 mg, 44% | 58 mg, 66% | 9 mg, 21% | 22 mg, 50% | 12 mg, 27% | 29 mg, 66% |
| B7 | 11 mg, 29% | 28 mg, 66% | 18 mg, 46% | 21 mg, 50% | 11 mg, 26% | 14 mg, 34% |
| B8 | 7 mg, 13% | 26 mg, 47% | 21 mg, 40% | 22 mg, 39% | 18 mg, 33% | 20 mg, 37% |
| B9 | 20 mg, 42% | 10 mg, 20% | 10 mg, 20% | 19 mg, 38% | 18 mg, 37% | 52 mg, 88% |
| B10 | 52 mg, 91% | 48 mg, 78% | 27 mg, 45% | 33 mg, 53% | 40 mg, 68% | 21 mg, 41% |

[a]Yield based on average molecular weight.

FIG. 7

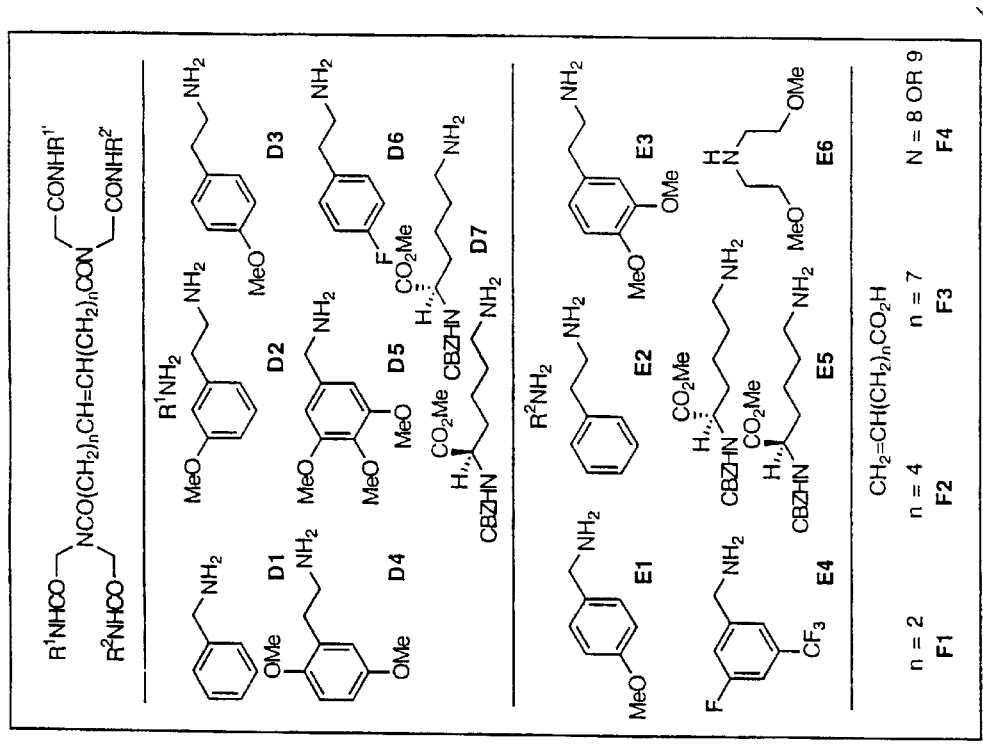
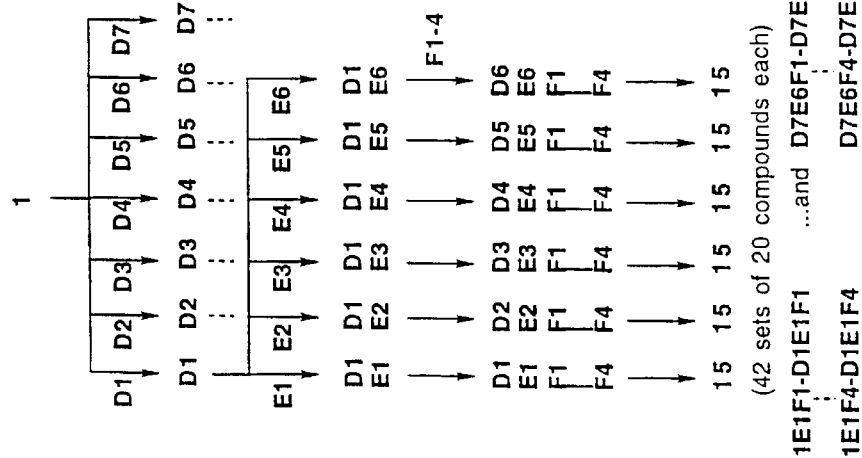
FIG. 11

| 2 | D1 | D2 | D3 | D4 | D5 | D6 |
|---|----|----|----|----|----|----|
|   | 93 | 91 | 89 | 88 | 76 | 100 |

| 3 | D1 | D2 | D3 | D4 | D5 | D6 |
|---|----|----|----|----|----|----|
| E1 | 99 |   |   |   |   |   |
| E2 |   | 75 |   |   |   |   |
| E3 |   |   | 82 |   |   |   |
| E4 |   |   |   | 87 |   |   |
| E5 |   |   |   |   | 11 |   |
| E6 |   |   |   |   |   | 55 |

| 14 | D1E1F1-4 | D2E2F1-4 | D3E3F1-4 |
|----|----------|----------|----------|
|    | 61       | 41       | 53       |
|    | D4E4F1-4 | D5E5F1-4 | D6E6F1-4 |
|    | 52       | 25       | 68       |

FIG. 13

|           | D1 E1 F1-F4 | D2 E2 F1-F4 | D3 E3 F1-F4 | D4 E4 F1-F4 | D5 E5 F1-F4 | D6 E6 F1-F4 |
|-----------|-------------|-------------|-------------|-------------|-------------|-------------|
| D1E1F1-F4 | 67 | 75 | 65 | 51 | 72 | 72 |
| D2E2F1-F4 | 75 | 64 | 68 | 37 | 71 | 57 |
| D3E3F1-F4 | 65 | 68 | 42 | 62 | 45 | 68 |
| D4E4F1-F4 | 51 | 37 | 62 | 42 | 49 | 47 |
| D5E5F1-F4 | 72 | 71 | 45 | 49 | 51 | 45 |
| D6E6F1-F4 | 72 | 57 | 68 | 47 | 45 | 55 |

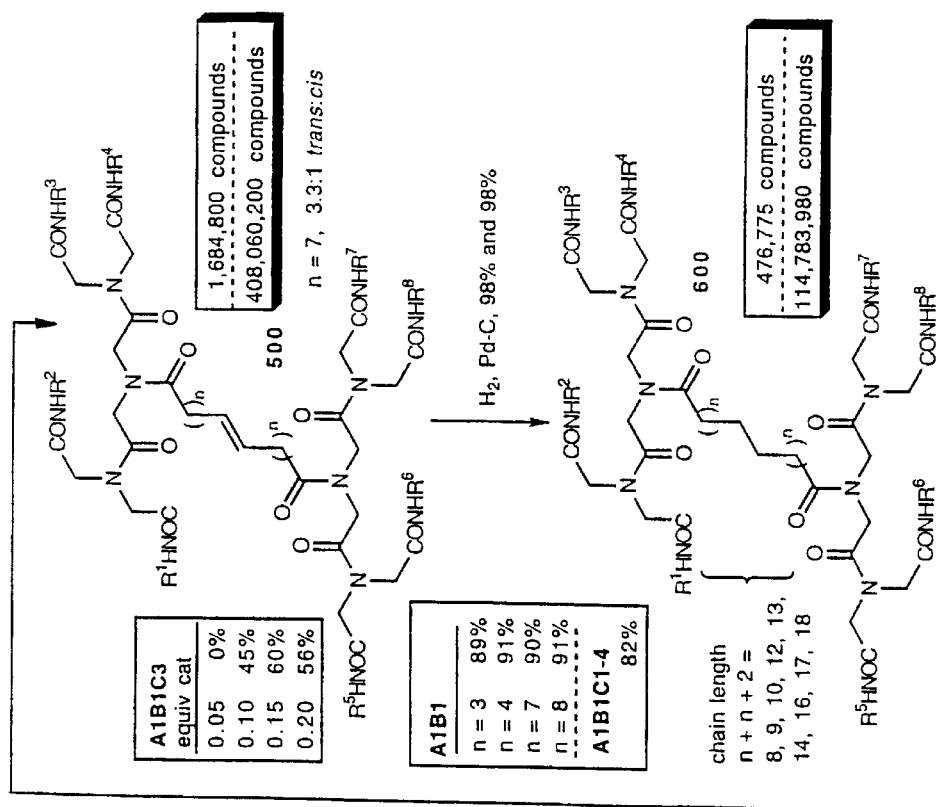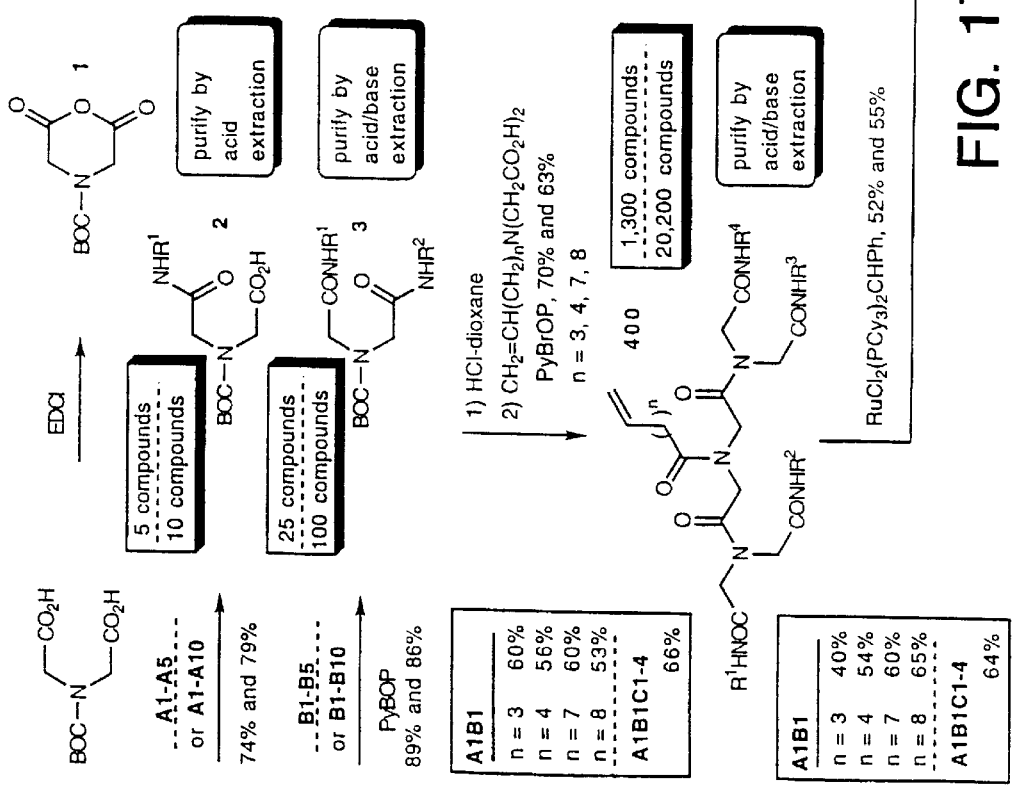
FIG. 17

| Family | Examples | Activation Characteristics |
|---|---|---|
| GH receptor | GHR, EPOR, PRLR, G-CSFR | homodimers |
| IL-3 receptor | IL-3R, GM-CSFR, IL-5R | heterodimeration with $\beta_c$ |
| IL-6 receptor | IL-6R, LIFR, CNTFR, IL-11R | heterodimerization with gp130 |
| IL-2 receptor | IL-2Rα, IL-2Rβ, IL-4R, IL-7R | heterodimerization with IL-2Rγ |

Protein-tyrosine kinase receptors activated by dimerization or oligomerization

| Family | Examples |
|---|---|
| PDGF receptor | PDGFR-α, PDGFR-β, SCFR, CSF-R, Fik-2 |
| EGF receptor | EGFR (erbB), erbB-2 (Neu), erbB-3, erbB-4 |
| FGF receptor | FGFR-1, FGFR-2, FGFR-3, FGFR-4 |
| IGF receptor | Insulin R, IGF-1R |
| HGF receptor | HGFR (Met), MSPR (Ron) |
| VEGF receptor | Flt-1, Flt-2 (KDR) |
| Neurotrophin receptor | Trk, TrkB, TrkC |
| Eph receptor | Eph, Elk, Eck, Cck5, Sek, Eck, Erk |

FIG. 20

| Cytokine | Agonist | Antagonist |
|---|---|---|
| EPO | anemias, selective blood donation | cancer, leukemia |
| TPO | thrombocytopenia | |
| IL-2 | cancer | histoincompatability |
| IL-3 | leukopenia, myeloid reconstitution | leukemia |
| IL-4 | inflammation, cancer | allergy |
| IL-6 | thrombocytopenia | cancer, osteoporosis, inflammation |
| IL-11 | thrombocytopenia | |
| IL-12 | cancer, infections | histoincompatability, autoimmunity |
| G-CSF | neutropenia, myeloid reconstitution | leukemia |
| GM-CSF | leukopenia, myeloid reconstitution | leukemia |
| IFN α/β | cancer, viral infections, autoimmunity | inflammation |
| IFN γ | chronic granulonatous disease, infections | inflammation, autoimmunity |

FIG. 21

| 15 | D1 | D2 | D3 | D4 | D5 | D6 | D7 |
|---|---|---|---|---|---|---|---|
| E1 | 43 | 57 | 53 | 46 | 28 | 65 | 40 |
| E2 | 55 | 53 | 41 | 51 | 58 | 57 | 58 |
| E3 | 51 | 28 | 22 | 61 | 35 | 47 | 32 |
| E4 | 30 | 67 | 42 | 47 | 53 | 58 | 15 |
| E5 | 46 | 20 | 20 | 52 | 45 | 65 | 64 |
| E6 | 40 | 48 | 45 | 24 | 36 | 51 | 45 |

D1-7E1-6F1-4   53%   (28,392 compounds)

| 2 | D1 | D2 | D3 | D4 | D5 | D6 | D7 |
|---|---|---|---|---|---|---|---|
|   | 93 | 91 | 99 | 88 | 76 | 100 | 82 |

| 3, 14 | D1 | D2 | D3 | D4 | D5 | D6 | D7 |
|---|---|---|---|---|---|---|---|
| E1 | 99, 53 | 83, 42 | 100, 87 | 100, 43 | 100, 43 | 92, 39 | 83, 80 |
| E2 | 92, 63 | 99, 68 | 94, 46 | 92, 95 | 95, 46 | 99, 42 | 94, 89 |
| E3 | 95, 66 | 85, 50 | 94, 41 | 92, 86 | 84, 65 | 100, 45 | 86, 82 |
| E4 | 97, 83 | 100, 87 | 100, 75 | 95, 59 | 100, 66 | 100, 46 | 95, 99 |
| E5 | 45, 44 | 45, 52 | 94, 56 | 100, 96 | 90, 61 | 100, 46 | 84, 80 |
| E6 | 72, 88 | 70, 69 | 100, 69 | 88, 83 | 42, 66 | 89, 47 | 73, 70 |

| 2 | A1 | A2 | A3 |
|---|---|---|---|
|  | 100 | 99 | 82 |
| 3, 700, 800, 900 |  | A2 | A3 |
| B1 | 70, 95, 96, 53 | 86, 57, 98, 66 | 61, 94, 83, 49 |
| B2 | 73, 96, 83, 45 | 77, 100, 81, 54 | 61, 84, 82, 51 |
| B3 | 68, 82, 80, 59 | 83, 100, 68, 57 | 61, 91, 87, 67 |
| B4 | 65, 93, 90, 47 | 87, 100, 87, 65 | 55, 87, 81, 38 |
| B5 | 58, 80, 81, 46 | 72, 100, 88, 46 | 57, 51, 83, 67 |
| B6 | 67, 59, 90, 58 | −a | 66, 93, 99, 63 |
| B7 | 59, 90, 93, 62 | 74, 89, 95, 38 | 59, 73, 76, 67 |
| B8 | 64, 80, 87, 57 | 74, 91, 96, 66 | 63, 96, 89, 64 |
| B9 | 53, 70, 93, 57 | 71, 31, 94, 45 | 53, 65, 89, 30 |
| B10 | 58, 68, 92, 42 | 75, 100, 96, 43 | 69, 100, 93, 36 |
| B11 | −a | −a | 58, 71, 96, 30 |
| B12 | 75, 53, 80, 44 | 64, 77, 91, 44 | 50, 48, 62, 54 |
| B13 | 93, 69, 89, 68 | 93, 69, 97, 51 | 86, 92, 97, 30 |
| B14 | 63, 96, 80, 41 | 74, 75, 60, 78 | 75, 68, 95, 53 |
| B15 | 87, 100, 100, 37 | 91, 78, 87, 34 | 86, 99, 89, 57 |
| A1-3B1-15C1-4 | 44% | (28,392 compounds) | | aPrepared as A1B3, A3B3, or A3B6

FIG. 25

CONVERGENT SYNTHESIS OF COMBINATORIAL LIBRARY

This application is a 371 of PCT/US98/02351 filed on Feb. 6, 1998, which claims benefit of U.S. Provisional Patent Application Ser. No: 60/037,867 filed Feb. 7, 1997.

FIELD OF THE INVENTION

The invention is directed to novel C2-symmetrical and unsymmetrical chemical libraries for use in protein and receptor homodimerization and heterodimerization studies by solution phase methods. The invention further relates to novel combinatorial methods for synthesizing such libraries of compounds.

BACKGROUND

Ligand-induced receptor and protein dimerization or oligomerization has emerged as a general mechanism for signal transduction. Members of several receptor families of significance for drug discovery have been established to utilize this mode of receptor activation. These include protein tyrosine kinase receptors (homo- or heterodimerization), cytokine receptors (homo- or heterodimerization), serine/threonine kinase receptors (hetero-oligomerization) and members of the TNF-receptor family (trimerization). Within the cytokine receptor superfamily, the best studied examples are the human growth hormone (hGHr), prolactin (PRLr) and erythropoietin (EPOr) receptors, which form homodimers upon binding with their endogenous ligands. Similarly, intracellular signal transduction often proceeds by ligand-induced protein-protein homo- or heterodimerization.

The fact that the certain receptors and proteins appear to bind their ligands utilizing small clusters of residues for the majority of the binding interaction has led to the expectation that small molecules may be capable of triggering a receptor response. It has been anticipated that the generation of detailed knowledge concerning the dimerization modes and ligand binding domains of single transmembrane domain receptors will provide a basis for the design of functional agonists as well as ligand antagonists. However, the non-contiguous and multiple binding domains involved in both the protein-protein and ligand-protein interactions make it difficult to assess the dimerization mode or ligand binding domains in the absence of three-dimensional structural information. This is especially true considering the size of the typical endogenous ligands including proteins such as EPO (166 residues) which themselves contain noncontiguous binding domains which interact with both subunits of the dimerized receptor. Consequently, the search for non-protein ligands has been addressed through the use of random screening procedures.

Recently, the successful identification of cyclic polypeptides with the capacity to mimic the action of EPO was reported, together with details of the intricate receptor-ligand and receptor-receptor interactions in the bound complex (Wrighton et al. Science 1996, 273, 458; Livnah et al. Science 1996, 273, 464) Although these results represent a major achievement, the size (2 to 20 residues) and nature of ligands identified would not seem to be immediately applicable as drug candidates.

Combinatorial chemistry, introduced for polypeptide and oligonucleotide libraries, has undergone a rapid development and acceptance. It is widely recognized that this approach, when applied to generating non-peptide small molecule diversity, has provided a new paradigm for drug discovery. Perhaps as a consequence of the extension of the concept from peptide and oligonucleotide synthesis, the majority of applications have relied on solid-phase synthesis and methodological advances continue to extend common synthetic transformations to polymer-supported versions (Thompson et al. J. A. Chem. Rev. 1996, 96, 555; Früchtel et al. Angew. Chem., Int. Ed. Engl. 1996, 35, 17; Hermkens et al. Tetrahedron 1996, 52, 4527)

A less well accepted complement to adapting solution-phase chemistry to polymer-supported combinatorial synthesis is the development of protocols for solution-phase combinatorial synthesis (Han et al. Proc. Natl. Acad. Sci. U.S.A. 1995, 92, 6419) Preceding the disclosure of our own efforts on the development of a multi-step solution-phase parallel synthesis of chemical libraries (Cheng et al. J. Am. Chem. Soc. 1996, 118, 2567; Boger et al. J. Am. Chem. Soc. 1996, 118, 2109; Cheng et al. Bioorg. Med. Chem. 1996, 4, 727), the single-step solution-phase synthesis of combinatorial libraries was detailed by at least three groups as follows. Smith and coworkers (Smith et al. Bioorg. Med. Chem. Lett. 1994, 4, 2821), prepared a library of potentially 1600 amides by reacting 40 acid chlorides with 40 nucleophiles. The library was screened as 80 sample mixtures in a matrix format, allowing immediate deconvolution.

A similar sub-library format was used by Pirrung and Chen (Pirrung et al. J. Am. Chem. Soc. 1995, 117, 1240; Pirrung et al. Chem. Biol. 1995, 2, 621) who prepared a series of carbamate mixtures which were screened for acetylcholinesterase inhibitory activity. Prior to these efforts, Rebek's group reported the single-step construction of large libraries presenting amino acid derivatives attached to rigid core templates with a reliance on amide or urea bond formation (Carell et al. Angew. Chem., Int. Ed. Engl. 1994, 33, 2059; Carell et al. Bioorg. Med. Chem. 1996, 4, 655; Dunayevskiy et al. Anal. Chem. 1995, 67, 2906; Carell et al. Chem. Biol. 1995, 2, 171). Because of the complexity of the combinatorial libraries resulting from this approach (approaching 100,000 members), an iterative selection strategy based on structural grouping of the building blocks was devised.

In addition to recent advances in this work, substantial progress towards using solution-phase multicomponent reactions for generating combinatorial mixtures has been disclosed. For example, both Ugi and Armstrong have reported Ugi four-component condensations including the incorporation of a modifiable isocyanide in combination with resin capture strategy, to provide useful solution-phase library preparations (Ugi et al. Endeavour 1994, 18, 115; Keating et al. J. Am. Chem. Soc. 1996, 118, 2574; Armstrong et al Acc. Chem. Res. 1996, 29, 123).

Our own efforts have focused on the development of a multistep, solution-phase strategy for the preparation of chemical libraries which relies upon the simple removal of excess reactants and reagents by liquid-liquid or liquid-solid extraction procedures. The application of water-soluble coupling reagents in solution-phase peptide synthesis was introduced by Sheehan et al. J. Org. Chem. 1956, 21, 439.

The approach has been shown to dependably deliver pure, individual compounds in multi-milligram quantities, and chemical libraries of >1000 individual members have been assembled (Cheng et al. J. Am. Chem. Soc. 1996, 118, 2567; Boger et al. J. Am. Chem. Soc. 1996, 118, 2109; Cheng et al. Bioorg. Med. Chem. 1996, 4, 727; Tarby et al. In Molecular Diversity and Combinatorial Chemistry: Libraries and Drug Discovery Chaiken, I. M., Janda, K. D., Eds.; ACS: Washington, 1996; 81). Notably, it avoids the disadvantages of solid-supported synthesis including its restrictive scale, the required functionalized substrates and solid supports, compatible spacer linkers, and the requirements for othogonal attachment/detachment chemistries typically with the release of spectator functional groups. It does not require specialized protocols for monitoring the individual steps of multistep syntheses including orthogonal capping strategies for blocking unreacted substrate and does provide the purification of sequence intermediates. This latter disadvantage of solid-supported synthesis necessarily produces the released product of a multistep sequence in an impure state or requires that each reaction on each substrate proceed with an unusually high efficiency.

Ligand-induced receptor and protein dimerization or oligomerization has emerged as a general mechanism for signal transductionl and members of the important receptor superfamilies are activated by such a process. These include protein tyrosine kinase receptors (homo- or heterodimerization), class I cytokine receptors (homo- or heterodimerization), serine/threonine kinase receptors (hetero-oligomerization), and members of the TNF-receptor family (trimerization), FIG. 20. Within the cytokine receptor superfamily, the most extensively studied examples are the human growth hormone (hGHr), prolactin (PRLr) and erythropoietin receptors (EPOr), which form homodimers upon binding their ligands. Similarly, intracellular signal transduction often proceeds by protein-protein homo- or heterodimerization and important examples include activators of transcription (e.g., Myc-Max dimerization, STAT homo- and heterodimers).

Important therapeutic applications may emerge from either the development of agonists or antagonists of such receptor or protein dimerization and representative examples are provided in FIG. 21 for the cytokine receptor superfamily. Our interest in combinatorial chemistry rested on its potential. ability to provide candidate leads for promoting receptor activation by dimerization which to our knowledge had not emerged from screening natural products. This interest in studying receptor activation via dimerization and the potential of utilizing a single approach for the discovery of antagonists and their conversion to agonists was one important element underlying our pursuit of solution-phase combinatorial chemistry at a time when solid-phase techniques were considered most valuable.

What is needed are small molecule libraries of C2-symmetric and unsymmetric chemical compounds for use in protein and receptor homodimerization and heterodimerization studies as described above. Furthermore, what is needed is an economical method for the rapid and multi-milligram preparation of said targeted C2-symmetric and unsymmetric chemical libraries.

SUMMARY OF THE INVENTION

One aspect of the invention is directed to a convergent process for synthesizing a symmetric combinatorial library. In the first step of the process, a template and n addition reagents, wherein n is greater than 3, are provided. The template is of a type which includes a linkage site and at least two addition sites. The linkage site is employable for dimerizing the template. Each of the addition sites is employable for conjugating the addition reagents onto the template. A combinatorial sublibrary is then constructed by conjugating each of the addition sites of the template with a subset of the n addition reagents in a combinatorial fashion. The combinatorial sublibrary constructed in the prior step is then dimerized by cross linking the linkage site for constructing the symmetric combinatorial library. In a preferred mode of the invention, both the conjugation and cross linking steps occur in solution phase. In an alternative preferred mode, a cross linking agent is employed for cross linking the linkage sites. Symmetric combinatorial libraries constructed by the above convergent process are further aspects of the invention.

Another aspect of the invention is directed to a convergent process for synthesizing an asymmetric combinatorial library. In the first step of the process, a first template, a second template, and n addition reagents, wherein n is greater than 3, are provided. The first template has a first linkage site and at least two addition sites. The second template has a second linkage site and at least two addition sites. The first and second linkage sites are employable for linking the first template to the second template. Each of the addition sites are employable for conjugating the addition reagents onto the template. A first combinatorial sublibrary is then constructed by conjugating each of the addition sites of the first template with a first subset of the n addition reagents in a combinatorial fashion. A second combinatorial sublibrary is then constructed by conjugating each of the addition sites of the second template with a second subset of the n addition reagents in a combinatorial fashion. The first and second combinatorial sublibraries constructed in the above two conjugation steps are then dimerized by cross linking the first linkage site on the first template of the first combinatorial sublibrary with the second linkage site on the second template of the second combinatorial sublibrary, so as to construct the asymmetric combinatorial library. In a preferred mode of the invention, both the conjugation and cross linking steps occur in solution phase. In an alternative preferred mode, a cross linking agent is employed for cross linking the linkage sites. Asymmetric combinatorial libraries constructed by the above convergent process are further aspects of the invention.

Another aspect of the invention is directed to a convergent process for synthesizing a double dimerized combinatorial library. In the first step of the process, a first template, a second template, a third template, a fourth template and n addition reagents, wherein n is greater than 3, are provided. The first template has a first linkage site and at least two addition sites. The second template has a second linkage site and at least two addition sites. The first and second linkage sites are employable for linking the first template to the second template. Each of the addition sites are employable for conjugating the addition reagents onto the template. A first combinatorial sublibrary is then constructed by conjugating each of the addition sites of the first template with a first subset of the n addition reagents in a combinatorial fashion. A second combinatorial sublibrary is then constructed by conjugating each of the addition sites of the second template with a second subset of the n addition reagents in a combinatorial fashion. A third combinatorial sublibrary is then constructed by conjugating each of the addition sites of the third template with a third subset of the n addition reagents in a combinatorial fashion. A fourth combinatorial sublibrary is then constructed by conjugating each of the addition sites of the fourth template with a fourth subset of the n addition reagents in a combinatorial fashion. The first and second combinatorial sublibraries are then dimerized by cross linking the first linkage site on the first template of the first combinatorial sublibrary with the second linkage site on the second template of the second combinatorial sublibrary. Dimerization is achieved using a first cross linking agent having a first supplemental linkage site for cross linking the first cross linking agent. The first supplemental linkage site is of a type which is unreactive with the linkage site of the first and second templates. The dimerization achieves the construction of a first intermediate combinatorial library. The third and fourth combinatorial sublibraries are then dimerized by cross linking the third linkage site on the third template of the third combinatorial sublibrary constructed with the fourth linkage site on the fourth template of the fourth combinatorial sublibrary. Dimerization is achieved using a second cross linking agent having a second supplemental linkage site for cross linking the second cross linking agent. The second supplemental linkage site is of a type which is unreactive with the linkage site of the third and fourth templates. The dimerization achieves the construction of a second intermediate combinatorial library. The double dimerized combinatorial library is then produced by linking the first supplemental linkage of the first intermediate combinatorial library with the second supplemental linkage of the second intermediate combinatorial library. In a preferred mode of the invention, both the conjugation and cross linking steps occur in solution phase. In an alternative preferred mode, a cross linking agent is employed for cross linking the linkage sites. Double dimerized combinatorial libraries constructed by the above convergent process are further aspects of the invention.

Another aspect of the invention is directed to a process for converting a first combinatorial library having an antagonist activity with respect to a receptor to a second combinatorial library having an agonist activity with respect to the same receptor. The receptor is of a type which is activated by dimerization. In the first step of the process, the first combinatorial library is provided. The first combinatorial library has n elements. At least one of the n elements has the antagonist activity with respect to the receptor. Each of the n elements has a linkage site for dimerization. The first combinatorial library is then dimerized by cross linking the linkage sites of the n elements with one another, including elements having the antagonist activity, for producing the second combinatorial library. Upon dimerization, the elements having antagonist activity in the first combinatorial library are converted to elements having agonist activity in the second combinatorial library. In a preferred mode of the invention, the cross linking step occurs in solution phase. In an alternative preferred mode, a cross linking agent is employed for cross linking the linkage sites. Agonist combinatorial libraries having an agonist activity with respect to a receptor, the receptor being of a type which is activated by dimerization, are further aspects of the invention.

Another aspect of the invention is directed to a deletion method for deconvoluting combinatorial libraries.

BRIEF DESCRIPTION OF FIGURES

FIG. 7 illustrates a table which depicts isolated Amounts (mg) and Yields (%) of the 60 Final Sub-libraries AXBXC1–10 (4).

FIG. 11 illustrates the precursors assembled in a matrix 6×6×4 format with the 6 iminodiacetic acid diamides being prepared by parallel synthesis and with the last reaction conducted with a mixture of 4 ω-alkene carboxylic acids.

FIG. 13 shows a table which depicts yields (%) of the library precursors.

FIG. 15 shows a table which depicts yields (%) of the Sub-Library Reactions.

FIG. 17 illustrates the synthesis of iminodiacetic acid diamide libraries (the individual preparations of A1B1C1–A1B1C4 and their sequential symmetrical dimerizations) with a two-fold dimerization to convert the monomers first to dimers and then to tetramers incorporating eight variable groups.

FIG. 20 shows a table which depicts Class I cytokine receptors and protein-tyrosine kinase receptors activated by dimerization or oligomerization with the following abbreviations: R, receptor; receptor; CSF, colony-stimulating factor; GH, growth hormone; EPO, erythropoietin; PRL, rolactin; IL, interleukin; LIF, leukemia inhibitory factor; CNTF, ciliary neurotrophic factor; PDGF, platelet-derived growth factor; SCF, stem cell factor; CSF, colony-stimulating factor; EGF, epidermal growth factor; FGF, fibroblast growth factor, IGF, insulin-like growth factor; HGF, hepatocyte growth factor; MSP, microphage-stimulating protein; VEGF, vascular endothelial growth factor; FN, fibronectin.

FIG. 21 shows a table which depicts approved/potential therapeutic applications of cytokine agonists and antagonists.

FIG. 23 shows a table which depicts yields (%) of the Library Precursors and yields (%) of the Sublibrary Reactions

FIG. 25 shows a table which depicts yields (%) of the Olefin Metathesis Tetramer Library.

DETAILED DESCRIPTION OF THE INVENTION

Figure 1:
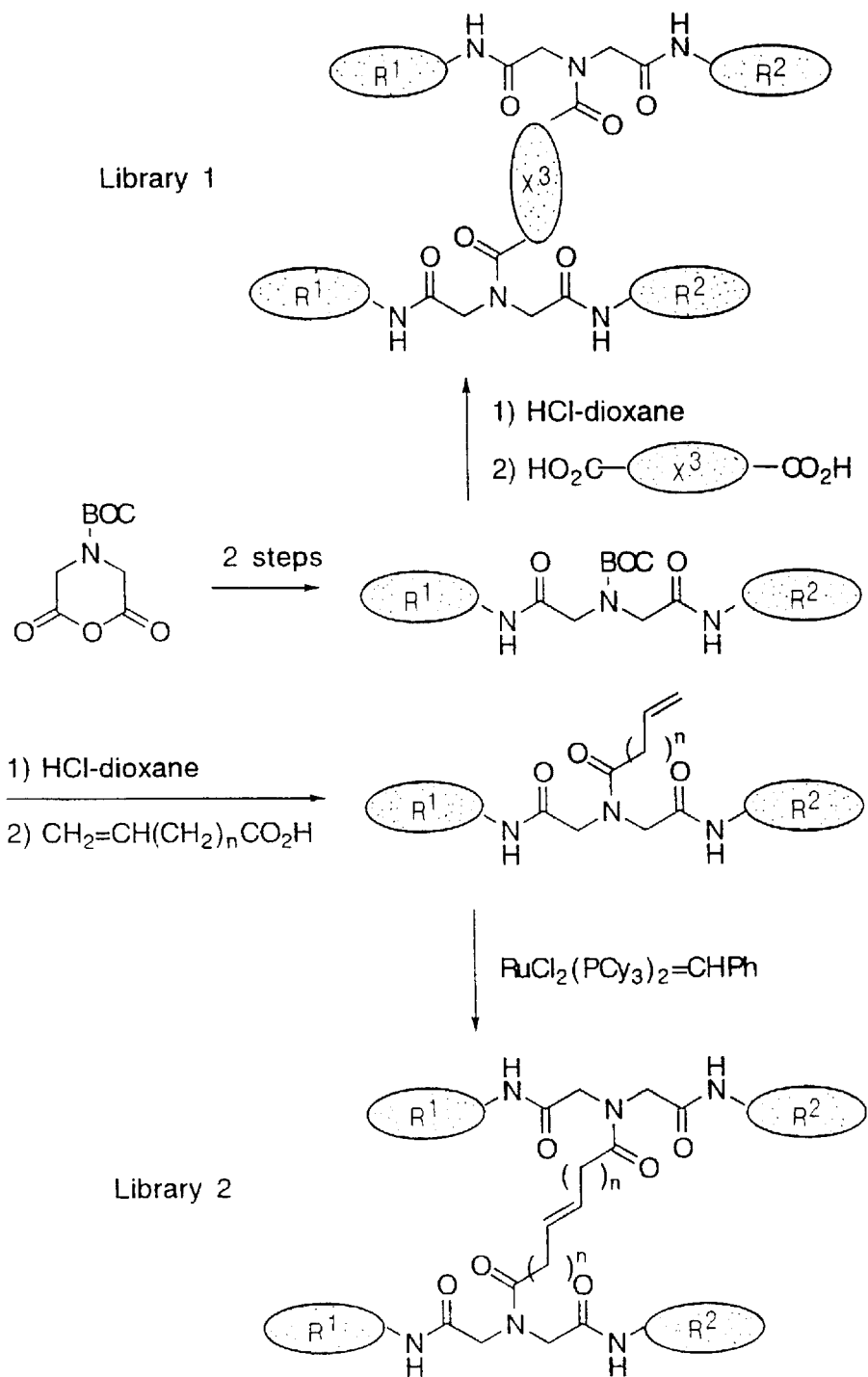
FIG. 1 illustrates two effective protocols for generating C2-symmetrical or unsymmetrical chemical libraries suitable for probing receptor and protein homodimerization and heterodimerization events.

The invention is directed to a novel assembly of targeted C2-symmetric and unsymmetric chemical libraries for use in protein and receptor homodimerization and heterodimerization studies by solution phase methods. The methodology permits the multi-milligram preparation of each member. The synthesis of the first prototypical library was based on the symmetrical linking of iminodiacetic acid diamides. The final library was prepared in a 60 to 10 sub-library format by symmetrical coupling of the constructed fragments with a mixture of tethering dicarboxylic acids. In each step of the 3-step reaction sequence, the reactants, unreacted starting material, reagents and their byproducts were removed by simple liquid-liquid or liquid-solid extractions providing the desired intermediates and final libraries in multi-milligram quantities in high purities (≥90–100%) independent of the reaction yields and without deliberate reaction optimization.

The synthesis of a second prototypical library employed the olefin metathesis reaction to join and combinatorially randomize the length of linker tether. This approach provides a unique opportunity to rapidly generate a statistically controlled mixture of homo and heterodimers of remarkable diversity. Examples of this latter strategy to prepare a 300 (600 including cis/trans isomers) member library from 6 iminodiacetic acid diamides functionalized with 4 terminal w-alkenes are described. This was conducted in a single reaction employing the mixture of 24 compounds or in 15 reactions conducted with pair-wise combinations of the reacting monomers to produce 15 sub-libraries containing 36 defined homo- and heterodimer metathesis products (72 compounds including cis/trans isomers). Similarly, the corresponding 6 sub-libraries of homodimer metathesis products containing 10 members (20 compounds including cis/trans olefin isomers) each were prepared by conducting a total of 6 reactions.

EXAMPLE 1

Generation of Targeted $C_2$-Symmetrical and Unsymmetrical Compound Libraries by Solution-Phase Combinatorial Chemistry In this example, we disclose the development of two effective protocols for generating C2-symmetrical or unsymmetrical chemical libraries suitable for probing receptor and protein homodimerization and heterodimerization events (FIG. 1). Our initial efforts represent the assembly of a chemical library of 600 members, targeted towards EPOr (Wells et al. Science 1996, 273, 449; Erythropoietin: Basic and Clinical Aspects, Spivak, J. L., Ed.; W. B. Saunders: Philadelphia, 1994; Vol.8) by way of solution-phase combinatorial chemistry.

The approach constitutes the dimerization linkage of iminodiacetic acid diamides with a mixture of rigid dicarboxylic acids. The entire reaction sequence requires 3 steps. The solution-phase synthesis of the fragments permits their final direct linkage which would be precluded by more conventional solid-phase synthesis techniques. As such, the strategy is uniquely suited for taking advantage of such symmetrical diversity utilizing a limited number of synthetic steps (FIG. 1).

The second approach further expands on this by employing the olefin metathesis reaction to join and combinatorially randomize the length of the linking tether (Grubbs et al. Acc. Chem. Res. 1995, 28, 446; Grubbs et al. Science 1989, 243, 907; Schwab et al. Angew. Chem., Int. Ed. Engl. 1995, 34, 2039; Schuster et al. Angew. Chem., Int. Ed. Engl. 1996, 35, 1979; Tetrahedron Lett. 1996, 37, 8249). This approach provides a unique opportunity to rapidly generate a statistically controlled mixture of remarkable diversity. Examples of this strategy to prepare a 300 member library (600 compounds including cis/trans olefin isomers) from just 24 components derived from only 6 iminodiacetic acid diamides each functionalized with 4 terminal w-alkenes are detailed. The examples include the library generation in a single reaction of the 24 components or in 15 reactions conducted with pair-wise combinations of reacting monomers to produce 15 sub-libraries containing 36 members (72 compounds) each.

Similarly, the corresponding 6 sub-libraries of homodimers containing 10 members (20 compounds) each were prepared by conducting only 6 reactions. Although recent preliminary reports of the use of the olefin metathesis reaction for the cross-coupling of solution with resin bound olefins as well as for the release of resin bound olefins by ring closure metathesis have been disclosed (Schuster et al. Angew. Chem., Int. Ed. Engl. 1996, 35, 1979) its use to combinatorially randomize and statistically generate diversity has not been detailed. As described herein, the reaction seems particularly well-suited for the solution-phase construction of homo- and heterodimerization libraries.

Results and Discussion

Figure 2:
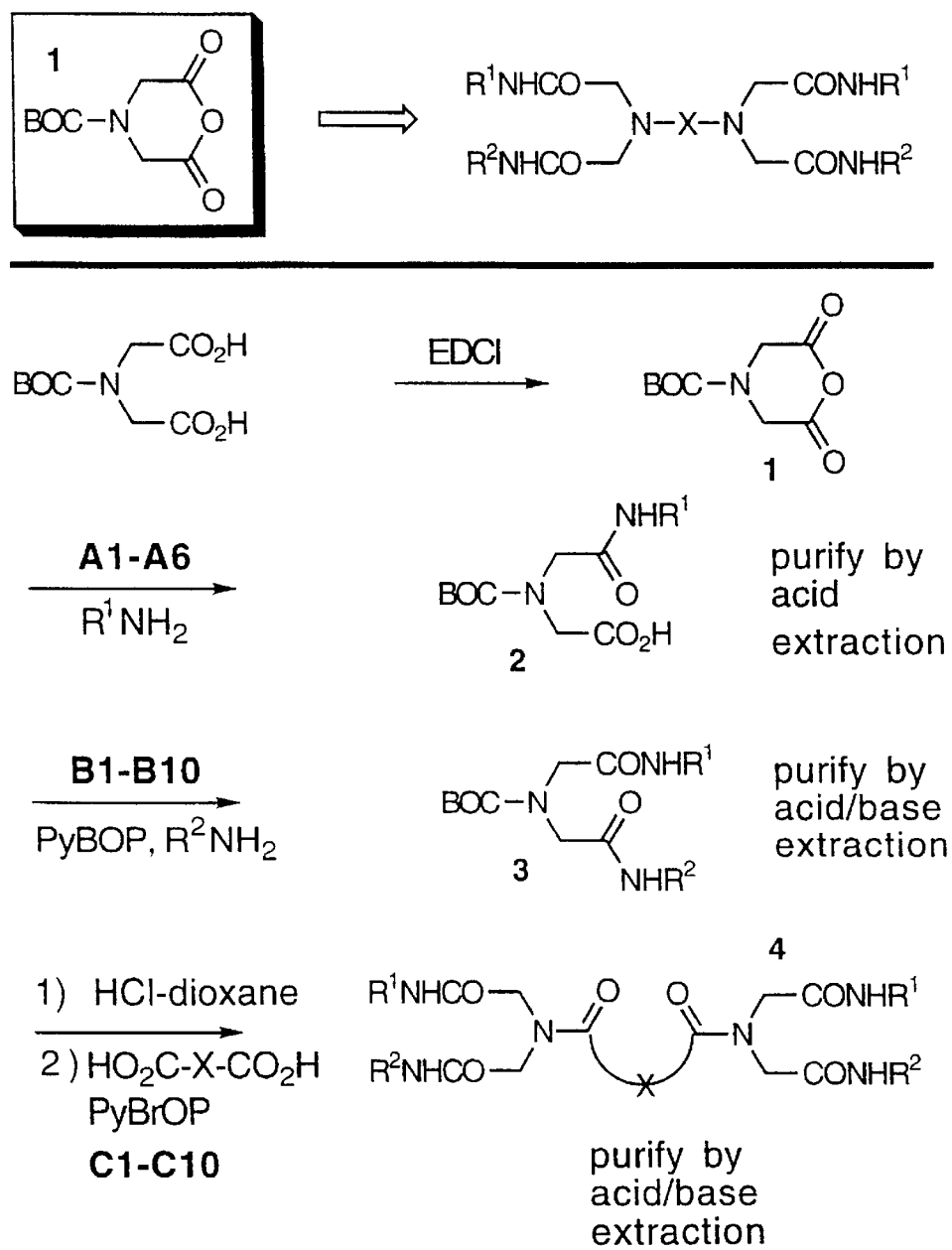
FIG. 2 illustrates a scheme for generating libraries that minimizes the number of executed chemical reactions, that maximizes the diversity impact and that provides a convenient screening/deconvolution format.
Figures 3, 4:
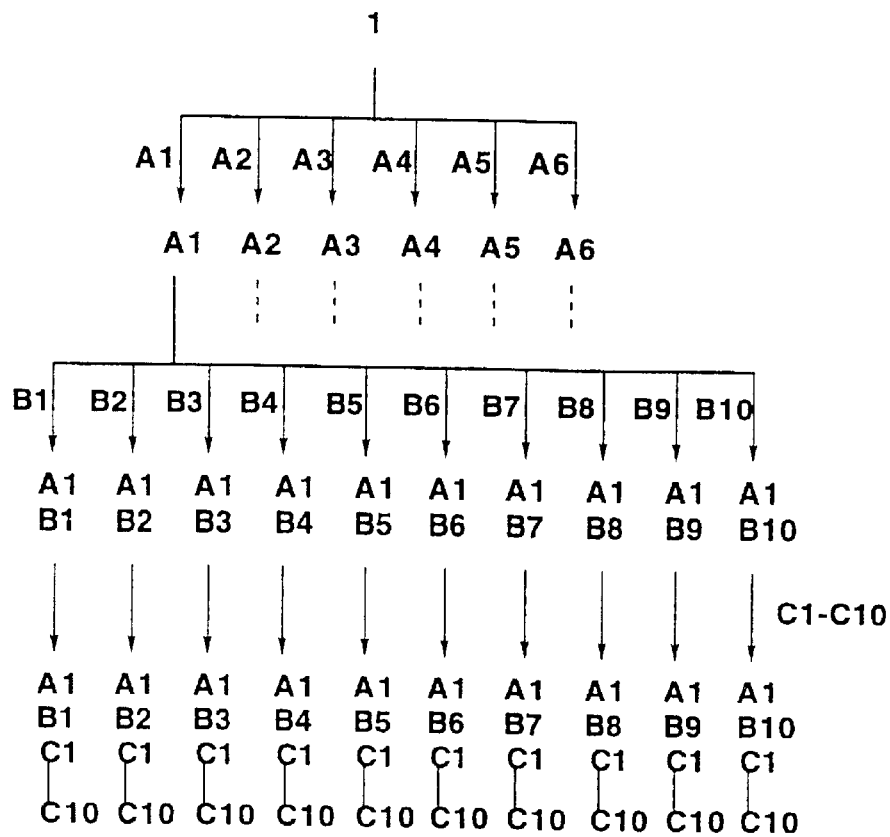
FIG. 3 illustrates a library of 600 C2-symmetric compounds constructed in a 6×10×10 matrix with the final diversification being accomplished in one reaction to provide a mixture of 10 compounds containing variations in only the linking domain.
FIG. 4 illustrates a table which depicts isolated yields (%) of 2 and 3.

C2-Symmetric Library 1. In a design that minimizes the number of executed chemical reactions, that maximizes the diversity impact and that provides a convenient screening/deconvolution format, a library of 600 C2-symmetric compounds was constructed in a 6×10×10 matrix with the final diversification being accomplished in one reaction to provide a mixture of 10 compounds containing variations in only the linking domain (FIGS. 2 and 3). For the 3-step synthesis, this required 6 amines (R1NH2, A1–A6), 10 amines (R2NH2, B1–B10), and 10 dicarboxylic acids (HO2C-X-CO2H, C1–C10) for diversity input, and the conduct of 126 reactions to produce 60 sub-libraries each containing 10 C2-symmetric compounds containing variations only on the linking domain. Deconvolution of such a mixture by resynthesis of the individual components is straightforward and the biological or screening assays applied to a modest mixture of 10 compounds was judged optimal. In addition to the advantages associated with the testing of a modest mixture of 10 compounds, the variability within each sub-library was only in the precise nature of the linker. This was judged to potentially minimize the false positive or false negative screening results that accompany the testing of mixtures of compounds and, at the same time, permit the simultaneous examination of a range of linkers. Moreover, when this format is applied in a pair-wise fashion for the construction of C2-symmetric and unsymmetric compound libraries (i.e. A1B1+A1B2+C1–C10), the final mixtures contain 30 compounds composed of each of the two C2 symmetric sub-libraries (10+10, A1B1C1–10+A1B2C1–C10) plus the unsymmetrical combination (10).

Testing the modest mixture of 30 compounds constitutes the upper limit judged valuable (Terrett et al. J. Bioorg. Med. Chem. Lett. 1995, 5, 917) and the full library size including the unsymmetrical combinations would be 18,300 compounds built with only 26 diversity units (6+10+10) as shown in FIGS. 2 and 3.

Figure 5:
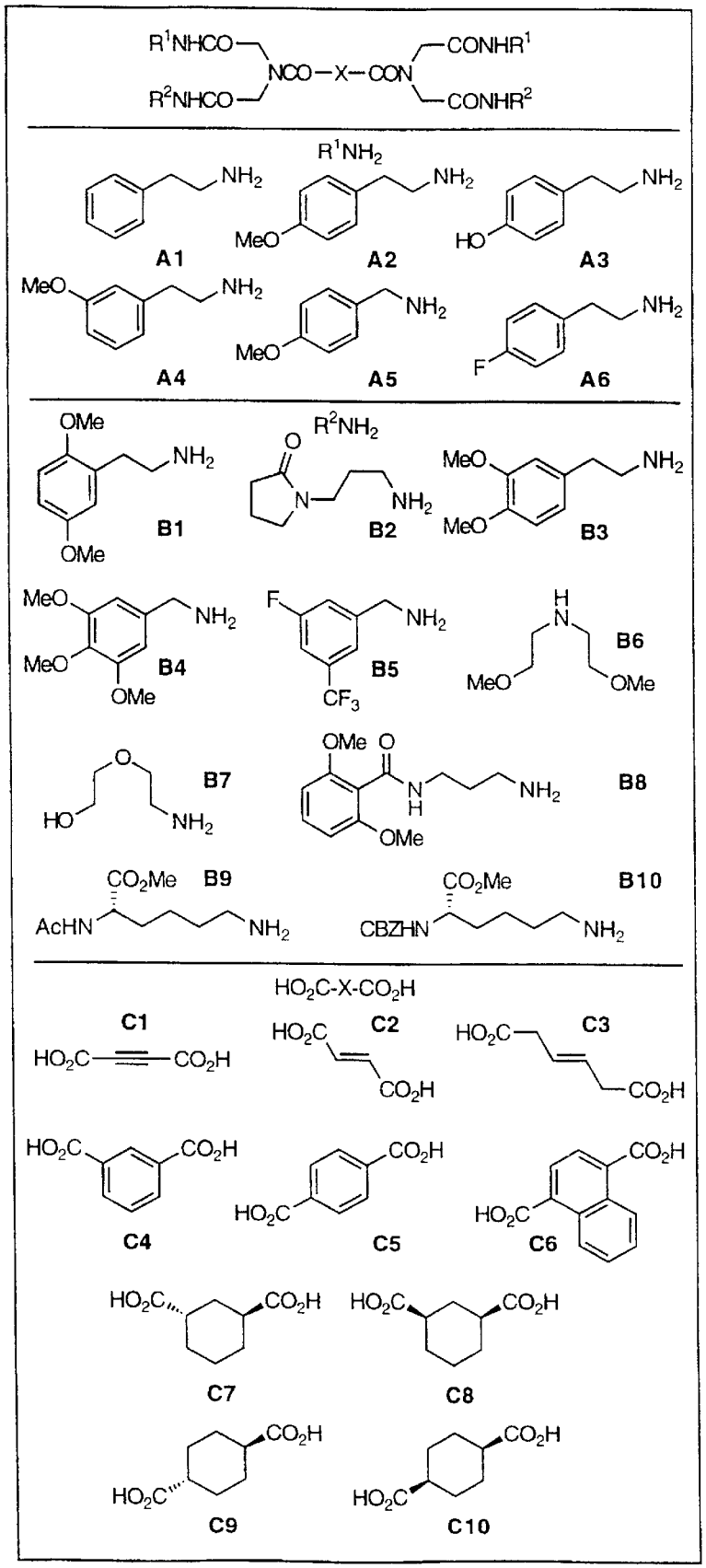
FIG. 5 illustrates primary amines A1–A6, secondary amines B1–B10 and dicarboxylic acids which were used to produce the 60 sub-libraries of 10 compounds as described in example 1.

Reaction of N-BOC-iminodiacetic acid with the water-soluble coupling reagent 1-(3-dimethylaminopropyl)-3-ethylcarbodiimide hydrochloride (EDCI, 1–1.05 equiv, DMF, 25° C., 1 h), and subsequent in situ anhydride ring-opening with the 6 primary amines A1–A6 (R1NH2, 1 equiv, DMF, 25° C., 12 h, 64–99%) was conducted on 20 mmol scales and proceeded to yield approximately 7 g of the monoamides 2 in superb yields (avg=90%), FIGS. 4 and 5. Simply washing the crude product diluted in EtOAc with aqueous acid served to remove unreacted R1NH2, EDCI and its reaction byproducts and provided the pure monoamides (≧95% pure); FIGS. 4 and 5.

Each of the 6 monoamides were partitioned into 10 portions with an additional larger portion retained for archival and resynthesis purposes. Each of the 10 equal portions were treated with the 10 primary or secondary amines (B1–B10, 1.1 equiv) and PyBOP (1.1 equiv, 2–2.2 equiv i-Pr2NEt, DMF, 25° C., 16 h, 7–99%) to afford a total of 60 diamides which were effectively purified by sequential acid (10% aqueous HCl), base (saturated aqueous NaHCO3), and saturated aqueous NaCl extractions from EtOAc to remove reagent-derived reaction byproducts, unreacted starting material, R2NH2, and PyBOP. Each reaction was conducted on a 1.75 mmol scale corresponding to approximately 600 mg of starting monoamide. The individual yields of the N-BOC iminodiacetic diamides 3 ranged from 7–100% (FIG. 4), with an average of 53%. The lower yielding reactions were compromised by the water-solubility of the products. Thus, yields in the 7–42% range were encountered for the reactions employing entries B2, B7, and B9, whereas the less polar products (i.e., B10 versus B9) were generally isolated in near quantitative yields. Irrespective of the reaction efficiency or product recovery and without deliberate reaction optimization, the purities of the resulting diamides were uniformly satisfactory (≧290–95%) and the identities of products were confirmed by matrix characterization (HRMS, 1H NMR and IR).

Figure 6:
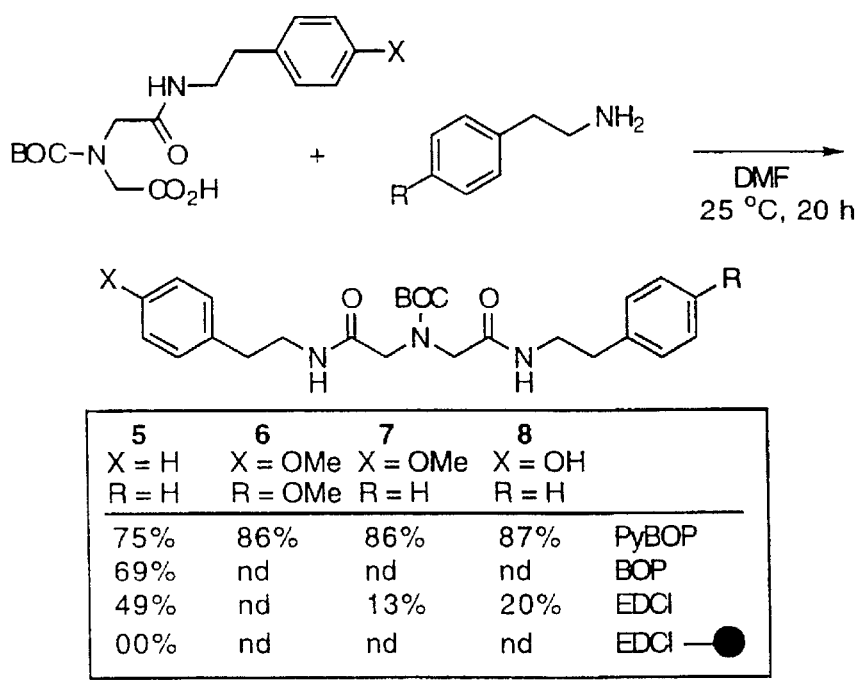
FIG. 6 shows a scheme which examines alternatives to PyBOP for the second coupling. We found that EDCI and BOP-Cl were less effective than PyBOP.

We briefly examined alternatives to PyBOP for the second coupling and found that. EDCI and BOP-Cl were less effective than PyBOP (FIG. 6). In addition, although a polymer-supported version of EDCI30 was ineffective at promoting the second coupling to provide the diamides 3, it was found to constitute a convenient alternative for the in situ conversion of N-BOC-iminodiacetic acid to the corresponding anhydride for the first functionalization reaction with the generation of 2 (A3, 68%; DMF, 25 ° C., 20 h) as shown in FIG. 6.

The final assembly of the targeted C2-symmetrical library of 600 compounds entailed 60 coupling reactions each composed of one iminodiacetic acid diamide (A1B1–A6B10) and an equimolar mixture of 10 dicarboxylic acids (C1–C10) producing 60 sub-libraries of 10 compounds each containing variations only in the linking subunit. This was effectively accomplished by acid-catalyzed deprotection of 3 (4 M HCl-dioxane, 25° C., 2 h) conducted on each of the individual 60 iminodiacetic acid diamides (A1B1–A6B10, 0.15 mmol) followed by coupling (0.15 mmol PyBrOP, 0.45 mmol i-Pr2NEt, DMF, 25° C., 12 h, 9–99%) of the crude amine hydrochloride salt with an equimolar mixture of the dicarboxylic acids C1–C10 (0.005 mmol each, 0.05 mmol total, 0.67 equiv). The use of the secondary amine in excess for a prolonged reaction time insured the coupling consumption of the limiting diacid linkers and the near equimolar generation of each sub-library member. Purification by sequential aqueous acid and aqueous base extractions served to remove the unreacted excess secondary amines derived from AXBX, any unreacted dicarboxylic acids C1–C10 as well as any monocarboxylic acid contaminant derived from partial reactions of C1–C10, the excess reagents (PyBrOP, i-Pr2NEt) and their reaction byproducts. Using this protocol, each of the 60 sub-libraries of 10 compounds was produced in yields ranging from 9–99% (57% average) in amounts ranging from 4.2–52 mg (FIG. 7). Irrespective of the conversion, the extractive purification coupled with the scale provided the libraries in high purity (≧90%) and in sufficient quantity suitable for direct broad screening in a variety of assays. Matrix characterization of the 60 sub-libraries by MS and 1H NMR confirmed the constitution of the mixtures and the detailed evaluation of the prototypical sub-library A2B6C1–10 established the integrity of the mixture as described below.

Although 1H NMR was not especially useful at quantitating the mixture components and only marginally useful at qualitatively establishing the mixture identity, it was effective at identifying and quantitating contaminate secondary amine (AXBX), reagents (PyBrOP, i-Pr2NEt), and reagent-derived reaction byproducts in the sub-libraries insuring the integrity of the extraction workup/purification (FIG. 7).

Figure 8:
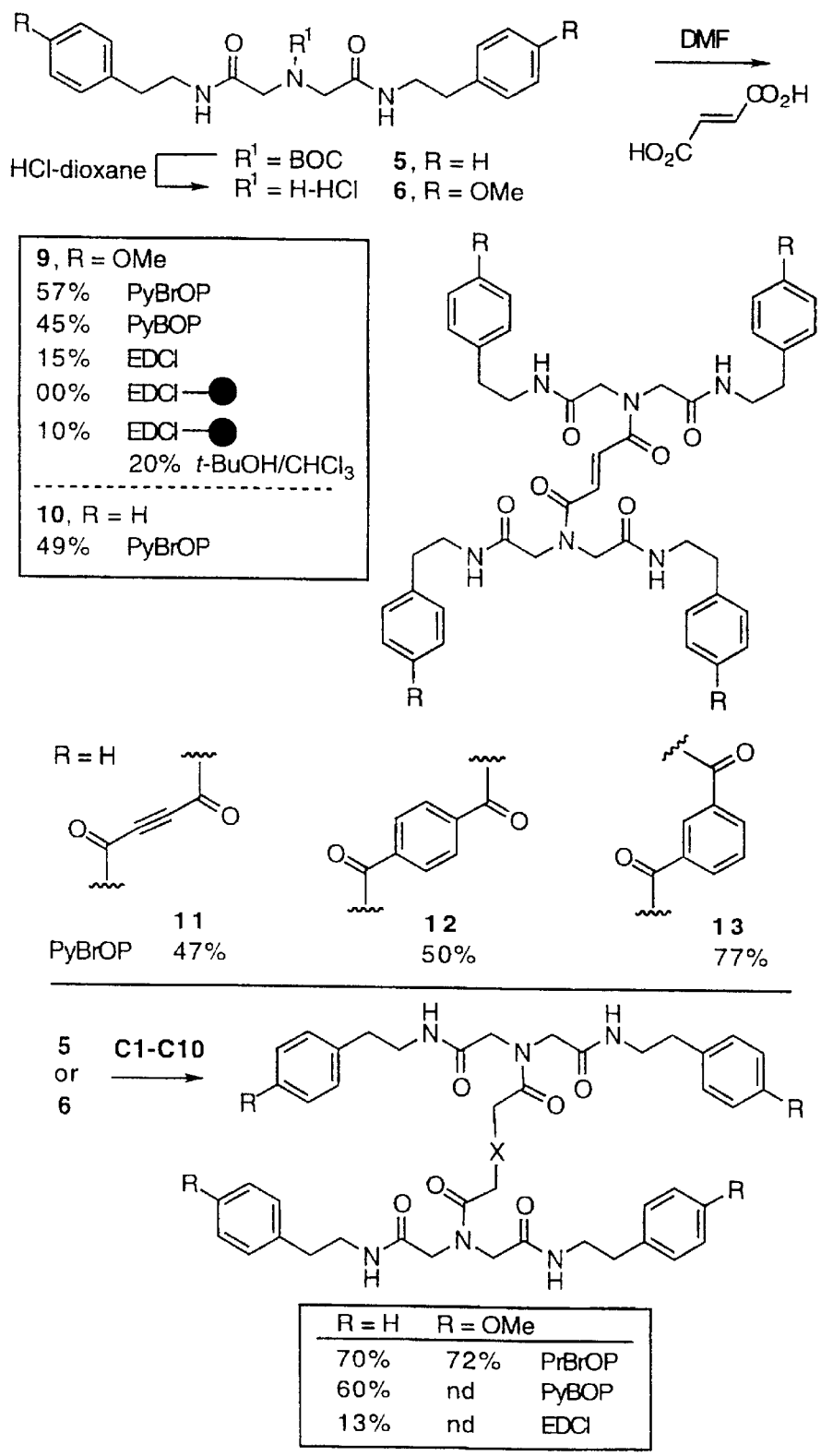
FIG. 8 shows that, while both PyBOP and EDCI proved less satisfactory for promoting both the individual and mixture coupling of 5 and 6 with C1–C10, PyBrOP31 smoothly provided the symmetrically linked dimers.

That this protocol would produce the sub-libraries satisfactorily was first demonstrated by examining the linkage coupling of the models 5 and 6, their coupling with the C1–C10 mixture, and ultimately with the individual and mixture construction of the sub-library A2B6C1–C10. While both PyBOP and EDCI proved less satisfactory for promoting both the individual and mixture coupling of 5 and 6 with C1–C10, PyBrOP31 smoothly provided the symmetrically linked dimers (FIG. 8). Considerable effort was made to optimize the conversions, equimolar generation of the resulting mixture of products, the extraction recovery and the purity of the final products. In particular, it was considered important to minimize the generation of monocoupled product, and to counteract possible differences in diacid reactivity by using the secondary amine in excess. Such a stoichiometry also makes accurate weighing of the intermediate N-BOC-iminodiacetic diamides 3 unnecessary. In addition, excess i-Pr2NEt was employed to neutralize any residual acid remaining after BOC deprotection. It was established that conducting the reaction with excess AXBX (0.3 mmol) versus dicarboxylic acid (0.1 mmol, 0.67 equiv) for 8–24 h in the presence of PyBrOP (0.3 mmol) and i-Pr2NEt (0.9 mmol) would lead to satisfactory conversions with the consumption of the C1–C10 dicarboxylic linker. Conventional extractive workup with aqueous 10% HCl to remove unreacted AXBX and i-Pr2NEt led to occasional loss of product due to its water solubility especially with the more hydrophilic sub-libraries. The use of both an acidic ion exchange resin (liquid-solid extraction, DOWEX 50WX8-400) and aqueous 20% HCl saturated with NaCl improved the mass balance recovery and effectively removed the excess amine reactants and reagents. Using either of these protocols, the final extractive purification provided the individual compounds and the mixture sub-libraries at an exceptional level of purity with satisfactory recoveries and the latter was adopted for the preparation of our prototypical library as shown in FIG. 8.

Figure 9:
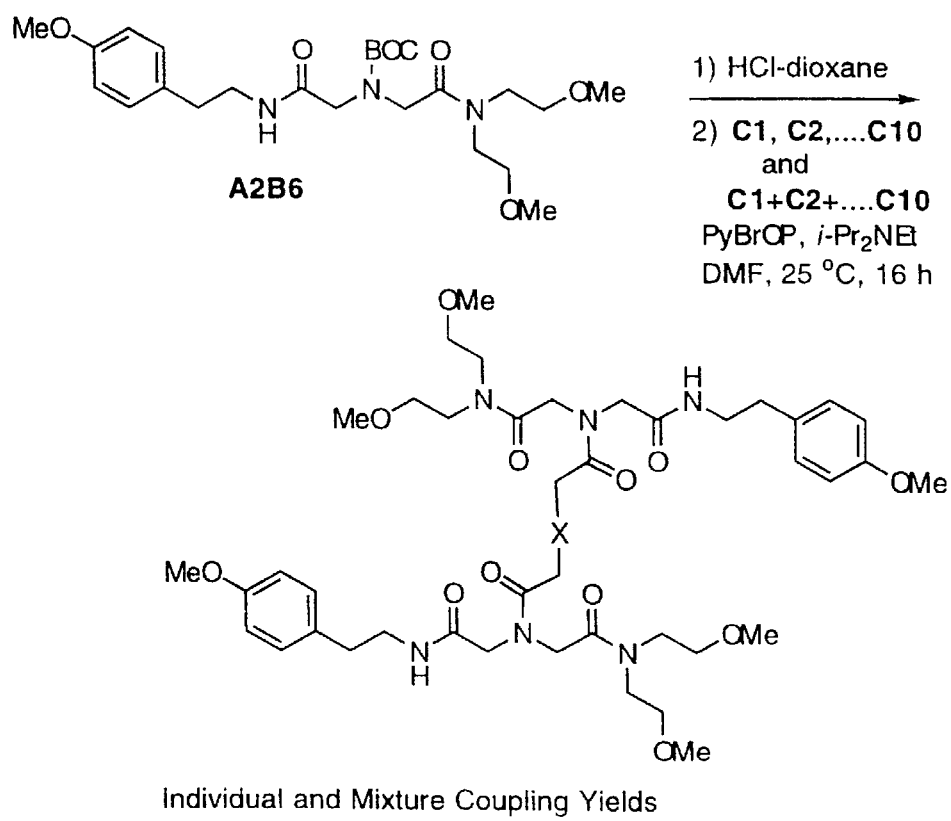
FIG. 9 illustrates the preparation of sub-library A2 B6 C1–C10 using the optimized reaction conditions and the modified extraction workup/purification by running each of the 10 individual coupling reactions and the mixture coupling reaction.

Finally, prior to implementing the full library synthesis, the sub-library A2B6C1–C10 was prepared using the optimized reaction conditions and the modified extraction workup/purification by running each of the 10 individual coupling reactions and the mixture coupling reaction (FIG. 9). The conversions and recovery (70–100%, 90% avg) as well as the purity ($\geq$90–95%) of the individual reactions were uniformly high and correspond nicely to the mixture coupling reaction (95% yield, >90% purity). Following complete characterization (1H NMR, IR, HRMS) of the eight separate products (A2B6C1–A2B6C10), these were subjected to reverse-phase HPLC separation, both separately and after pooling in equimolar proportions. The MS established the presence of each mixture component and both 1H NMR and HPLC revealed no significant differences in the two mixtures. The reconstituted equimolar mixture of A2B6C1–C10 prepared from the individual pure components and that derived from the mixture coupling proved to be essentially indistinguishable. Thus, the mixture coupling was established to provide a near equimolar mixture of the reaction products with only subtle differences detected and each of the 10 components was found to be present in the final sub-library (FIG. 9).

Figure 10:
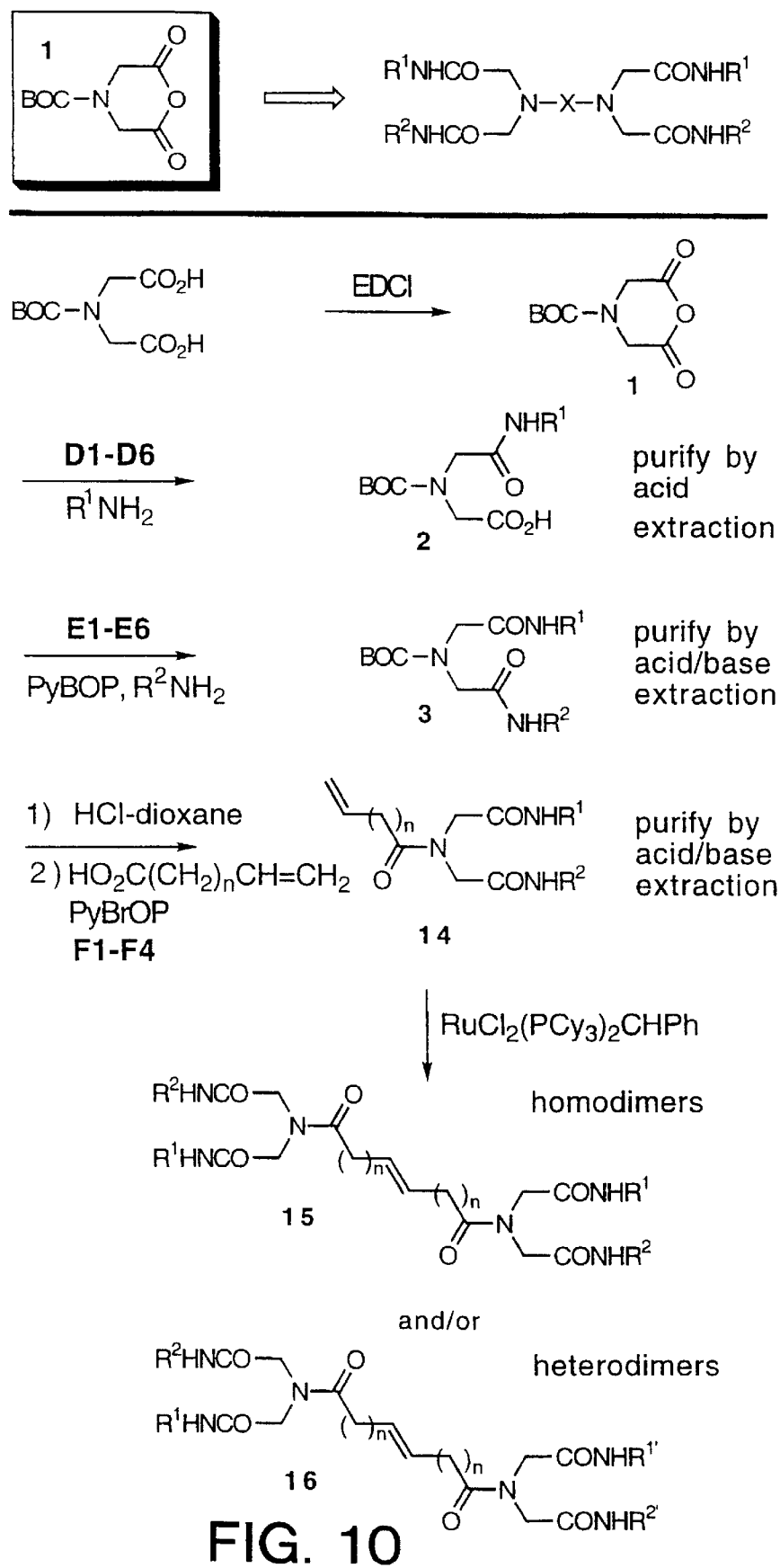
FIG. 10 illustrates a combinatorial library of C2-symmetric and unsymmetrical compounds with both the linkage and diversification of the linker domain created by use of the olefin metathesis reaction.
Figure 12:
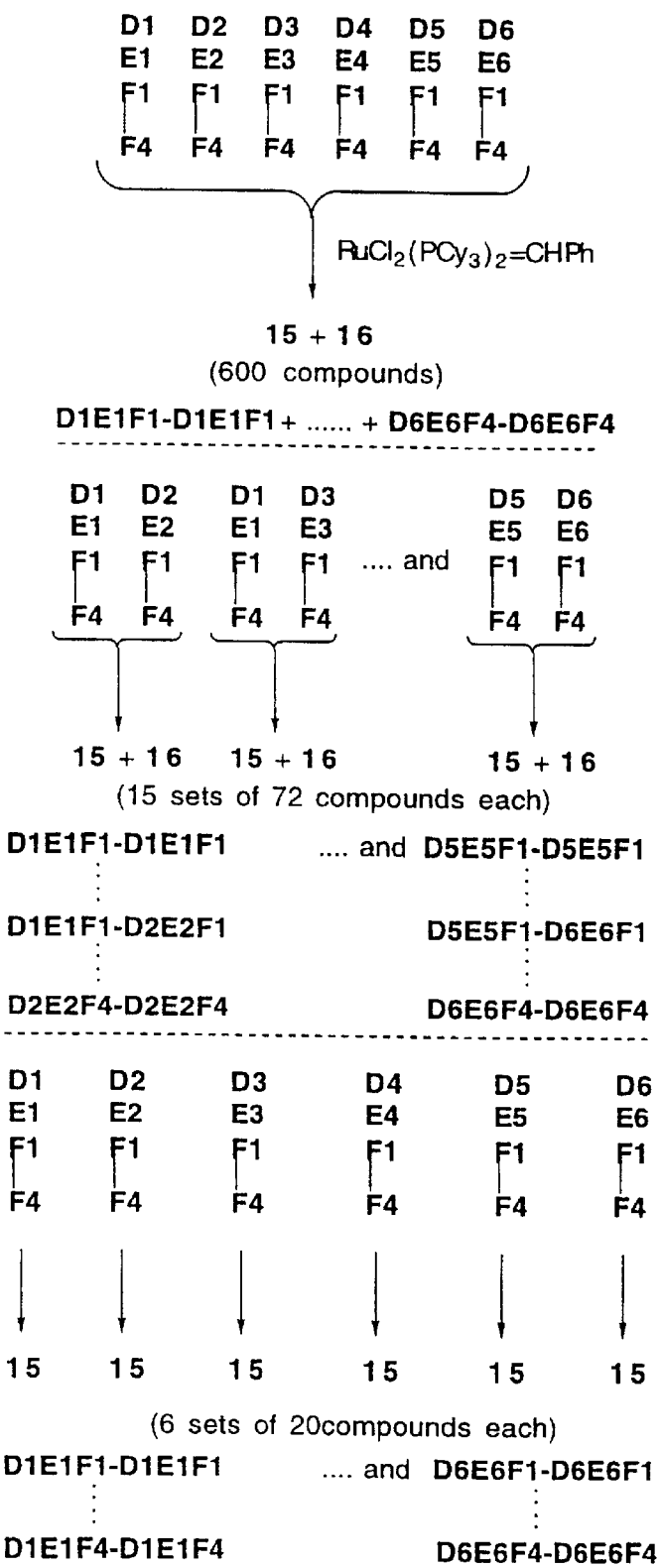
FIG. 12 illustrates the 24 precursors which were assembled in 3 parallel steps as 6 mixtures each containing 4 compounds with variations in only the chain length of the terminal alkene representative of larger full matrix of 144 precursors. Each of the 3 steps was conducted in solution employing acid/base extractions to isolate and purify the intermediates and final precursors providing the desired pure products ($\geq 95\%$) free of contaminants derived from unreacted starting materials, reagents, and reaction byproducts independent of the reaction yields. The final library construction was accomplished in a single reaction providing a mixture of 300 members/600 compounds and by 15 pairwise combinations (D1E1F1–4+D2 E1F1–4) providing 15 sub-libraries of 36 members/72 compounds containing two sets of homodimers as well as a defined set of heterodimers.

Library 2: Olefin Metathesis. In a complement to the first library, we have developed a second combinatorial library of C2-symmetric and unsymmetrical compounds with both the linkage and diversification of the linker domain created by use of the olefin metathesis reaction (FIG. 10). The precursors for our protypical library of 300 members (600 compounds including cis/trans isomers) were assembled from only 6 iminodiacetic acid diamides each functionalized with 4 w-alkene carboxylic acids. The precursors were assembled in a matrix 6×6×4 format with the 6 iminodiacetic acid diamides being prepared by parallel synthesis and with the last reaction conducted with a mixture of 4 w-alkene carboxylic acids (FIG. 11). As such, the 24 precursors were assembled in 3 parallel steps as 6 mixtures each containing 4 compounds with variations in only the chain length of the terminal alkene representative of larger full matrix of 144 precursors. Each of the 3 steps was conducted in solution employing acid/base extractions to isolate and purify the intermediates and final precursors providing the desired pure products ($\geq$95%) free of contaminants derived from unreacted starting materials, reagents, and reaction byproducts independent of the reaction yields. The final library construction was accomplished in a single reaction providing a mixture of 300 members/600 compounds and by 15 pairwise combinations (D1E1F1–4+D2 E1F1–4) providing 15 sub-libraries of 36 members/72 compounds containing two sets of homodimers as well as a defined set of heterodimers (FIG. 12). Finally, the 6 sub-libraries of homodimers containing 10 members/20 compounds were assembled in 6 reactions. Assay of the 6 homodimer sublibraries alongside the 15 homo/heterodimer sub-libraries was anticipated to minimize false positive/false negative responses especially since most of the diversification is simply in the length and olefin stereochemistry of the linking tether. This protocol also provides multisampling of the same compounds (each homodimer is generated in 5 of the 15 mixtures, indexed mixtures), and provides considerable deconvolution in a first pass assay. Final deconvolution of such mixtures by resynthesis of the individual components of the final precursors (last step) in the modest-sized 10- or 36-membered sub-libraries is straightforward. Moreover, the expansion of such a library to 60 iminodiacetic acid diamides constructed as detailed for library 1 followed by functionalization with a mixture of 4 w-alkene carboxylic acids and olefin metathesis linking and randomization of the tethering chain would produce a library of 28,920 members (57,840 compounds including cis/trans isomers) from 20 diversity units (6+10+4), FIGS. 10, 11 and 12.

Figure 14:
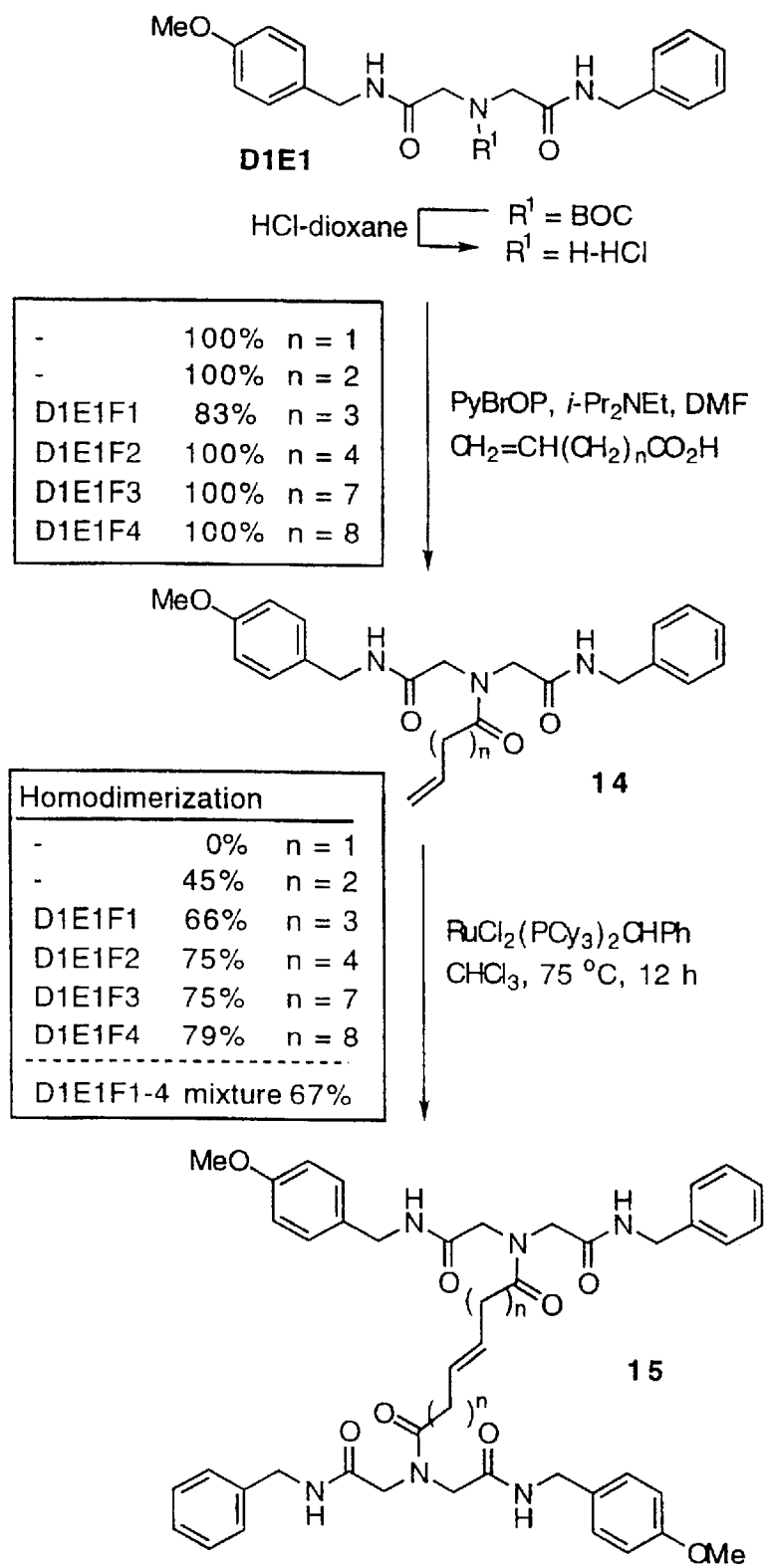
FIG. 14 illustrates that the individual coupling of the carboxylic acids F1–F4 with D1E1 revealed no perceptible rate or % conversion distinctions.

The parallel preparation of the 6 iminodiacetic acid diamides D1E1–D6E6 was accomplished in solution with acid/base extractions for isolation and purification as detailed for library 1. Analogous to the prior observations, the introduction of D1–D6 provided the monoamides 2 (76–100%, 90% avg) in pure form ($\geq$95%) and the subsequent introduction of E1–E6 to provide the diamides 3 proceeded in high yields (11–99%, 68% avg) with the exception of E5D5 (Table 3). Irrespective of the conversions, the materials isolated were of high purity (290–95%) and suitable for further use. Acidcatalyzed deprotection of 3 (1 equiv, 4 M HCl-dioxane, 25° C., 4 h) followed by coupling (1 equiv PyBrOP, 3 equiv i-Pr2NEt, DMF, 25° C., 16 h) with an equimolar mixture of F1–F4 (0.17 equiv each, 0.67 equiv total) cleanly provided the six pools of precursors 14 (68–25%, 50% avg, FIG. 13). Independent of the conversion and amount of recovered product, each of the 6 mixtures was isolated free of contaminant recovered starting materials, reagents and reagent-derived reaction byproducts by use of the acid (20% aqueous HCl/saturated NaCl) and base (saturated aqueous NaHCO3) extractive workup (290–95% pure). Although anticipated because of the structural similarities of the carboxylic acids in the F1–F4 mixture, the individual coupling of the carboxylic acids F1–F4 with D1E1 revealed no perceptible rate or % conversion distinctions (FIG. 14) and analysis (HRMS, 1H NMR) established the presence of each of the 4 expected compounds in the 6 mixtures. Nonetheless, in order to insure that different coupling rates might not skew the equimolar mixture, the final coupling reaction with the F1–F4 mixture (0.67 equiv) was conducted with excess secondary amine (1.0 equiv) and a prolonged reaction time (16 h) to guarantee complete consumption of the stoichiometry limiting carboxylic acid; FIGS. 13 and 14.

Prior to implementing the full and final library construction, the protocol for conducting the olefin metathesis reaction was developed on the individual members of the D1E1F1–F4 sub-library. Thus, the individual couplings of D1E1 with $CH_2=CH(CH_2)_nCO_2H$ (n=1, 2, 3, 4, 7, and 8) provided the corresponding w-alkene amides (83–100%, FIG. 14). Symmetrical homodimerization by olefin metathesis was most effectively accomplished by treatment with $RuCl_2(PCy_3)$ 2=CHPh26 (0.2–0.25 equiv, $CHCl_3$, reflux, 16 h) and cleanly afforded the homodimers for n=3,4,7, and 8, less effectively provided the homodimer for n=2, and failed to provide the desired product with n=1. The well behaved w-alkene carboxylic acids (n=3, 4, 7, and 8) were selected for use in the library generation. Both $RuCl_2(PCy_3)$ 2=CHPh and $RuCl_2(PCy_3)$ 2=CH—CH=CPh2 failed to produce comparable results when the reaction was conducted at 25° C. and the metathesis catalyst $Mo(C10H12)(C12H17N)[OC(CH_3)(CF_3)_2]_2$ proved too sensitive to use under the robust reaction conditions. Just as importantly, the homodimer metathesis products 15 proved to be chromatographically similar to one another and substantially different from the precursors 14 which in turn all behaved similarly. This additional and unanticipated bonus provided the opportunity to purify the final products, as mixtures, free from any potential starting materials. In our original design, the intention was to conduct the olefin metathesis reaction under conditions where all or essentially all 14 is consumed. However, the simple chromatographic separation of the homodimer and heterodimer metathesis products from the precursors 14 permitted an additional level of purity control without compromising the mixture integrity. This was also implemented in our final library preparation. The D1E1F1–F4 homodimer sub-library was constructed (67%) and characterized (1H NMR, MS). The MS spectrum exhibited the molecular ion peaks corresponding to each of the 10 components (20 compounds including cis/trans isomers) and the 1H NMR proved remarkably clear given the potential complexity of the mixture. Clear from these comparisons are the absence of the monomers in the metathesis dimer products as evidenced by the loss of the diagnostic vinyl signals and their replacement by disubstituted olefin signals and the remarkable clarity of the 1H NMR spectrum of the homodimer sub-library. Thus, although the similar properties of the individual components of the D1E1F1–4 homodimerization library precluded their separation/identification in the mixture by chromatographic means, 1H NMR and especially MS unambiguously established the presence of each of the individual components.

The assemblage of the full library of 600 compounds, the preparation of the complete set of 15 homo/heterodimer sublibraries, and the 6 homodimer libraries were conducted similarly (0.2–0.25 equiv $RuCl_2(PCy_3)$ 2=CHPh, $CHCl_3$, reflux, 16 h) providing the mixture libraries in 75–23% (50% average) following a chromatographic purification/enrichment to remove the metathesis catalyst, its reaction byproducts, and the small amount of remaining reacting monomers and/or their exchange products with the catalyst. The latter minor byproducts containing a terminating styrene proved chromatographically similar to the starting monomers and were readily removed during this chromatographic enrichment. This was employed for the prototypical library generation detailed herein but in practice is probably unnecessary. Assay of the precursor mixtures D1E1F1–4 along with the metathesis libraries would permit detection and identification of activity due to contaminant monomer precursors and that of any of the styrene-capped monomers which would be present only in minor amounts could be recognized and addressed upon resynthesis and deconvolution of the individual components of the small mixtures.

The solution-phase synthesis of two prototypical combinatorial libraries were detailed which were derived from the C2-symmetrical and unsymmetrical linkage of diversified monomers targeted for use in studying receptor and protein homodimerization and heterodimerization. In the first prototypical library, a 600 member combinatorial library of C2 symmetric ligands was prepared in 3 steps in a set of 60 sub-libraries of 10 compounds each by final dimerization linkage with a mixture of 10 rigid dicarboxylic acids. In each step of the 3-step sequence, multi-gram or multi-milligram amounts of pure intermediates and final products were isolated ($\geq 90\%$ pure) by simple acid/base extraction removal of reaction byproducts and unreacted starting materials. Notably, the direct final dimerization linkage of the immediate precursors to provide the C2-symmetric library would be precluded by solid-phase synthesis techniques making this solution-phase approach especially valuable for such symmetrical libraries. A second prototypical library which extends this approach was prepared employing a solution-phase olefin metathesis reaction to join and combinatorially randomize the length of the linking tether. This approach provides a unique solution to the rapid generation of a statistically controlled mixture of compounds that is especially well suited for establishing a required or optimal length of a linker within symmetrical or unsymmetrical dimer or oligomer libraries.

EXAMPLE 2

Multistep Convergent Solution-Phase Combinatorial Synthesis and Deletion Synthesis Deconvolution This example further discloses the first convergent, multistep library syntheses and does so by solution-phase mixture synthesis. Mixture synthesis is rarely used and rarely received well principally, because it cannot be conducted on the solid phase effectively. In addition, we disclose a new deconvolution protocol which is especially well suited for mixture libraries and, from a biologist's perspective, the more obvious way to test for activity or function (Deletion Synthesis Deconvolution). We do this with a library sized of (108). We understand all of the elements of library sizes and the ramifications it has on testing concentrations or competitive and interfering activity. However, we have selected these sizes for our exemplary libraries (108 and 106) to illustrate the power of the technique which no solid-phase technique can really approach. Finally, some may imply that this is not a "small molecule" library but rather a library of large and unrealistic molecules. This it not accurate when one realizes we are searching for agonists or antagonists of protein-protein interactions to serve the same function as a protein signaling molecule (i.e. erythopoetin as a protein) and elicit full agonist activity inducing receptor dimerization and activation. This cannot be accomplished with a conventional "small molecule."

The approach is illustrated employing the synthesis of iminodiacetic acid diamide libraries with a two-fold dimerization to convert the monomers first to dimers and then to tetramers incorporating eight variable groups (FIG. 17). We wish to emphasize that this strategy is not limited to iminodiacetic acid diamide libraries which themselves resemble peptides and that nonamide-based templates have been incorporated into analogous sequential dimerizations. The first dimerization is conducted with ω-alkene carboxamide derivatives of iminodiacetic acid which sets up the second dimerization to provide tetramers conducted with the olefin metathesis reaction. This latter reaction is conducted with a mixture of 4 ω-alkenes to join and randomize the linking tether length adding a ninth degree of diversification suited for simultaneously incorporating a linker of unknown optimal length. The mixture of 4 ω-alkenes (n=3, 4, 7, 8) provide 16 heterodimer or 10 homodimer metathesis products, each produced as a trans/cis mixture (2–4:1). Upon hydrogenation, this reduces to 9 chain lengths simplifying deconvolution.

The approach was first established with the individual preparations of A1B1C1–A1B1C4 and their sequential symmetrical dimerizations as shown in FIG. 17. With the conditions in hand, two libraries of 106 and 108 compounds were assembled in an analogous 4–5 steps enlisting only 10 or 20 amines (A1–A5/A1–A10 and B1–B5/B1–B10) and 4 ω-alkene carboxamide derivatives of N-BOC-iminodiacetic acid (C1–C4), FIG. 18 This can be conducted by mixture synthesis, mix and split synthesis, or by partial parallel/mixture synthesis with smaller pool sizes. However, given the ease with which positional scanning or deletion synthesis deconvolution can identify an active lead, the simpler process of mixture synthesis was used. Unlike solid-phase synthesis where the polymer-bound substrate typically must be the stoichiometry limiting reaction partner, either the substrate or the reacting attachment groups may be limiting in solution-phase chemistry. This dictates the use of mix and split synthesis for the solid-phase in order to accommodate differential reaction rates whereas the simpler protocol of mixture synthesis with limiting reagent stoichiometry (e.g., A1–A10) may be used in solution to insure all library members are generated. The implementation of the latter only requires the ability to remove unreacted starting substrate. Although not possible with solid-phase synthesis, this is accomplished by aqueous acid/base extractions in the first 3 steps of FIG. 17 which also serve to remove reagents and reagent byproducts.

The deconvolution of the 106 library, which may be tested under conditions providing realistic concentrations of the individual components, by positional scanning requires 5 sublibraries of A1BXCX . . . A5BXCX, 5 sublibraries of AXB1CX . . . AXB5CX, and 4 sublibraries of AXBXC1 . . . AXBXC4. They were prepared concurrent with the full library mixture requiring 14 additional mixture syntheses and, in principal, provides the lead identities in a single round of testing. As a complement, we have also introduced a protocol referred to as deletion synthesis deconvolution. It was conducted simultaneously by constructing 14 sublibrary mixtures, each lacking only one different member of the variable units and the libraries are screened for a loss versus gain in activity. The latter mixtures lack what the former mixtures contain and their combination reconstitute the full mixture.

Preliminary efforts suggest that the two methods are complementary and that deletion synthesis is more sensitive to establishing the most active lead in a library that contains few hits albeit at the expense of identifying weaker leads whereas positional scanning is more effective at identifying the weaker leads especially in libraries with multiple hits but at the expense of accurately identifying the most potent agent (Freier et al. J. Med. Chem. 1995, 38, 344; Konings et al. J. Med. Chem. 1997, 40, 4386). The implementation of either, or better both, in conjunction with the solution-phase preparation of library mixtures provides a powerful approach to lead discovery that permits the rapid preparation and screening of large numbers of compounds. The combined use of solution-phase mixture synthesis and the two deconvolution protocols is simple and technically nondemanding even for large compound libraries, applicable to convergent as well as linear divergent syntheses, less demanding than solid-phase mix and split syntheses or tagging, and unlike iterative, SURF or recursive deconvolution, can be conducted up front for depository libraries subjected to multiple screening.

EXAMPLE 3

Solution-phase Combinatorial Synthesis:
Convergent Multiplication of Diversity Via the
Olefin Metathesis Reaction In this example, the solution-phase synthesis of iminodiacetic acid diamides functionalized with ω-alkenes and their dimerization via the olefin metathesis reaction in the preparation of mixture libraries are detailed. Libraries containing as many as 113,232 compounds prepared from only N-BOC-iminodiacetic acid anhydride (1), 15 amines, and 4 ω-alkene carboxylic acids illustrate the diversity that may be achieved by a convergent versus divergent combination of a small number of monomer building blocks that provides the multiplication of diversity typically associated with linear library syntheses including peptides, oligonucleotides and sequential template functionalizations. Unlike the divergent synthesis of such libraries which is amenable to solid-phase synthesis techniques, the convergent synthesis is especially well suited for solution-phase synthesis and is precluded by solid-phase techniques since the combining components typically would be on mutually exclusive phases.

Combinatorial chemistry, initially pursued with peptide and oligonucleotide libraries, has undergone rapid development providing a new paradigm for drug discovery. Perhaps as a consequence of the extension from linear peptide and oligonucleotide synthesis, the majority of applications have relied on linear solid-phase synthesis and methodological advances continue to extend common synthetic transformations to polymer-supported versions. A less commonly employed complement is the development of protocols for solution-phase combinatorial synthesis. Preceding the disclosure of our own efforts on the development of a multistep solution-phase parallel synthesis of chemical libraries (Cheng et al. J. Am. Chem. Soc. 1996, 118, 2567; Boger et al. J. Am. Chem. Soc. 1996, 118, 2109; Cheng et al. Bioorg. Med. Chem. 1996, 4, 727; Tarby et al. In Molecular Diversity and Combinatorial Chemistry: Libraries and Drug Discovery Chaiken, I. M., Janda, K. D., Eds.; ACS: Washington, 1996;81) the single step solution-phase synthesis of mixture libraries was detailed by at least three groups (Carell et al. Angew. Chem., Int. Ed. Engl. 1994, 33, 2059; Smith et al. Bioorg. Med. Chem. Lett. 1994, 4, 2821; Pirrung et al. J. Am. Chem. Soc. 1995, 117, 1240).

Our efforts focused on the development of a technically non-demanding multistep, solution-phase strategy for the preparation of chemical libraries which relied on the removal of excess reactants and reagents by liquid-liquid or liquid-solid extractions. The approach was shown to dependably deliver pure individual compounds in large quantities (50–150 mg), and libraries of >1000 individual members were assembled in initial efforts. It has been since implemented on scales producing 50–150 mg of the final materials in formats for the parallel synthesis of individual pure compounds, for modest sized libraries composed of small mixtures 24 (1000–10,000 member libraries, 10–100 compounds/mixture), or combinatorially assembled to provide larger compound libraries (25,000–100,000 member libraries, 10–28,000 compounds/mixture) allowing its compatibility with any screening objective or protocol. Since the libraries are produced on a relatively large scale, they may be repeatedly dispensed for routine screening without depletion of the growing collection. These features along with its technically non-demanding implementation are among its greatest attributes.

In example 1, we disclosed its extension to the preparation of modest sized libraries suitable for probing protein-protein interactions. This entailed the dimerization linkage of iminodiacetic acid diamides using either symmetrical dicarboxylic acids or the olefin metathesis reaction to join and combinatorially randomize the length of a linking tether (FIG. 1). Herein, we provide details of this latter approach, its extension to higher order libraries, and its use in the generation of large combinatorial libraries enlisting a convergent versus divergent approach to the factorial multiplication of the diversity. Unlike the linear divergent synthesis of libraries which is suited for solid-phase synthesis, the convergent synthesis is especially well suited for solution-phase synthesis and would be precluded by solid-phase techniques where the combining components are on mutually exclusive solid-phases.

Developmental Studies. Initial efforts focused on the preparation of a modest sized library to illustrate the approach. It constitutes the dimerization and simultaneous randomization of the length of a linking tether joining two iminodiacetic acid diamides employing the olefin metathesis reaction as described above. The reaction sequence requires 4 steps and represents an extension of our solution-phase synthesis of chemical libraries that is especially well suited for establishing an unknown linker length. In addition to the advantages outlined above, the solution-phase synthesis of the fragments and their convergent linkage would be precluded by conventional solid-phase synthesis techniques.

The precursors for the protypical library of 300 members (600 compounds including cis/trans isomers) were assembled from 6 iminodiacetic acid diamides each functionalized with 4 ω-alkene carboxylic acids, FIG. 10. The precursors were assembled in a matrix 6×6×4 format and only the diagonal 6 iminodiacetic acid diamides were prepared by parallel synthesis and the last reaction was conducted with a mixture of 4 ω-alkene carboxylic acids. As such, the 24 precursors 4 were assembled in 3 parallel steps as 6 mixtures each containing 4 compounds with variations in only the chain length of the terminal alkene. For the development studies, the selection of the matrix diagonal DXEX combination represented in FIG. 13 was simply a matter of convenience. Each of the 3 steps was conducted in solution employing acid/base extractions to isolate and purify the intermediates providing the desired pure products ($\geq 95\%$ pure) free of contaminants derived from unreacted starting materials, reagents, and reaction byproducts independent of the reaction yields (FIG. 13). To insure that different coupling rates might not affect the equimolar mixture, the final coupling step of the reaction sequence to produce 14 was conducted with excess 3 (1.5 equiv) for a prolonged reaction time (16 h) to guarantee complete consumption of the stoichiometry limiting carboxylic acid (F1–F4).

Figure 16:
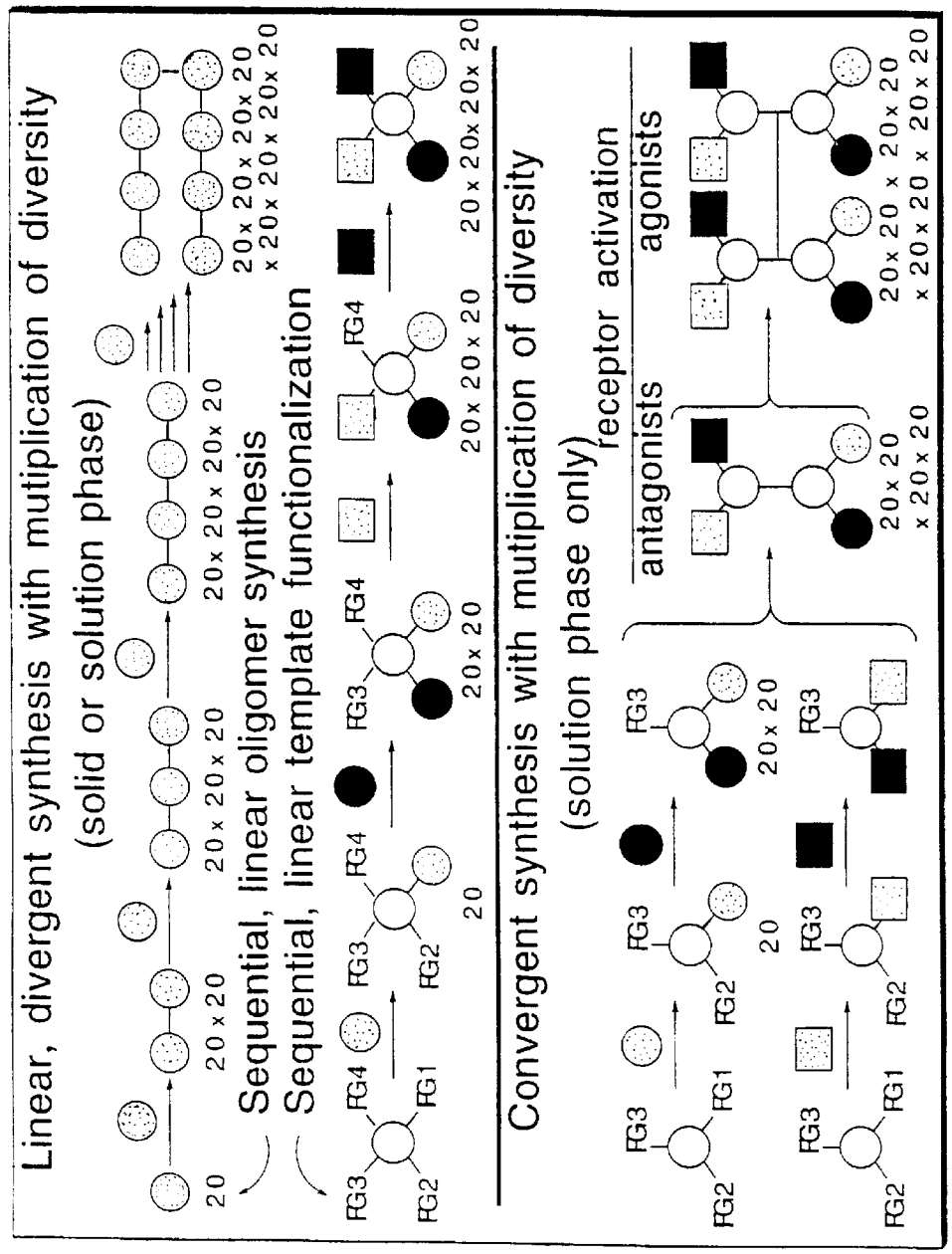
FIG. 16 illustrates both linear, divergent synthesis with multiplication of diversity strategy or convergent synthesis with multiplication of diversity combinatorial strategies.

Prior to implementing the library construction, the protocol for conducting the olefin metathesis reaction was examined with the individual members of the D1E1F1–F4 sublibrary. The couplings of D1E1 with CH2=CH(CH2)

nCO2H (n=1, 2, 3, 4, 7, and 8) provided the corresponding ω-alkene amides (83–100%, FIG. 14). Symmetrical homodimerization of 14 by olefin metathesis was accomplished by treatment with RuCl2(PCy3) 2=CHPh (0.2–0.25 equiv, CHCl3, reflux, 16 h) and cleanly afforded the homodimers 15 for n=3, 4, 7, and 8, but worked less effectively for n=2, and failed to provide the desired product with n=1. A mixture of trans and cis double bond isomers was observed (2.2–3.2:1) and although the trans isomer predominated, both isomers were produced in significant amounts. Both RuCl2(PCy3) 2=CHPh and RuCl2(PCy3) 2=CH—CH=CPh2 failed to produce comparable results when the reaction was conducted at 25° C. and Mo(C10H12)(C12 H17N) [OC(CH3)(CF3) 2]$_2$ proved too sensitive under the robust reaction conditions. Typically, complete reaction required 0.15–0.25 equiv of the catalyst RuCl2(PCy3) 2=CHPh and a summary of a study with n=7 is provided in FIG. 14. The D1E1F1–F4 homodimer sublibrary was constructed (67%) similarly and characterized (1H NMR, MS). The mass spectrum exhibited the molecular ion peaks corresponding to each of the 10 components and the 1H NMR spectrum proved remarkably clear given the potential complexity of the mixture (FIG. 16). Clear from these comparisons is the absence of the monomers in the metathesis dimer products as evidenced by the loss of the diagnostic vinyl signals and their replacement by disubstituted olefin signals.

Figure 22:
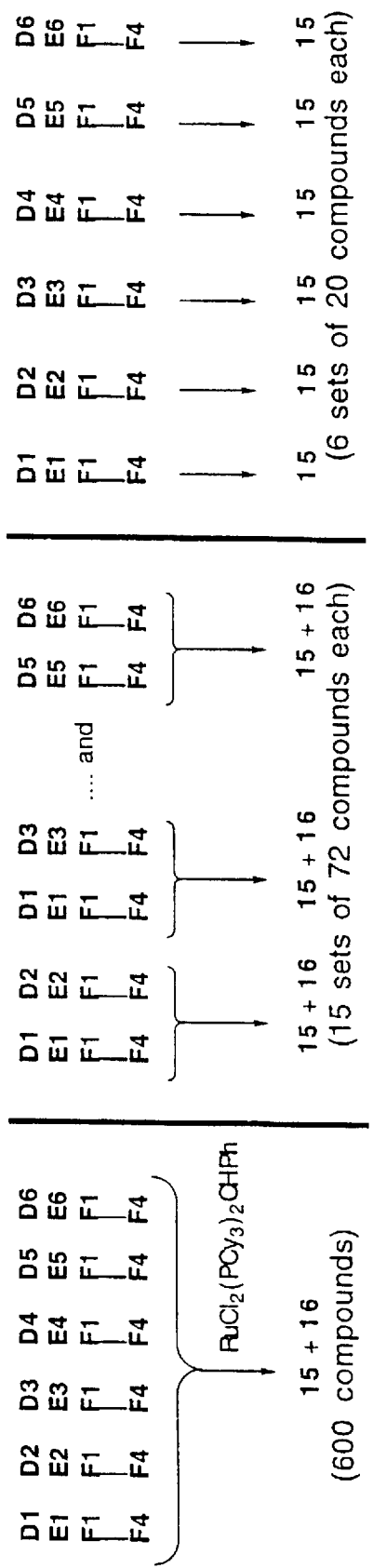
FIG. 22 illustrates that the library of compounds 15 and 16 construction was accomplished in a single reaction providing a mixture of 600 compounds and by 15 pair-wise combinations (D1E1F1–4+D2 E2 F1–4) providing 15 sub-libraries of 72 compounds containing two sets of homodimers (15) as well as a defined set of heterodimers (16).

The library of compounds 15 and 16 construction was accomplished in a single reaction providing a mixture of 600 compounds and by 15 pair-wise combinations (D1E1F1–4+ D2E2F1–4) providing 15 sublibraries of 72 compounds containing two sets of homodimers (15) as well as a defined set of heterodimers (16) (FIG. 22). Finally, the 6 sublibraries of homodimers containing 20 compounds were assembled in 6 reactions. There was no special significance to this choice of combinations except that each represents a significantly different mixture pool size which can be chosen to accomodate preferences in testing and deconvolution protocols. However, given the ease of conducting the modest number of reactions to generate all three, this protocol does provide a first level deconvolution as well as a multisampling of the same compounds since each homodimer is additionally generated in 5 of the 15 mixtures (indexed mixtures). This provides the opportunity for considerable deconvolution in a first pass assay. Final deconvolution of such mixtures by resynthesis from the individual components of the final precursors (last step) in the modest-sized 20- or 72-membered sub-libraries is straightforward. This can be further simplified by hydrogenation of the final library mixtures to provide products containing the saturated hydrocarbon linking chain.

The assemblage of the library of 600 compounds, the 15 homo/heterodimer sublibraries, and the 6 homodimer libraries was conducted (0.2–0.25 equiv RuCl2(PCy3) 2=CHPh, CHCl3, reflux, 16 h) providing the mixture libraries in 75–23% (50% average, FIG. 15). The diner metathesis products 15 and 16 proved to be chromatographically similar to one another and substantially different from the precursors 14, which in turn behaved similarly. This additional and unanticipated observation provided the opportunity to purify the final products as mixtures, free from any potential starting materials. In our original design, the intention was to conduct the olefin metathesis reaction under conditions where essentially all 4 was consumed. While this proved to be the case, the simple chromatographic separation of the metathesis products from the precursors 4 permitted an additional level of purity control without compromising the mixture integrity. This chromatographic purification was used to remove the metathesis catalyst, its reaction byproducts, any trace amount of remaining reacting monomers and their exchange products with the catalyst. The latter minor byproducts containing a terminating styrene derived from the catalyst proved chromatographically similar to the starting monomers and were readily removed during the chromatographic enrichment. This was employed for the prototypical library generation detailed herein but in practice is unnecessary. Assay of the precursor mixtures DXEXF1–4 along with the metathesis libraries permits detection of activity due to monomer precursors and that of the styrene-capped monomers could be recognized and addressed upon resynthesis and deconvolution of the the small mixtures.

A Dimer Library. Following the initial studies, the extension of this work to the preparation of full matrix libraries was conducted. The results of a representative library are summarized in FIG. 23 using an expanded version of the library illustrated in FIG. 1 further incorporating Na-CBZ-lysine methyl ester (D7) since it emerged from initial screening efforts as a key substituent. To complement rather than simply repeat the initial library, it was also conducted with an altered set of 4 ω-alkene carboxylic acids (n=2, 4, 7, and 9 for C1–C4).

The library precursors were prepared as outlined in FIG. 1 providing the functionalized iminodiacetic acid diamides in 3 steps with average yields of 88% (step 1), 89% (step 2), and 65% (step 3). Olefin metathesis homodimerization of each of the 42 iminodiacetic acid diamides functionalized with the 4 ω-alkenes (n=2, 4, 7, 9) provided a library of 840 compounds in a format of 42 mixtures of 20 compounds. In addition, the combinatorial synthesis of the full homo- and heterodimer library consisting of 28,492 compounds was also accomplished in a single step employing an equimolar mixture of the 42 starting materials. Notably, this large compound mixture arises from the use of only 1, 13 amines, and 4 ω-alkene carboxylic acids statistically combined in all homo- and heterodimerization combinations by the olefin metathesis reaction providing a convergent factorial multiplication of the diversity. Although analogous to the simple multiplication of diversity one achieves in a linear, divergent library synthesis (e.g., repetitive peptide couplings of 20 amino acids), the convergent synthesis also provides the advanced intermediates in a form that permits incorporation from library to library.

This mixture could be generated even more simply in a total of 4 steps by using modestly sized mixtures of reactants at each of the first three steps of the four step synthesis: 7 amines in step 1, 6 amines in step 2, and 4 w-alkene carboxylic acids in step 3.

Figure 24A:
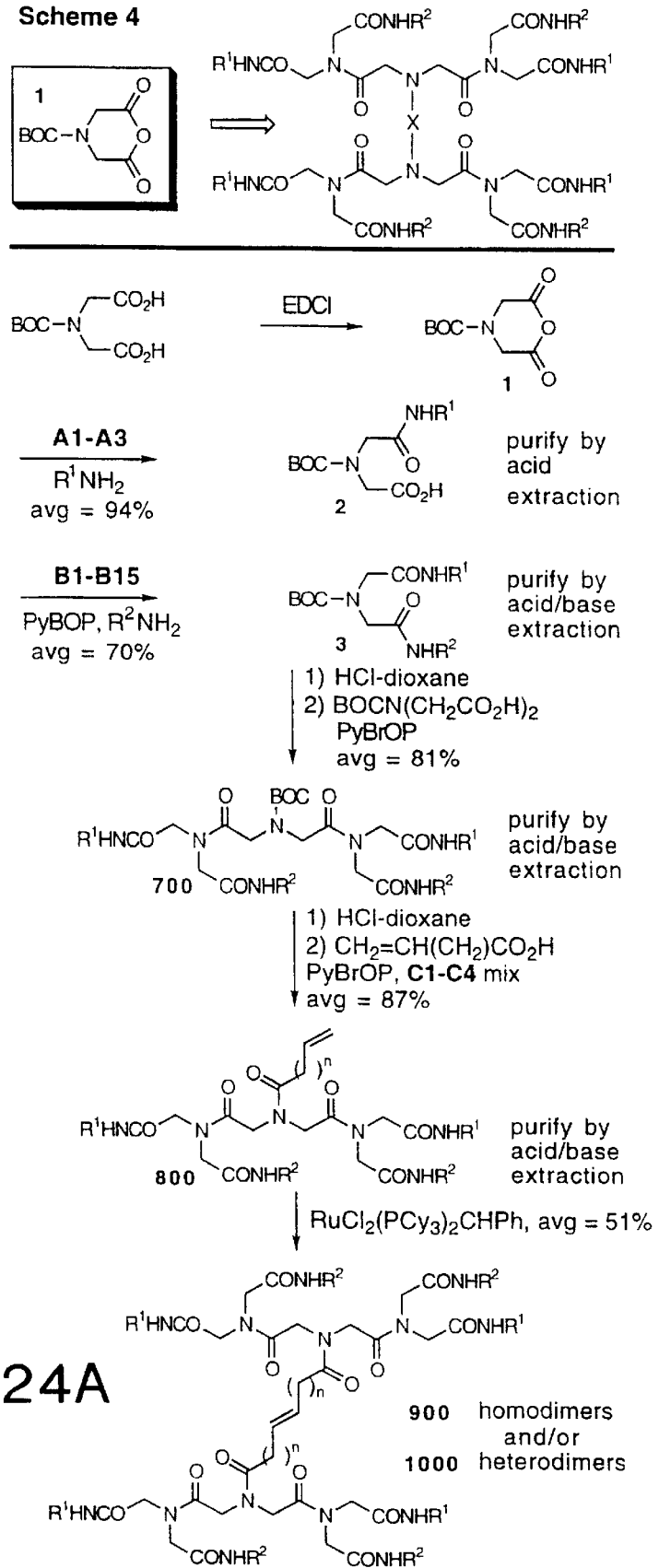
FIG. 24 illustrates a convergent versus linear protocol that provides tetramers versus dimers of the iminodiacetic acid diamides. The approach entails the further one-step dimerization to 700 of the iminodiacetic acid diamides with N-BOC-iminodiacetic acid followed by N-BOC deprotection, functionalization with w-alkene carboxylic acids to provide 800, and subsequent olefin metathesis for further dimerization (900/1000) with randomization of the length of the linking chain.
Figure 24B:
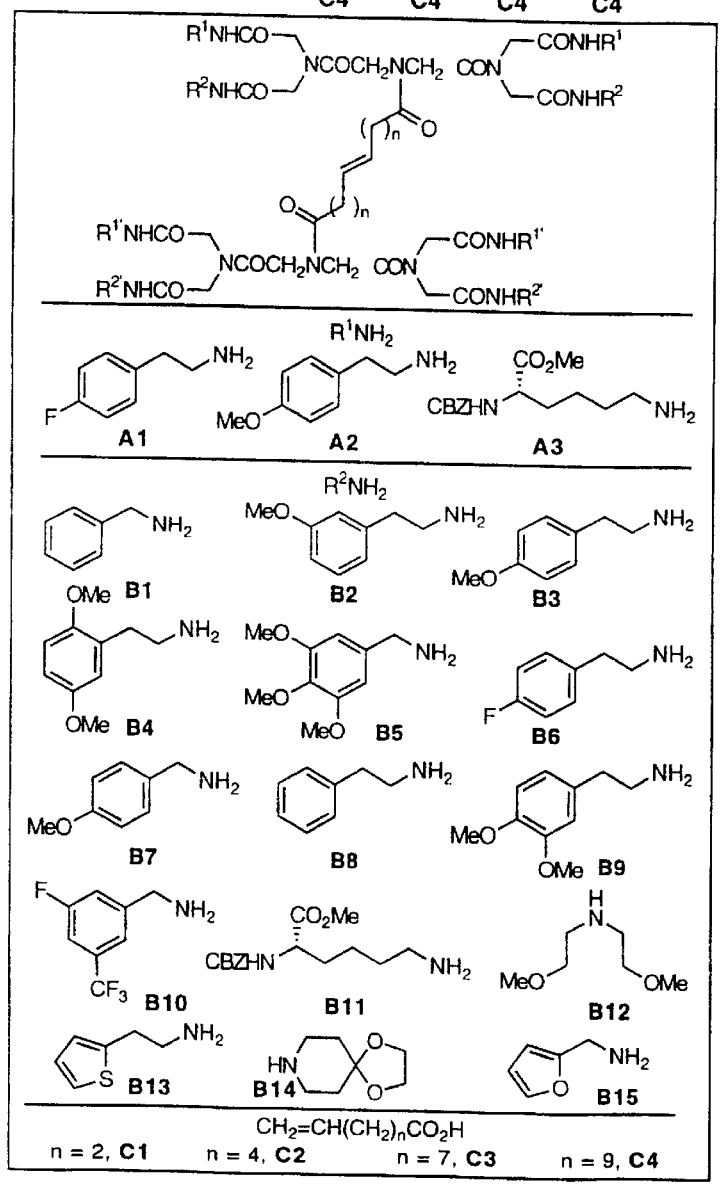

Higher Order Libraries. Given the size of the endogenous protein ligands and hormones that promote receptor dimerization, the knowledge that many (e.g., PDGF, CSF-1, SCF) act not as monomers but as dimers in their own right, and the large size of the ligand binding pocket formed upon receptor dimerization created by discontinuous domains of the proteins, the simple dimerization of the iminodiacetic acid diamides may only provide antagonists of ligand binding and be of insufficient size to serve as agonists for receptor activation. Given that endogenous ligands themselves are quite large and bind on the cell surface via the extracellular domains of the receptors, larger or higher order structures based on the iminodiacetic acid diamides often may be better suited as potential agonists. Provided they are synthetically readily accessible, such candidate synthetic agonists may prove acceptable since they need not be permeable to the cell for effective activity. In our efforts, we have examined a convergent versus linear protocol that provides tetramers versus dimers of the iminodiacetic acid diamides (FIG. 24).

The approach entails the further one-step dimerization to 700 of the iminodiacetic acid diamides with N-BOC-iminodiacetic acid followed by N-BOC deprotection, functionalization with ω-alkene carboxylic acids to provide 800, and subsequent olefin metathesis for further dimerization (900/1000) with randomization of the length of the linking chain. The results obtained in the first library assembled in this manner are summarized in FIG. 24 and FIG. 25. For reasons related to screening results, the library was assembled in a 3×15×4 format providing 42 iminodiacetic acid diamides 3, each of which contained one of the three best side chains. These were dimerized in a single step upon treatment with 4 M HCl-dioxane (25° C., 4 h) followed by coupling with N-BOC-iminodiacetic acid (0.33 equiv, 1 equiv PyBrOP, 3 equiv i-Pr2NEt, DMF, 25° C., 16 h, avg yield=81%) to provide 700, an interesting class of iminodiacetic acid diamide dimers for screening in their own right. Subsequent N-BOC deprotection (4 M HCl-dioxane, 25° C., 4 h) and coupling with 4 ω-alkene carboxylic acids (0.67 equiv, 1 equiv PyBrOP, 3 equiv i-Pr2NEt, DMF, 25° C., 16 h, avg yield=87%) provided the olefin metathesis precursors 800. Olefin metathesis homodimerization to 900 (0.2 equiv RuCl2(PCy3) 2CHPh, CHCl3, reflux, 16 h, avg yield=51%) of each of the 42 linked iminodiacetic acid diamides functionalized with the 4 ω-alkenes (n=2, 4, 7, 9) provided a library of 840 compounds in a format of 42 mixtures of 20 compounds. The full homo- and heterodimer library (900/1000) consisting of 28,392 compounds was prepared in a single step employing an equimolar mixture of the 42 starting materials.

The statistical combination of the precursors 700 with the simultaneous variation in the linking chain length to provide the large library required only N-BOC-iminodiacetic acid, 15 amines, and 4 ω-alkene carboxylic acids as starting materials.

Figure 26:
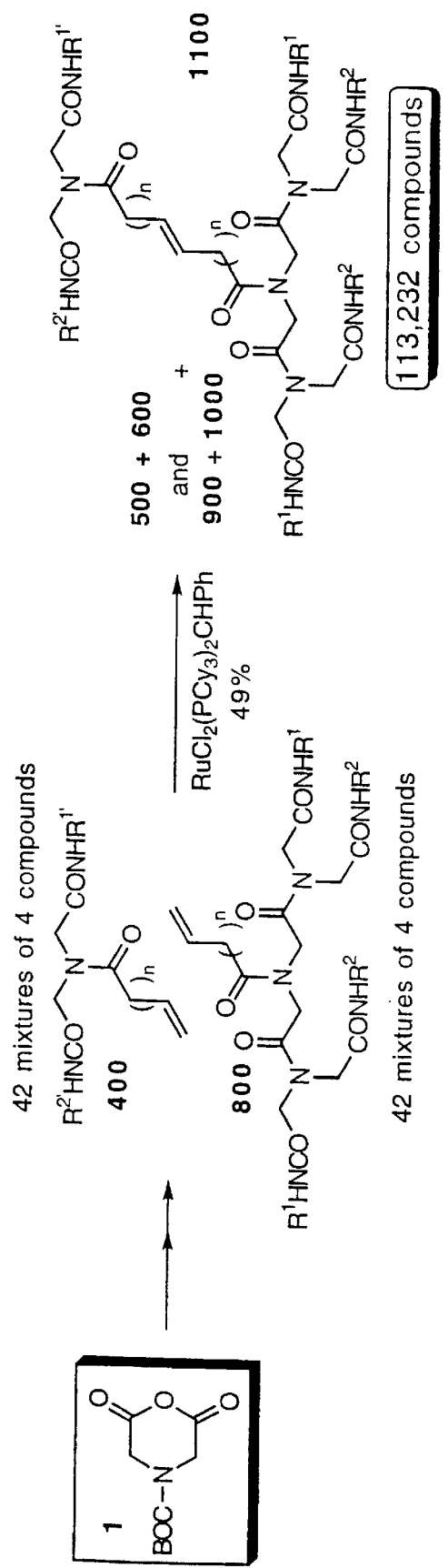
FIG. 26 highlights the advantages of the modular convergent construction of the libraries that accompanies the olefin metathesis linkage of the individual monomers, an equimolar mixture of the 42 iminodiacetic acid diamides 4 bearing the 4 ω-alkenes from the initial dimer library and the analogous 42 precursors 800 from the second tetramer library were combined in a single reaction (0.2 equiv cat., CHCl3, reflux, 16 h, 49%) to provide an even larger library of 113,232 compounds composed of all members of the two initial libraries plus all cross metathesis reaction products incorporating 3 versus 2 or 4 iminodiacetic acid diamides.

In a reaction that highlights beautifully the advantages of the modular convergent construction of the libraries that accompanies the olefin metathesis linkage of the individual monomers, an equimolar mixture of the 42 iminodiacetic acid diamides 4 bearing the 4 ω-alkenes from the initial dimer library and the analogous 42 precursors 8 from the second tetramer library were combined in a single reaction (0.2 equiv cat., CHCl3, reflux, 16 h, 49%) to provide an even larger library of 113,232 compounds composed of all members of the two initial libraries plus all cross metathesis reaction products incorporating 3 versus 2 or 4 iminodiacetic acid diamides (FIG. 26). This convergent library construction employed only 1, 15 different amines, and 4 ω-alkene carboxylic acids.

Conclusions. The solution-phase synthesis of prototypical libraries for use in studying receptor and protein homodimerization and heterodimerization were detailed which were derived from the olefin metathesis linkage of iminodiacetic acid diamide monomers. The iminodiacetic acid diamide derived monomers may be screened in advance as well as alongside the dimer libraries for simple binding and antagonist activity. This further simplifies the extension of the studies to the discovery of agonists where the subsequent homodimer products constitute those potentially suited as agonists of protein homodimerization while the heterodimer products constitute those potentially suited as agonists for dimerization of two different proteins. The convergent dimerization linkage of the immediate precursors to provide the libraries would be precluded by solid-phase synthesis techniques making the solution-phase approach especially valuable.

In addition, the use of the olefin metathesis reaction to join and randomize the length of the linking tether provides a direct solution to the rapid generation of a statistically controlled mixture of compounds that is especially well suited for establishing a required linker length within dimer or oligomer libraries. Most importantly, it highlights the use of a convergent synthetic approach to library synthesis that embodies a factorial versus simple multiplication of diversity characteristic of a linear divergent synthesis necessarily employed with solid-phase libraries.

Synthetic Protocals

All reactions were carried out under an argon atmosphere with dry, freshly distilled solvents under anhydrous conditions, unless otherwise noted. Tetrahydrofuran (THF), toluene and ethyl ether (ether) were distilled from sodium-benzophenone, and methylene chloride (Methylene chloride), from calcium hydride. Anhydrous solvents were also obtained by passing them through commercially available alumina column. Yields refer to chromatographically and spectroscopically ($^1$H NMR) homogeneous materials, unless otherwise stated. Reagents were purchased at highest commercial quality and used without further purification unless otherwise stated. Reactions were monitored by thin layer chromatography carried out on 0.25 mm E. Merck silica gel plates (60F-254) using UV light as visualizing agent and 7% ethanolic phosphomolybdic acid or p-anisaldehyde solution and heat as developing agents. E. Merck silica gel (60, particle size 0.040–0.063 mm) was used for flash column chromatography. Preparative thin-layer chromatography (PTLC) separations were carried out on 0.25, 0.50 or 1 mm E. Merck silica gel plates (60F-254). NMR spectra were recorded on Brucker AMX-600 or AMX-500 instruments and calibrated using residual undeuterated solvent as an internal reference. The following abbreviations were used to explain the multiplicities: s=singlet, d=doublet, t=triplet, q=quartet, m=multiplet, b=broad. IR spectra were recorded on a Perkin-Elmer 1600 series FT-IR spectrometer. Optical rotations were recorded on a Perkin-Elmer 241 polarimeter. High resolution mass spectra (HRMS) were recorded on a VG ZAB-ZSE mass spectrometer under fast atom bombardment (FAB) conditions with NBA as the matrix. Melting points (mp) are uncorrected and were recorded on a Thomas Hoover Unimelt capillary melting point apparatus.

Variations of Amines and Diacid Libraries Which are Used With the Convergent Combinatorial Methodology.

The libraries of diacids and amines disclosed in FIGS. 1–26 have been chosen to best describe the invention. While a preferred form of the invention has been shown using these libraries, in the drawings and the following 3 examples, variations in the preferred form will be apparent to those skilled in the art, and therefore, the invention should not be construed as limited to these specific libraries of diacids and amines shown and described, but instead, is as set forth in the claims.

It should be noted that the invention works best with primary and secondary amines. When using the olefin metathesis conjugation method, one should take note not to include an amine having an olefin functionality, otherwise, side reactions will occur. Likewise, when using the diacid conjugation method, one should not choose an amine having free competing free acid functionalities, reactive alcohols (must be protected) or other side group unprotected amines (must be protected) which will react indiscriminately with the acid group. The diacids chosen must contain at least one carbon separating the two carboxyl carbons of the acid moiety to confer stability for conjugation.

SYNTHETIC PROTOCALS FOR EXAMPLE 1 (ILLUSTRATED IN FIGS. 1–15

Synthesis of N-((tert-Butyloxy)carbonyl)iminodiacetic Acid. A 1-L flask was charged with iminodiacetic acid (13.3 g, 100 mmol), dioxane (200 mL) and NaOH (8 g, 200 mmol) dissolved in 200 mL of water. When a homogeneous solution had formed, di-tert-butyldicarbonate (25 mL, 110 mmol) was added in portions. After stirring at 25° C. for 72 h, the reaction mixture was washed with Et2O (2 to 100 mL) and the aqueous layer was then acidified with the addition of 10% aqueous HCl (100 mL). This was extracted with EtOAc (3 to 150 mL) and the combined organic layers were washed with saturated aqueous NaCl (2 to 150 mL), and dried (Na2SO4). Concentration provided 30 g of a colorless oil, which upon addition of 30 mL of EtOAc followed by 60 mL of hexane afforded 17.2 g (74%) of the title compound as colorless crystals: mp 135–137° C.

General Procedure for the First Diversification for Library 1 and 2 (A1–A6 and D1–D6): N-((tert-Butyloxy)carbonyl)-N'-(2-(4-methoxyphenyl)ethyl) iminodiacetic Acid Monoamide (A2 and D3) as shown in FIGS. 2 and 10 (First 2 steps)

Method A: A mixture of N-((tert-butyloxy)carbonyl) iminodiacetic acid (4.66 g, 20 mmol) and EDCI (3.8 g, 20 mmol) in 60 mL of anhydrous DMF was stirred for 1 h at 25° C. 4-Methoxyphenethyl amine (A2, 3.0 g, 20 mmol; any other primary or secondary amine can be substituted as long as reactive side groups are protected, eg. alcohols protected as TBS, alkyl, benzyl; acids protected as esters/amides; etc) was added to the resulting solution in four portions (slightly exothermic). The reaction mixture was stirred for 20 h at 25° C. before it was poured into 250 mL of 10% aqueous HCl in a separatory funnel. The product was extracted into EtAOc (3 to 200 mL) and the combined organic phases were washed with 10% aqueous HCl (2 to 200 mL), saturated aqueous NaCl (2 to 200 mL), dried (Na2SO4) and the solvent removed in vacuo to afford 7.3 g (99%) of the title compound as a white solid: Rf=0.6 (10% HOAc-EtOAc); 1H NMR (DMSO-d6, 500 MHz) d 8.27 (m, 1H), 7.12 (m, 2H), 6.84 (m, 2H), 3.91, 3.87, 3.83 and 3.80 (four s, 4H), 3.70 (s, 3H), 3.25 (m, 2H), 2.64 (m, 2H), 1.35 and 1.32 (two s, 9H); IR (film) vmax 2976, 2931, 1705, 1635, 1513, 1456, 1393, 1368, 1248, 1164, 1032, 824, 600 cm−1; FABHRMS (NBA-NaI) m/z 367.1862 (M+H+, C18H26N2O6 requires 367.1869).

Method B: A solution of N-((tert-butyloxy)carbonyl) iminodiacetic acid (0.058 g, 0.25 mmol) dissolved in DMF (5 mL) was added to polymer-bound EDCI (0.5 g, 0.5 mmol/g, 0.25 mmol; Desai, M. C.; Stramiello, L. M. S. Tetrahedron Lett. 1993, 34, 7685). This mixture was allowed to stand for 1 h at 25° C. Tyramine (A3, 0.041 g, 0.30 mmol; generally any other primary or secondary amine can be substituted as long as reactive side groups are protected, eg. alcohols protected as TBS, alkyl, benzyl; acids protected as esters; etc was added and the mixture was allowed to stand for 20 h. After filtration, the resin was washed with DMF (5 mL) and EtOAc (50 mL). The combined organic phases were washed with 10% aqueous HCl (2 to 25 mL) and saturated aqueous NaCl (2 to 50 mL), dried (Na2SO4) and concentrated to afford 0.060 g (68%) of A3 identical to that prepared with solution-phase EDCI.

Data for N-((tert-Butyloxy)carbonyl)-N'-(2-(phenyl) ethyl)iminodiacetic Acid Monoamide (A1): Synthesized exactly as described in the general procedure using the appropriate amines shown in FIG. 5. 1H NMR (DMSO-d6, 500 MHz) d 8.29 (m, 1H), 7.27 (m, 5H), 3.90, 3.86, 3.83 and 3.80 (four s, 4H), 3.33 (m, 2H), 2.73 (m, 2H), 1.35 and 1.33 (two s, 9H); IR (film) vmax 3291, 2977, 2931, 1700, 1653, 1635, 1559, 1509, 1497, 1456, 1394, 1368, 1251, 1163, 1141, 857, 750, 700 cm−1; FABHRMS (NBA-NaI) m/z 337.1769 (M+H+, C17H24N2O5 requires 337.1763).

Data for N-((tert-Butyloxy)carbonyl)-N'-(2-(4-hydroxyphonyl)ethyl)iminodiacetic Acid Monoamide (A3): Synthesized exactly as described in the general procedure using the appropriate amines shown in FIG. 5. 1H NMR (DMSO-d6, 500 MHz) d 9.19 (d, 1H, J=3.8 Hz), 8.26 (m, 1H), 6.99 (d, 2H, J=6.0 Hz), 6.66 (d, 2H, J=5.7 Hz), 3.91, 3.87, 3.83 and 3.80 (four s, 4H), 3.22 (m, 2H), 2.60 (m, 2H), 1.35 and 1.33 (two s); IR (film) vmax 3406, 1653, 1559, 1540, 1517, 1457, 1250, 1049, 1025, 1001, 826, 765 cm−1; FABHRMS (NBA-NaI) m/z 353.1719 (M+H+, C17H24N2O6 requires 353.1713).

Data for N-((tert-Butyloxy)carbonyl)-N'-(2-(3-methoxyphenyl)ethyl)iminodiacetic Acid Monoamide (A4 and D2): Synthesized exactly as described in the general procedure using the appropriate amines shown in FIG. 5. 1H NMR (DMSO-d6, 500 MHz) d 8.26 (m, 1H), 7.19 (m, 1H), 6.76 (m, 3H), 3.90, 3.87, 3.84 and 3.81 (four s, 4H), 3.73 (s, 3H), 3.32 (m, 2H), 2.69 (q, 2H, J=10 Hz), 1.35 and 1.32 (two s, 9H); IR (film) vmax 3853, 3744, 3675, 3648, 3294, 2976, 1700, 1653, 1635, 1584, 1559, 1506, 1490, 1457, 1394, 1368, 1259, 1165, 1038, 963, 877, 781, 697 cm−1; FABHRMS (NBA-NaI) m/z 367.1860 (M+H+, C18H26N2O6 requires 367.1869).

Data for N-((tert-Butyloxy)carbonyl)-N'-(4-methoxybenzyl)iminodiacetic Acid Monoamide (A5): Synthesized exactly as described in the general procedure using the appropriate amines shown in FIG. 5. 1H NMR (DMSO-d6, 500 MHz) d 8.64 (m, 1H), 7.19 (m, 2H), 6.87 (m, 2H), 4.23 (d, 2H, J=5.8 Hz), 3.94, 3.92, 3.89 and 3.86 (four s, 4H), 3.72 (s, 3H), 1.35 and 1.29 (two s, 9H); IR (film) vmax 3406, 2978, 2530, 1700, 1653, 1559, 1514, 1457, 1394, 1368, 1302, 1250, 1165, 1142, 1048, 1026, 998, 908, 827, 766 cm−1; FABHRMS (NBA-NaI) m/z 353.1720 (M+H+, C17H24N2O6 requires 353.1713).

Data for N-((tert-Butyloxy) carbonyl)-N'-(2-(4-fluorophenyl)ethyl)iminodiacetic Acid Monoamide (A6 and D6): Synthesized exactly as described in the general procedure using the appropriate amines shown in FIG. 5. 1H NMR (DMSO-d6, 500 MHz) d 8.23 (m, 1H), 7.24 (m, 2H), 7.09 (m, 2H), 3.89, 3.86, 3.82 and 3.80 (four s, 4H), 3.30 (m, 2H), 2.71 (m, 2H), 1.35 and 1.32 (two s, 9H); IR (film) vmax 3852, 3744, 3675, 3648, 3295, 2978, 1700, 1684, 1653, 1635, 1559, 1540, 1510, 1457, 1394, 1368, 1222, 1161, 896, 772 cm−1; FABHRMS (NBA-NaI) m/z 355.1661 (M+H+, C17H23N2O5 requires 355.1669).

Data for N-((tert-Butyloxy)carbonyl)-N'-(benzyl)iminodiacetic Acid Monoamide (D1): Synthesized exactly as described in the general procedure using the appropriate amines shown in FIG. 5. 1H NMR (CDCl3, 500 MHz) 8.03 and 7.13 (two s, 1H, NH), 7.27 (m, 5H), 4.47 (m, 2H), 3.97 (m, 4H), 1.43 and 1.34 (two s, 9H); IR (film) vmax 3292, 2974, 2933, 1708, 1636, 1569, 1456, 1395, 1369, 1251, 1164, 1031, 964, 908, 856, 780, 739, 697 cm−1; FABHRMS (NBA-CsI) m/z 455.0599 (M+Cs+, C16H22N2O5 requires 455.0583).

Data for N-((tert-Butyloxy)carbonyl)-N'-(2-(2,5-dimethoxyphenyl)ethyl)iminodiacetic Acid Monoamide (D4): Synthesized exactly as described in the general procedure using the appropriate amines shown in FIG. 5. 1H NMR (CDCl3, 500 MHz) d 7.54 and 6.90 (two s, 1H, NH), 6.72 (m, 3H), 3.94 (m, 4H), 3.77 (two s, 3H), 3.74 (two s, 3H), 3.52 (m, 2H), 2.81 (m, 2H), 1.43 and 1.38 (two s, 9H); IR (film) vmax 3307, 2974, 2933, 2831, 1708, 1631, 1503, 1451, 1390, 1364, 1226, 1164, 1041, 979, 928, 908, 877, 856, 805, 780, 733, 708 cm−1; FABHRMS (NBA-CsI) m/z 529.0938 (M+Cs+, C19H28N2O7 requires 545.0951).

Data for N-((tert-Butyloxy)carbonyl)-N'-(3,4,5-trimethoxybenzyl)iminodiacetic Acid Monoamide (D5): Synthesized exactly as described in the general procedure using the appropriate amines shown in FIG. 5. 1H NMR (CDCl3, 500 MHz) d 8.30 and 7.62 (two s, 1H, NH), 6.55 and 6.48 (two s, 2H), 4.37 (m, 2H), 3.96 (m, 4H), 3.82, 3.81, 3.79, and 3.78 (four s, 9H), 1.42, 1.40, and 1.30 (three s, 9H); IR (film) vmax 3293, 2974, 2933, 1702, 1636, 1590, 1508, 1456, 1421, 1390, 1364, 1328, 1236, 1164, 1123, 1005 cm−1; FABHRMS (NBA-CsI) m/z 545.0873 (M+Cs+, C19H28N2O8 requires 545.0900).

General Procedure for the Second Diversification For Library 1 and 2 (B1–B10 and E1–E6): N-((tert-Butyloxy)carbonyl)-N'-(4-methoxybenzyl)-N"-(3-fluoro-(trifluoromethyl)benzyl)iminodiacetic Acid Diamide (A5B5) as shown in FIG. 2. The acid A5 (0.616 g, 1.75 mmol) was dissolved in DMF (18 mL) and added to a flask containing i-Pr2NEt (0.45 g, 3.5 mmol) and 3-fluoro-5-(trifluoromethyl)benzyl amine (B5, 0.37 g, 1.9 mmol; any other primary or secondary amine can be substituted as long as reactive side groups are protected, eg. alcohols protected as TBS, alkyl, benzyl; acids protected as esters/amides; etc). PyBOP (1.00 g, 1.9 mmol) was added in portions and the resulting mixture was stirred overnight (16 h). The reaction mixture was poured into a separatory funnel containing 100 mL of 10% aqueous HCl. Extraction into EtOAc (2 to 40 mL) followed by washing of the combined organic phases with 10% aqueous HCl (2 to 40 mL)to saturated aqueous NaCl (1 to 40 mL), saturated aqueous NaHCO3, (2 ¥ 40 mL) and saturated aqueous NaCl (1 to 40 mL), drying (Na2SO4) and evaporation provided 0.79 g (90%) of A5B5 as an oil: 1H NMR (DMSO-d6, 400 MHz) d 9.50 (m, 0.5H), 9.30 (m, 0.5H), 8.96 (m, 1H), 7.49 (m, 3H), 7.18 (d, 2H, J=6.4 Hz), 6.84 (d, 2H, J=8.8 Hz), 4.40 (m, 2H), 4.24 (m, 2H), 4.04 (s, 4H), 3.71 (s, 3H), 1.28 and 1.27 (two s, 9H); IR (film) vmax 3246, 3071, 2978, 2935, 2839, 1656, 1610, 1563, 1514, 1456, 1394, 1366, 1343, 1302, 1251, 1230, 1170, 1131, 1030, 976, 959, 874, 847, 759, 718, 699 cm−1; FABHRMS (NBA-NaI) m/z 550.1291 (M+Na+, C25H29F4N3O5 requires 550.1941).

The remaining AXBX were characterized in a matrix format, which allowed for an assessment of the integrity of each of the coupling reactions:

Data for N-((tert-Butyloxy)carbonyl)-N'-(2-(phenyl)ethyl)-N"-(2-(2,5-dimethoxyphenyl)ethyl)iminodiacetic Acid Diamide (A1B1): Synthesized exactly as described in the general procedure using the appropriate amines shown in FIG. 5. 1H NMR (DMSO-d6, 400 MHz) d 8.68 (m, 2H), 7.25 (m, 5H), 6.87 (d, 1H, J=8.5 Hz), 6.73 (s, 2H), 3.79 and 3.75 (two s, 2H), 3.72 (s, 3H), 3.72 and 3.68 (two s, 2H), 3.67 (s, 3H), 3.33 (m, 4H), 2.70 (m, 4H), 1.33 and 1.31 (two s, 9H); IR (film) vmax 3423, 3074, 2975, 2934, 2833, 1970, 1651, 1567, 1500, 1454, 1393, 1367, 1337, 1305, 1250, 1225, 1165, 1141, 1043, 960, 895, 850, 802, 752, 701, 666 cm−1; FABHRMS (NBA-CsI) m/z 632.1745 (M+Cs+, C27H37N3O6 requires 632.1737).

Data for N-((tert-Butyloxy)carbonyl)-N'-(2-(4-fluorophenyl)ethyl)-N"-(3-(N-pyrrolidin-2-onyl)propyl)

iminodiacetic Acid Diamide (A6B2): Synthesized exactly as described in the general procedure using the appropriate amines shown in FIG. 5. 1H NMR (DMSO-d6, 500 MHz) d 8.65 (m, 2H), 7.25 (m, 2H), 7.09 (m, 2H), 3.79 (d, 2H, J=6 Hz), 3.77 and 3.75 (two s, 2H), 3.30 (m, 4H), 3.17 (m, 2H), 3.08 (m, 2H), 2.77 (m, 2H), 2.19 (m, 2H), 1.96 (m, 2H), 1.58 (m, 2H), 1.33 and 1.31 (two s, 9H); IR (film) vmax 3415, 3082, 2977, 2936, 1654, 1560, 1510, 1458, 1395, 1369, 1253, 1221, 1163, 1144, 1100, 1016, 961, 847, 761 cm−1; FABHRMS (NBA-CsI) m/z 611.1659 (M+Cs+, C24H35FN4O5 requires 611.1646).

Data for N-((tert-Butyloxy)carbonyl)-N'-(2-(4-methoxyphenyl)ethyl)-N"-(2-(3,4 dimethoxyphenyl)ethyl) iminodiacetic Acid Diamide (A2B3 and D3E3): Synthesized exactly as described in the general procedure using the appropriate amines shown in FIG. 5. 1H NMR (DMSO-d6, 400 MHz) d 8.67 (m, 2H), 7.13 (m, 2H), 6.84 (m, 4H), 6.72 (d, 1H, J=8.0 Hz), 3.79 and 3.76 (two s, 2H), 3.73 (s, 3H), 3.72 and 3.70 (two s, 2H), 3.70 (s, 6H), 3.33 (m, 4H), 2.65 (m, 4H), 1.31 (two s, 9H); IR (film) vmax 3250, 3074, 2935, 2835, 2056, 1650, 1212, 1571, 1514, 1454, 1417, 1393, 1367, 1301, 1247, 1159, 1141, 1029, 960, 895, 848, 809, 762, 665 cm−1; FABHRMS (NBA-CsI) m/z 662.1850 (M+Cs+, C28H39N3O7 requires 662.1842).

Data for N-((tert-Butyloxy)carbonyl)-N'-(2-(4-fluorophenyl)ethyl)-N"-((3,4,5-trimethoxy)benzyl) iminodiacetic Acid Diamide (A6B4): Synthesized exactly as described in the general procedure using the appropriate amines shown in FIG. 5. 1H NMR (DMSO-d6, 400 MHz) d 9.15 (m, 0.5H), 9.01 (m, 0.5H), 8.72 (m, 1H), 7.24 (m, 2H), 7.07 (m, 2H), 6.61 (d, 2H, J=11.4 Hz), 4.25 (m, 2H), 3.88 (s, 2H), 3.83 (m, 2H), 3.76 (s, 3H), 3.74 (s, 3H), 3.61 (s, 3H), 3.30 (m, 2H), 2.71 (m, 2H), 1.30 and 1.25 (two s, 9H); IR (film) vmax 3348, 3073, 2997, 2839, 1700, 1653, 1593, 1559, 1509, 1457, 1424, 1394, 1367, 1329, 1237, 1162, 1128, 1005, 959, 898, 826, 755, 667 cm−1; FABHRMS (NBA-CsI) m/z 666.1574 (M+Cs+, C27H36FN3O7 requires 666.1592).

Data for N-((tert-Butyloxy)carbonyl)-N'-(2-(4-hydroxyphenyl)ethyl)-N"-di(2-methoxyethyl)iminoacetic Acid Diamide (A3B6): Synthesized exactly as described in the general procedure using the appropriate amines shown in FIG. 5. 1H NMR (DMSO-d6, 400 MHz) d 9.11 (br s, 1H), 8.67 (m, 1H), 6.98 (m, 2H), 6.67 (m, 2H), 4.15 and 4.10 (two s, 2H), 3.74 and 3.68 (two s, 2H), 3.44 (m, 8H), 3.26 (s, 3H), 2.24 (s, 3H), 3.22 (m, 2H), 2.57 (m, 2H), 1.34 and 1.33 (two s, 9H; IR (film) vmax 3234, 3078, 2978, 2931, 1698, 1643, 1515, 1453, 1393, 1367, 1252, 1169, 1118, 1015, 962, 893, 832, 754, 665 cm−1; FABHRMS (NBA) m/z 468.4724 (M+H+, C23H37N3O7 requires 468.2710).

Data for N-((tert-Butyloxy)carbonyl)-N'-(2-(4-fluorophenyl)ethyl)-N"-(2-(hydroxy-2-ethoxy)ethyl) iminodiacetic Acid Diamide (A6B7): Synthesized exactly as described in the general procedure using the appropriate amines shown in FIG. 5. 1H NMR (DMSO-d6, 400 MHz) d 8.64 (m, 2H), 7.26 (m, 2H), 7.08 (m, 2H), 3.79 (m, 4H), 3.37 (m, 10H), 2.71 (m, 2H), 1.33 and 1.30 (two s, 9H); IR (film) vmax 3450, 2977, 2937, 2118, 1650, 1459, 1609, 1456, 1392, 1368, 1340, 1253, 1220, 1161, 1140, 1065, 960, 823 cm−1; FABHRMS (NBA-CsI) m/z 574.1317 (M+Cs+, C21H32FN3O6 requires 574.1329).

Data for N-((tert-Butyloxy)carbonyl)-N'-(2-(4-methoxyphenyl)ethyl)-N"-(3-(2,6-dimethoxybenzoyl) aminopropyl)iminodiacetic Acid Diamide (A2B8): Synthesized exactly as described in the general procedure using the appropriate amines shown in FIG. 5. 1H NMR (DMSO-d6, 500 MHz) d 8.66 (m, 2H), 8.00 (m, 1H), 7.27 (m, 1H), 7.12 (m, 2H), 6.83 (m, 2H), 6.64 (d, 2H, J=10 Hz), 3.80 (m, 4H), 3.71 (s, 9H), 3.22 (m, 6H), 2.64 (m, 2H), 1.60 (m, 2H), 1.34 and 1.31 (two s, 9H); IR (film) vmax 3260, 2936, 2838, 1651, 1598, 1514, 1474, 1393, 1388, 1302, 1252, 1158, 1141, 1113, 1034, 959, 897, 847, 757, 666 cm−1; FAB-HRMS (NBA-CsI) m/z 719.2079 (M+Cs+, C30H42N4O8 requires 719.2057).

Data for N-((tert-Butyloxy)carbonyl)-N'-(2-(phenyl) ethyl)-N"-(5-acetamido-5-methoxycarbonyl)pentyl) iminodiacetic Acid Diamide (A1B9): Synthesized exactly as described in the general procedure using the appropriate amines shown in FIG. 5. 1H NMR (DMSO-d6, 500 MHz) d 8.73 (m, 2H), 8.57 (m, 1H), 7.27 (m, 5H), 4.17 (m, 1H), 3.78 (m, 4H), 3.60 (s, 3H), 3.32 (m, 2H), 3.12 (m, 2H), 2.71 (m, 2H), 1.43 (m, 4H), 1.39 (m, 2H), 1.32 and 1.30 (s, 9H); IR (film) vmax 3751, 3277, 3079, 2937, 1738, 1652, 1557, 1514, 1456, 1394, 1369, 1301, 1248, 1177, 1143, 1033, 961, 894, 847, 767, 665 cm−1; FABHRMS (NBA-CsI) m/z 653.1983 (M+Cs+, C26H40N4O7 requires 653.1951).

Data for N-((tert-Butyloxy)carbonyl)-N'-((4-methoxy) benzyl)-N"-(5-(benzyloxycarbonylamido)-5-(methoxycarbonyl)pentyl)iminodiacetic Acid Diamide (A4B10): Synthesized exactly as described in the general procedure using the appropriate amines shown in FIG. 5. 1H NMR (DMSO-d6, 500 MHz) d 8.68 (m, 3H), 7.73 (m, 1H), 7.34 (m, 5H), 7.17 (m, 1H), 7.76 (m, 2H), 5.03 (s, 2H), 3.99 (m, 2H), 3.76 (m, 7H), 3.61 (s, 3H), 3.30 (m, 2H), 3.05 (m, 2H), 2.68 (m, 2H), 1.36 (m, 14H); IR (film) vmax 3384, 3268, 3074, 2936, 1707, 1656, 1583, 1562, 1546, 1492, 1454, 1393, 1367, 1266, 121, 1166, 1039, 848, 780, 752, 697 cm−1; FABHRMS (NBA-CsI) m/z 775.2328 (M+Cs+, C33H46N4O9 requires 775.2319).

Data for N-((tert-Butyloxy)carbonyl)-N'-benzyl-N"-(4-methoxybenzyl)iminodiacetic Acid Diamide (D1E1): Synthesized exactly as described in the general procedure of FIG. 10 using the appropriate amines shown in FIG. 11. 1H NMR (CDCl3, 500 MHz) d 8.60 (m, 1H, NH), 8.20 (m, 1H, NH), 7.26 (m, 7H), 6.75 (m, 2H), 4.39 and 4.32 (two s, 4H), 3.75 (m, 7H), 1.32 (s, 9H); IR (film) vmax 3241, 3067, 2974, 2833, 1703, 1656, 1559, 1513, 1452, 1390, 1369, 1246, 1174, 1139, 1031, 959, 897, 846, 744, 697 cm−1; FABHRMS (NBA-CsI) m/z 574.1296 (M+Cs+, C24H31N3O5 requires 574.1318).

Data for N-((tert-Butyloxy)carbonyl)-N'-(2-(3-methoxyphenyl)ethyl)-N"-(2-phenylethyl)iminodiacetic Acid Diamide (D2E2): Synthesized exactly as described in the general procedure of FIG. 10 using the appropriate amines shown in FIG. 11. 1H NMR (CDCl3, 500 MHz) d 8.40 (m, 1H, NH), 7.80 (m, 1H, NH), 7.21 (m, 6H), 6.78 (m, 3H), 3.76 (apparent two s, 7H), 3.50 (m, 4H), 2.82 (m, 4H), 1.38 (s, 9H); IR (film) vmax 3245, 3070, 2974, 2933, 1704, 1654, 1654, 1585, 1564, 1487, 1452, 1395, 1369, 1256, 1164, 1036, 903, 780, 749, 697 cm−1; FABHRMS (NBA-CsI) m/z 601.1611 (M+Cs+, C26H35N3O5 requires 602.1631).

Data for N-((tert-Butyloxy)carbonyl)-N'-(2-(2, 5dimethoxyphenyl)ethyl)-N"-(3-fluoro-5-(trifluoromethyl) benzyl)iminodiacetic Acid Diamide (D4E4): Synthesized exactly as described in the general procedure of FIG. 10 using the appropriate amines shown in FIG. 11. 1H NMR (CDCl3, 500 MHz) d 9.84 and 9.18 (two t, 1H, NH), 7.25 (m, 3H), 7.09 and 6.59 (two t, 1H, NH), 6.73 (m, 3H), 4.49 (d, 2H, J=6 Hz) 3.77 (m, 1 OH), 3.48 (apparent dd, 2H), 2.80 (apparent dd, 2H), 1.35 (s, 9H); IR (film) vmax 3231, 3067, 2974, 2933, 2831, 1703, 1656, 1564, 1503, 1456, 1390, 1364, 1339, 1246, 1221, 1169, 1128, 1092, 1044, 977, 960, 874, 801, 700 cm−1; FABHRMS (NBA-CsI) m/z 704.1379 (M+Cs+, C27H33N3O6F4 requires 704.1360).

Data for N-((tert-Butyloxy)carbonyl)-N"-(3,4,5-trimethoxybenzyl)-N"'-(N-a-CBZ-L-lysine methyl ester) iminodiacetic Acid Diamide (D5E5): Synthesized exactly as described in the general procedure of FIG. 10 using the appropriate amines shown in FIG. 11. 1H NMR (CDCl3, 500 MHz) d 8.59 and 8.20 (two s, 1H, NH), 7.25 (m, 5H), 6.60 and 6.52 (two s, 2H), 5.54 (apparent d, 1H), 5.08 (apparent d, 2H), 4.38 (m, 3H), 3.88 (m, 13H), 3.32 (s, 3H), 3.25 (m, 2H), 1.80 (m, 2H), 1.74 (m, 2H), 1.68 (m, 2H), 1.38 and 1.29 (two s, 9H); IR (film) vmax 3426, 2995, 1641, 1508 cm−1; FABHRMS (NBA-CsI) m/z 821.2398 (M+Cs+, C34H48N4O11 requires 821.2374).

Data for N-((tert-Butyloxy)carbonyl)-N'-(2-(4-fluorophenyl)ethyl)-N"-di(2-methoxyethyl)iminodiacetic Acid Diamide (D6E6): Synthesized exactly as described in the general procedure of FIG. 10 using the appropriate amines shown in FIG. 11. 1H NMR (CDCl3, 500 MHz) d 9.20 and 9.96 (two t, 1H, NH), 7.05 (m, 2H), 6.80 (m, 2H), 4.05, 3.92, 3.76, and 3.66 (four s, 4H), 3.38 (m, 8H), 3.17 (m, 6H), 2.68 (m, 2H), 1.27 (s, 9H); IR (film) vmax 3508, 3241, 3077, 2974, 2923, 1702, 1641, 1564, 1508, 1441, 1390, 1364 1251, 1221, 1164, 111, 1010, 964, 928, 892, 826 cm−1; FABHRMS (NBA-CsI) m/z 602.1634 (M+Cs+, C23H36N3O6 requires 602.1642).

Synthesis of N-((tert-Butyloxy)carbonyl)-N'-(2-(4-methoxyphenyl)ethyl)-N"-di(2-methoxyethyl)iminodiacetic Acid Diamide (A2B6) as shown in FIG. 2. The acid A2 (6 g, 16.4 mmol) was dissolved in DMF (100 mL) and added to a flask containing i-Pr2NEt (4.7 g, 36 mmol) and di-(2-methoxyethyl)amine (B6, 2.4 g, 18 mmol). PyBOP (9.4 g, 18 mmol) was added in portions and the resulting mixture was stirred overnight (16 h). The reaction mixture was poured into a separatory funnel containing 400 mL of 10% aqueous HCl. Extraction into EtOAc (200+100 mL) followed by washing of the combined organic phases with 10% aqueous HCl (2 to 200 mL), saturated aqueous NaCl (200 mL), 5% aqueous NaHCO3 (2 to 100 mL) and saturated aqueous NaCl (2 to 100 mL), drying (Na2 SO4) and evaporation returned 6.69 g (85%) of A2B6 as an oil: Rf=0.5 (10% CH3OH-CHCl3); 1H NMR (DMSO-d6, 500 MHz) d 8.70 (m, 1H), 7.12 (m, 2H), 6.82 (m, 2H), 4.15 (s, 1H), 4.10 (s, 1H), 3.74 (s, 1H), 3.71 (s, 3H), 3.68 (s, 1H), 3.43 (m, 10H), 3.26 (s, 3H), 3.23 (s, 3H), 2.64 (m, 2H), 1.34 and 1.32 (two s, 9H); IR (film) vmax 3852, 3749, 3674, 3647, 3446, 2932, 1700, 1684, 1653, 1635, 1559, 1540, 1513, 1457, 1394, 1367, 1247, 1176, 1116, 1033, 844 cm−1; FABHRMS (NBA-CsI) m/z 614.1820 (M+Cs+, C24H39N3O7 requires 614.1842).

General Procedure for the Third Diversification For Library 1 (C1–C10): using the example for Sub-Library A1B3C1–C10 as illustrated in FIG. 2. CHCl3 (1 mL) and 4 M HCl-dioxane (1 mL) were added to A1B3 (0.075 g, 0.15 mmol) in a 4 mL vial and this mixture was allowed to stand for 2 h. TLC (10% CH3OH-CHCl3 eluent) then indicated that conversion to the amine was complete. The solvent and excess acid were removed by evaporation. A stock solution was prepared by diluting a mixture of 0.5 mmol of each diacid (C1–C10, 1 mmol of each of the two cis/trans-mixtures C7,8 and C9,10 was employed) and 45 mmol of i-Pr2NEt to 100 mL in anhydrous DMF. This stock solution (1 mL, 0.005 mmol of each diacid, 0.45 mmol of i-Pr2NEt) was added to the diamide and the mixture was shaken to effect dissolution. PyBrOP (0.070 g, 0.15 mmol) was added and mixture was capped, shaken, and allowed to stand for 8 h. The reaction mixture was diluted with EtOAc (25 mL) and washed with 20% aqueous HCl saturated with NaCl (3 to 25 mL), saturated aqueous NaHCO3 (1 to 25 mL) and saturated aqueous NaCl (1 to 25 mL), dried (Na2 SO4) and concentrated to afford 0.036 g (79%) of the sub-library.

MS data confirming the integrity of the mixtures with the inclusion of each expected member were collected for the following mixtures: A1B1Cn, A2B1Cn, A3B1Cn, A2B2Cn, A3B3Cn, A4B4Cn, A5B5Cn, A6B6Cn, A5B7Cn, A4B8Cn, A3B9Cn and A2B10Cn.

General Procedure for the Synthesis of Individual Sub-Library Entries For Library 1 (as illustrated in FIG. 9): Preparation of (E)-(N,N'-Bis(N-(2-(4-methoxyphenyl)ethyl) carboxamidomethyl)-N,N'-bis(N,N-di(2-methoxyethyl) carboxamidomethyl)ethene-1,2-dicarboxamide, A2B6C2. The BOC-derivative A2B6 (0.84 g) was stirred in 4 M HCl-dioxane (8.5 mL) for 2 h. Removal of the solvent under a stream of N2 and in vacuo gave the deprotected material as a slightly greenish oil (0.78 g), which was dissolved in anhydrous DMF to provide a 0.15 M solution (12.5 mL). An aliquot of this solution (2 mL, 0.3 mmol) was syringed into a two dram vial equipped with a stirring bar containing 11.6 mg (0.1 mmol) of fumaric acid. i-Pr2NEt (150 μL, 0.9 mmol) and PyBrOP (140 mg, 0.3 mmol) were added and the reaction mixture was stirred for 16 h at 25° C. The reaction mixture was diluted with EtAOc (50 mL) and washed (3 to 50 mL) with acidic saturated aqueous NaCl (10% aqueous HCl/saturated aqueous NaCl 1/1), 5% aqueous NaHCO3 (50 mL) and saturated aqueous NaCl (50 mL), dried (Na2SO4) and the solvent was removed under reduced pressure to provide 73 mg (89%) of the title substance as an oil, which crystallized from slowly evaporating ethyl acetate: 1H NMR (DMSO-d6, 250 MHz) d 8.62 and 8.23 (two t, total 2H, NH), 7.11–7.06 (m, 5H), 7.00 (s, 2H, vinyl), 6.84–6.81 (m, 4H), 4.55, 4.27, 4.04 and 3.86 (br s or pairs of s, total 8H, NCH2CO), 3.70 (two s, 6H, OCH3), 2.61 (m, 4H, ArCH2); IR (film) vmax 3467, 3262, 1644, 1246, 1115 cm−1; FABHRMS (NBA-CsI) m/z 843.4542 (M+H+, C42H62N6O12 requires 843.4504).

Data for 8 synthesis of N,N'-Bis(N-(2-(4-methoxyphenyl) ethyl)carboxamidomethyl)-N,N'-bis(N,N-di(2-methoxyethyl)carboxamidomethyl)ethyne-1,2-dicarboxamide, A2B6C1: 1H NMR (DMSO-d6, 250 MHz) Synthesized exactly as described in the general procedure of FIG. 10 using the appropriate diacid shown in FIG. 11. d 8.43 and 8.23 (br t, total 2H), 7.13–7.08 (m, 4H), 6.85–6.81 (m, 4H), 4.54, 4.26, 4.08 and 3.86 (br s or pairs of s, total 8H), 3.70 (two s, 6H), 2.62 (m, 4H); IR (film) vmax 3487, 3272, 1651, 1246, 1115 cm−1; FABHRMS (NBA-CsI) m/z 973.3369 (M+Cs+, C42H60N6O12 requires 973.3324).

Data for (E)-N,N'-Bis(N-(2-(4-methoxyphenyl)ethyl) carboxamidomethyl)-N,N'-bis(N,N-di(2-methoxyethyl) carboxamidomethyl)-2-butene-1,4-dicarboxamide, A2B6C3: Synthesized exactly as described in the general procedure of FIG. 10 using the appropriate diacid shown in FIG. 11. 1H NMR (DMSO-d6, 250 MHz) d 8.69 and 8.25 (two t, total 2H), 7.12–7.08 (m, 4H), 6.84–6.80 (m, 4H), 5.50 (m, 2H), 4.40, 4.16, 3.93 and 3.78 (br s, total 8H), 3.69 (two s, 6H), 2.63 (m, 4H); IR (film) vmax 3446, 3261, 1650, 1245, 1115 cm−1; FABHRMS (NBA-CsI) m/z 1003.3841 (M+Cs+, C44H66N6O12 requires 1003.3793).

Data for N,N'-Bis(N-(2-(4-methoxyphenyl)ethyl) carboxamidomethyl)-N,N'-bis(N,N-di(2-methoxyethyl) carboxamidomethyl)benzene-1,3-dicarboxamide, A2B6C4: Synthesized exactly as described in the general procedure of FIG. 10 using the appropriate diacid shown in FIG. 11. 1H NMR (DMSO-d6, 250 MHz) d 8.45, 8.41 and 8.29 (t, t and m, total 2H), 7.45–7.33 (m, 4H), 7.15–7.09 (m, 4H), 6.84–6.81 (m, 4H), 4.31, 4.22, 3.94 and 3.77 (br s, total 8H), 3.70 (s, 6H), 2.65 (m, 4H); IR (film) vmax 3487, 3262, 1651, 1246, 1113 cm-1; FABHRMS (NBA-CsI) m/z 1025.3678 (M+Cs+, C46H64N6O12 requires 1025.3637).

Data for N,N'-Bis(N-(2-(4-methoxyphenyl)ethyl) carboxamidomethyl)-N,N'-bis(N,N-di(2-methoxyethyl) carboxamidomethyl)benzene-1,4-dicarboxamide, A2B6C5: Synthesized exactly as described in the general procedure of FIG. 10 using the appropriate diacid shown in FIG. 11. 1H NMR (DMSO-d6, 250 MHz) d 8.40 and 8.28 (two m, total 2H), 7.38–7.34 (m, 4H), 7.14–7.08 (m, 4H), 6.85–6.81 (m, 4H), 4.31, 4.23, 3.93 and 3.77 (br s or d, total 8H), 3.70 (br s, 6H), 2.65 (m, 4H); IR (film) vmax 3497, 3272, 1644, 1244, 1115 cm-1; FABHRMS (NBA-CsI) m/z 1025.3677 (M+Cs+, C46H64N6O12 requires 1025.3637).

Data for N,N'-Bis(N-(2-(4-methoxyphenyl)ethyl) carboxamidomethyl)-N,N'-bis(N,N-di(2 methoxyethyl) carboxamidomethyl)napthalene-1,4-dicarboxamide, A2B6C6: Synthesized exactly as described in the general procedure of FIG. 10 using the appropriate diacid shown in FIG. 11. 1H NMR (DMSO-d6, 250 MHz) d 8.31, 8.20 and 8.09 (m, total 4H), 7.70–7.59 (m, 2H), 7.38–7.28 (m, 2H), 7.18–7.16 (m, 2H), 7.02–6.95 (m, 2H), 6.87–6.78 (m, 4H), 4.85, 4.40, 4.15, and 4.02 (br s, total 4H), 3.70 (m, 6H), 2.69 (m, 4H); IR (film) vmax 3282, 1650, 1241, 1113 cm-1; FABHRMS (NBA-CsI) m/z 1075.3835 (M+Cs+, C50H66N6O12 requires 1075.3793).

Data for cis- and trans-N,N'-Bis(N-(2-(4-methoxyphenyl) ethyl)carboxamidomethyl)-N,N'-bis(N,N-di(2-methoxyethyl)carboxamidomethyl)cyclohexane-1,3-dicarboxamide, A2B6C7,8: (mixture of cis- and trans-isomers): Synthesized exactly as described in the general procedure of FIG. 10 using the appropriate diacid shown in FIG. 11. 1H NMR (DMSO-d6, 250 MHz) d 8.78, 8.67, 8.51 and 8.19 (m, total 2H), 7.17–7.10 (m, 4H), 6.86–6.83 (m, 4H), 4.50–3.75 (several m, total 8H), 3.72 (br s, 6H), 2.64 (m, 4H); IR (film) vmax 3487, 3262, 1642, 1246, 1113 cm-1; FABHRMS (NBA-CsI) m/z 1031.4147 (M+Cs+, C46H70N6O12 requires 1031.4106).

Data for cis- and trans-N,N'-Bis(N-(2-(4-methoxyphenyl) ethyl)carboxamidomethyl)-N,N'bis(N,N-di(2-methoxyethyl)carboxamidomethyl)cyclohexane-1,4-dicarboxamide, A2B6C9,10: (mixture of cis- and trans-isomers): Synthesized exactly as described in the general procedure of FIG. 10 using the appropriate diacid shown in FIG. 11. 1H NMR (DMSO-d6, 250 MHz) d 8.67, 8.23 and 8.17 (m, total 2H), 7.13–7.08 (m, 4H), 6.85–6.80 (m, 4H), 4.50–3.75 (several m, total 8H), 3.70 (br s, 6H), 2.62 (m, 4H); IR (film) vmax 3477, 3262, 1644, 1246, 1115 cm-1; FABHRMS (NBA-CsI) m/z 1031.4148 (M+Cs+, C46H70N6O12 requires 1031.4106).

Preparation of the Sub-Library A2B6C1-10. A stock solution was prepared through diluting a mixture of 0.5 mmol of each diacid (C1–10, 1 mmol of each of the two cis/trans-mixtures C7,8 and C9,10 was employed) and 45 mmol of DIEA to 100 mL in anhydrous DMF. 2 mL of this stock solution (0.1 mmol of diacid) was added to 2 mL of the solution containing A2B6·HCl (0.3 mmol, see above). After the addition of PyBrOP (140 mg, 0.3 mmol), the mixture was stirred for 16 h. Work-up as described above provided 84.5 mg (95%) of the library as an off-white solid. TLC (10% CH3OH—CHCl3) Rf=0.47–0.62. The results from HPLC-MS analysis of this mixture (including selective ion monitoring) were in good agreement with those obtained using a mixture produced by pooling the individual compounds (see FIG. 5). The remaining, similarly prepared mixtures were characterized in a matrix format, which allowed for qualitative assessment of the integrity of the sublibraries.

General Procedure for the Third Diversification For Library 2, using examples for the preparation of the Individual Components (D1E1F1, D1E1F2, D1E1F3, D1E1F4)—FIGS. 10 and 11: Preparation of N-(4-Pentenylcarbonyl)-N'-benzyl-N"-(4-methoxybenzyl) iminodiacetic Acid Diamide (D1E1F1). The BOC-derivative D1E1 (146 mg, 0.33 mmol) was stirred in 4 M HCl-dioxane (2.5 mL) for 4 h. Removal of the solvent under a stream of N2 and in vacuo gave the deproteced material as a pale yellow solid. The crude amine hydrochloride was dissolved in anhydrous DMF (4.5 mL) and F1 (25 mg, 0.22 mmol) was added. i-Pr2NEt (173 µL, 0.99 mmol) and PyBOP (154 mg, 0.33 mmol) were added and the reaction mixture was stirred for 16 h at 25° C. The reaction mixture was diluted with EtOAc (100 mL) and washed (3 t 100 mL) with acidic saturated aqueous NaCl (20% aqueous HCl/saturated aqueous NaCl: 1/1), saturated aqueous NaHCO3 (2 to 100 mL), saturated aqueous NaCl (100 mL), dried (Na2SO4) and the solvent was removed under reduced presure to provide 80 mg (83%) of the D1E1F1 as an oil: 1H NMR (CDCl3, 500 MHz) d 9.60 (m, 1H, NH), 7.25 (m, 7H), 7.15 (m, 1H, NH), 6.82 (m, 2H), 5.69 (m, 1H), 4.95 (m, 2H), 4.39 (m, 4H), 3.85 (m, 4H), 3.76 (s, 3H), 2.15 (m, 2H), 1.97 (m, 2H), 1.60 (m, 2H); IR (film) vmax 3272, 3067, 2933, 1646, 1554, 1508, 1456, 1246,1174, 1026, 917, 815, 744, 697 cm–1; FABHRMS (NBA-CsI) m/z 570.1375 (M+Cs+, C25H31N3O4 requires 570.1369).

Data for N-(5-Hexenylcarbonyl)-N'-benzyl-N"-(4-methoxybenzyl)iminodiacetic Acid Diamide (D1E1F2): Synthesized exactly as described in the general procedure of FIG. 10 using the appropriate diacid shown in FIG. 11. 1H NMR (CDCl3, 500 MHz) d 9.55 (m, 1H, NH), 7.26 (m, 7H), 6.83 (m, 2H), 6.27 (two s, 1H, NH), 5.75 (m, 1H), 4.95 (m, 2H), 4.44 (m, 4H), 4.03 and 4.01 (two s, 2H), 3.89 and 3.88 (two s, 2H), 3.79 (m, 3H), 2.20 (m, 2H), 1.56 (m, 2H), 1.32 (m, 2H); IR (film) vmax 3272, 3067, 2933, 1646, 1554, 1513, 1456, 1246, 1174, 1031, 641, 821 cm–1; FABHRMS (NBA-CsI) m/z 584.1535 (M+Cs+, C26H33N3O4 requires 584.1535).

Data for N-(8-Nonenylcarbonyl)-N'-benzyl-N"-(4-methoxybenzyl)iminodiacetic Acid Diamide (D1E1F3): Synthesized exactly as described in the general procedure of FIG. 10 using the appropriate diacid shown in FIG. 11. 1H NMR (CDCl3, 500 MHz) d 9.65 (m, 1H, NH), 7.25 (m, 7H), 6.84 (m, 2H), 6.32 (two s, 1H, NH), 5.80 (m, 1H), 4.94 (m, 2H), 4.43 (m, 4H), 4.03 (m, 2H), 3.89 (m, 2H), 3.79 (m, 3H), 2.21 (m, 2H), 2.04 (m, 2H), 1.55 (m, 2H), 1.36 (m, 2H), 1.21 (m, 6H); IR (film) vmax 3272, 3067, 2923, 2851, 1656, 1636, 1564, 1549, 1513, 1462, 1246, 1174, 1031 cm–1; FABHRMS (NBA-CsI) m/z 626.2006 (M+Cs+, C29H39N3O4 requires 626.1995).

Data for N-(4-Decenylcarbonyl)-N'-benzyl-N"-(4-methoxybenzyl)iminodiacetic Acid Diamide (D1E1F4): Synthesized exactly as described in the general procedure of FIG. 10 using the appropriate diacid shown in FIG. 11. 1H NMR (CDCl3, 500 MHz) d 9.50 (m, 1H), 7.27 (m, 7H), 6.83 (m, 2H), 6.50 (two s, 1H, NH), 5.81 (m, 1H), 4.96 (m, 2H), 4.43 (m, 4H), 4.01 (apparent d, 2H), 3.88 (broad s, 2H), 3.77 (m, 3H), 2.18 (m, 2H), 2.03 (m, 2H), 1.52 (m, 2H), 1.25 (m, 2H), 1.25 and 1.22 (two s, 8H); IR (film) vmax 3262, 3077, 2923, 2851, 1656, 1641, 1564, 1549, 1513, 1462, 1246, 1174, 1031 cm–1; FABHRMS (NBA-CsI) m/z 640.2165 (M+Cs+, C30H41N3O4 requires 640.2151).

Procedure for the Third Diversification of Library 2 using examples for D1E1F1–4, D2E2F1–4, D3E3F1–4, D4E4F1–4, D5E5F1–4, D6E6F1–4 as illustrated in FIG. 10: Preparation of D2E2F1–4. A stock solution was prepared by diluting a mixture of 2.5 mmol of each ω-alkene carboxylic acid (F1–F4) and 45 mmol of i-Pr2NEt to 100 mL in anhydrous DMF. A 4.97 mL sample of this stock solution (0.497 mmol of w-alkene carboxylic acid) was added to D2E2.HCl (0.746 mmol, see above). After the addition of PyBrOP (348 mg, 0.746 mmol), the mixture was stirred for 16 h at 25° C. Work-up as described above provided 102 mg (41%) of the title mixture as a light yellow oil. The 1H NMR spectrum showed the vinyl protons (CH=CH2) as two multiplets at d 5.70 and 4.96, respectively. The MS spectrum (ESMS) exhibited all the expected molecular ion peaks: (M+H+) 536, 522, 480, 466.

General Procedure for the Synthesis of Individual Homodimer (Olefin Metathesis) Sub-Library Entries in Library 2 (D1E1F1-D1E1F1, D1E1F2-D1E1F2, D1E1F3-D1E1F3, D1E1F4-D1E1F4) as illustrated in FIG. 10: Preparation of D1E1F1-D1E1F1. A solution of D1E1F1 (22 mg, 0.050 mmol) and RuCl2(PCy3) 2=CHPh (10 mg, 0.12 mmol) in CHCl3 (2 mL) was warmed at reflux for 16 h. The solvent was removed in vacuo and chromatography (SiO2, 1.5×20 cm, 50–100% EtOAc-hexane, and 5% CH3OH-EtOAc) afforded 14 mg (66%) of D1E1F1-D1E1F1 as a yellow oil: 1H NMR (CDCl3, 500 MHz) d 9.47 (broad s, 2H, NH), 7.23 (m, 16H, fourteen aromatic and two NH), 6.81 (m, 4H), 5.20 (apparent br two s, 2H), 4.40 (m, 8H), 3.77 (m, 14H), 2.18 (m, 4H), 1.90 (m, 4H), 1.52 (m, 4H); IR (film) vmax 3272, 3067, 2933, 2851, 1651, 1559, 1513, 1456, 1400, 1400, 1303, 1246, 1174, 1026, 1026, 959, 821, 739, 697 cm−1; FABHRMS (NBA-CsI) m/z 979.3337 (M+Cs+, C48H58N6O8 requires 979.3370). D1E1F2-D1E1F2: 1H NMR (CDCl3, 500 MHz) d 9.60 (m, 2H), 7.26 (m, 16H, fourteen aromatic and two NH), 6.81 (m, 4H), 5.28 (br s, 2H), 4.40 (m, 8H), 3.77 (m, 14H), 2.17 (br s, 4H), 1.94 (br s, 4H), 1.50 (br s, 4H), 1.27 (m, 4H); IR (film) vmax 3272, 3067, 2933, 2851, 1652, 1558, 1514, 1456, 1431, 1303, 1249, 1203, 1180, 1133, 1026, 964, 805, 697 cm−1; FABHRMS (NBA-CsI) m/z 1007.3638 (M+Cs+, C50H62N6O8Cs requires 1007.3683).

D1E1F3-D1E1F3: 1H NMR (CDCl3, 500 MHz) d 9.65 (m, 2H, NH), 7.27 (m, 14H), 6.82 (m, 4H), 6.60 (m, 2H, NH), 5.37 (m, 2H), 4.40 (m, 8H), 4.00 (m, 4H) 3.86 (br s, 4H), 3.78 and 3.77 (two s, 6H), 2.19 (m, 4H), 1.60 (m, 4H), 1.53 (m, 4H), 1.32 (m, 4H), 1.22 (m, 12H); IR (film) vmax 3262, 3056, 2923, 2851, 1662, 1651, 1564, 1513, 1451, 1246, 1174, 1144, 1113, 1026, 959, 892, 856, 821 cm−1; FABHRMS (NBA-CsI) m/z 1091.4671 (M+Cs+, C56H74N6O8 requires 1091.4622).

D1E1F4-D1E1F4: 1H NMR (CDCl3, 500 MHz) d 9.60 (m, 2H, NH), 7.26 (m, 14H), 6.82 (m, 4H), 6.60 (m, 2H, NH), 5.38 (m, 2H), 4.40 (m, 8H), 4.00 (m, 4H), 3.86 (br s, 4H), 3.78 and 3.77 (two s, 6H), 2.19 (m, 4H), 1.97 (m, 4H), 1.52 (m, 4H), 1.32 (m, 4H), 1.22 (m, 16H); IR (film) vmax 3272, 3067, 2923, 1646, 1559, 1513, 1451, 1246, 1174, 1031 cm−1; FABHRMS (NBA-CsI) m/z 1119.4985 (M+Cs+, C58H78N6O8 requires 1119.4985).

General Procedure for the Synthesis of a Homodimer Sub-Library (15) For Library 2 as illustrated in FIG. 10. A solution of D1E1F1–4 (39 mg, 0.082 mmol) and RuCl2 (PCy3) 2=CHPh (17 mg, 0.021 mmol) in CHCl3 (2 mL) was warmed at reflux for 16 h. The solvent was removed in vacuo and chromatography (SiO2, 1.5 ¥ 20 cm, 50–100% EtOAc-hexane, and 5% CH3OH-EtOAc) afforded 26 mg (67%) of the homodimer sub-library as a yellow oil. The 1H NMR spectrum exhibited the olefinic protons (CH=CH) as a multiplet at d 5.35. The MS spectrum (ESMS) exhibited all the molecular ion peaks (10 different components which have 9 different molecular weights): (M+H+) 987, 973, 959, 931, 917, 903, 875, 861, 847.

General Procedure for the Synthesis of a Homodimer/Heterodimer Sub-Library (15 and 16) For Library 2 as illustrated in FIG. 10. A solution of D3E3F1–4 (11 mg, 0.020 mmol), D6E6F1–4 (12 mg, 0.020 mmol; used only as a representative example—the other DEF substrates are equally accessable), and RuCl2(PCy3) 2=CHPh (8.2 mg, 0.01 mmol) in CHCl3 (2 mL) was warmed at reflux for 16 h. The solvent was evaporated and chromatography (SiO2, 1.5×20 cm, 50–100% EtOAc-hexane, 5–15% CH3OH-EtOAc) afforded 14 mg (62%) of the sub-library as a yellow oil. The 1H NMR spectrum showed the olefinic protons (CH=CH) as a multiplet at d 5.35. The MS spectrum (ESMS) exhibited all the molecular ion peaks (36 different components which have 18 different molecular weights): (M+H+) 1128, 1234, 1220, 1206, 1192, 1136, 1178, 1164, 1122, 1108, 1164, 1150, 1052, 1094, 1080, 1066, 1038, 1024.

SYNTHETIC PROTOCALS FOR EXAMPLE 2 AS ILLUSTRATED IN FIGS. 16–19

General Procedure for the First Diversification (A): N-((tert-Butyloxy)carbonyl)-N'-(2-(3-methoxyphenyl)ethyl)iminodiacetic Acid Monoamide (A1) as illustrated in FIG. 17. A mixture of N-((tert-butyloxy)carbonyl) iminodiacetic acid (1.00 g, 4.29 mmol) and EDCI (0.826 g, 4.29 mmol) in 10 mL of anhydrous DMF was stirred for 1 h at 25° C. 3-Methoxyphenylethyl amine (0.648 g, 4.29 mmol) was added to the resulting solution. The reaction mixture was stirred for 20 h at 25° C. before it was poured into 75 mL of 10% aqueous HCl. The mixture was extracted with EtOAc (3×50 mL) and the combined organic phases were washed with 10% aqueous HCl (2×50 mL), saturated aqueous NaCl (50 mL), dried (Na2SO4) and the solvent removed in vacuo to afford 1.45 g (92%) of A1 as an oil: identical in all respects with authentic material.

General Procedure for the Second Diversification (AB): N-((tert-butyloxy)carbonyl)-N'-(2-(3-methoxyphenyl)ethyl)-N"-(2-phenylethyl)iminodiacetic Acid Diamide (A1B1) as illustrated in FIG. 17. The monoamide A1 (0.945 g, 2.58 mmol) was dissolved in DMF (10 mL) and added to a flask containing i-Pr2NEt (0.668 g, 5.16 mmol) and phenylethyl amine (B1, 0.344 g, 2.84 mmol). PyBOP (1.48 g, 2.84 mmol) was added and the resulting mixture was stirred overnight at 25° C. (16 h). The reaction mixture was poured into 75 mL of 10% aqueous HCl and extracted into EtOAc (3 ¥ 50 mL). The combined organic phases were washed with 10% aqueous HCl (2 ¥ 50 mL), saturated aqueous NaCl (50 mL), saturated aqueous NaHCO3 (2 ¥ 50 mL), and saturated aqueous NaCl (50 mL), dried (Na2SO4) and concentrated to provide 1.14 g (94%) of A1B114 as an oil: 1H NMR (CDCl3, 500 MHz) d 8.40 (m, 1H, NH), 7.80 (m, 1H, NH), 7.21 (m, 6H), 6.78 (m, 3H), 3.76 (apparent two s, 7H), 3.50 (m, 4H), 2.82 (m, 4H), 1.38 (s, 9H); IR (film) vmax 3245, 3070, 2974, 2933, 1704, 1654, 1654, 1585, 1564, 1487, 1452, 1395, 1369, 1256, 1164, 1036, 903, 780, 749, 697 cm−1; FABHRMS (NBA-CsI) m/z 602.1611 (M+Cs+, C26H35N3O5Cs requires 602.1631).

General Procedure for the ω-Alkene Carboxamide Derivatives of N-Boc-Iminodiacetic Acid (C1–C4): N-(9-Decenylcarbonyl)iminodiacetic Acid (C4) as illustraed in FIG. 17. A mixture of 9-decenylcarboxylic acid (0.368 g, 2.0 mmol) and EDCI (0.384 g, 2.0 mmol) in 4 mL of dioxane/H2O (1/1) was stirred for 4 h at 25° C. A homogeneous solution of iminodiacetic acid (0.266 g, 2.0 mmol), dioxane (2 mL), NaOH (0.160 g, 4.0 mmol) and H2O (2 mL) was added. After stirring at 25 ° C. for 16 h, the reaction mixture was washed with Et2O (8 mL) and the aqueous layer was then acidified with the addition of 10% aqueous HCl (8 mL). The mixture was extracted with EtOAc (3×8 mL) and the combined organic layers were washed with saturated aqueous NaCl (2 ¥ 10 mL), dried (Na2SO4) and concentrated. PTLC afforded 272 mg (45%) of C4 as a colorless oil: 1H NMR (CDCl3, 400 MHz) d 5.77 (m, 1H), 4.92 (m, 2H), 4.19 (broad s, 4H), 2.31 (m, 2H), 2.02 (m, 2H), 1.59 (broad s, 2H), 1.26 (m, 10H); IR (film) vmax 3467, 2923, 2851, 1723, 1610, 1477, 1410, 1200, 964, 908 cm−1; FABHRMS (NBA-NaI) m/z 300.1821 (M+H+, C15H25NO5 requires 300.1811).

N-(4-Pentenylcarbonyl)iminodiacetic Acid (C1): 1H NMR (CD3OD, 500 MHz) d 5.77 (m, 1H), 4.95 (m, 2H), 4.09 (two s, 4H), 2.33 (m, 2H), 2.07 (m, 2H), 1.68 (m, 2H); IR (film) vmax 3500, 2980, 2940, 1718, 1641, 1467, 1400, 1328, 1226, 1190, 9780, 918 cm−1; FABHRMS (NBA-NaI) m/z 252.0840 (M+Na+, C10H15NO5 requires 252.0848).

N-(5-Hexenylcarbonyl)iminodiacetic Acid (C2): 1H NMR (CD3OD, 500 MHz) d 5.70 (m, 1H), 4.92 (m, 2H), 4.09 (two s, 4H), 2.23 (m, 2H), 1.99 (m, 2H), 1.52 (m, 2H), 1.35 (m, 2H); IR (film) vmax 3477, 2933, 1723, 1641, 1462, 1405, 1328, 1226, 1195, 995, 974, 913 cm−1; FABHRMS (NBA-NaI) m/z 266.1012 (M+Na+, C11H17NO5 requires 266.1004).

N-(8-Nonenylcarbonyl)iminodiacetic Acid (C3): 1H NMR (CDCl3, 500 MHz) d 5.78 (m, 1H), 4.96 (m, 2H), 4.20 (broad s, 4H), 2.33 (m, 2H), 2.02 (m, 2H), 1.59 (m, 2H), 1.32 (m, 8H); IR (film) vmax 3428, 2920, 1723, 1633, 1614, 1464, 1340, 1330, 1216, 912 cm−1; FABHRMS (NBA-NaI) m/z 286.1562 (M+H+, C14H23NO5 requires 286.1654).

Figure 18:
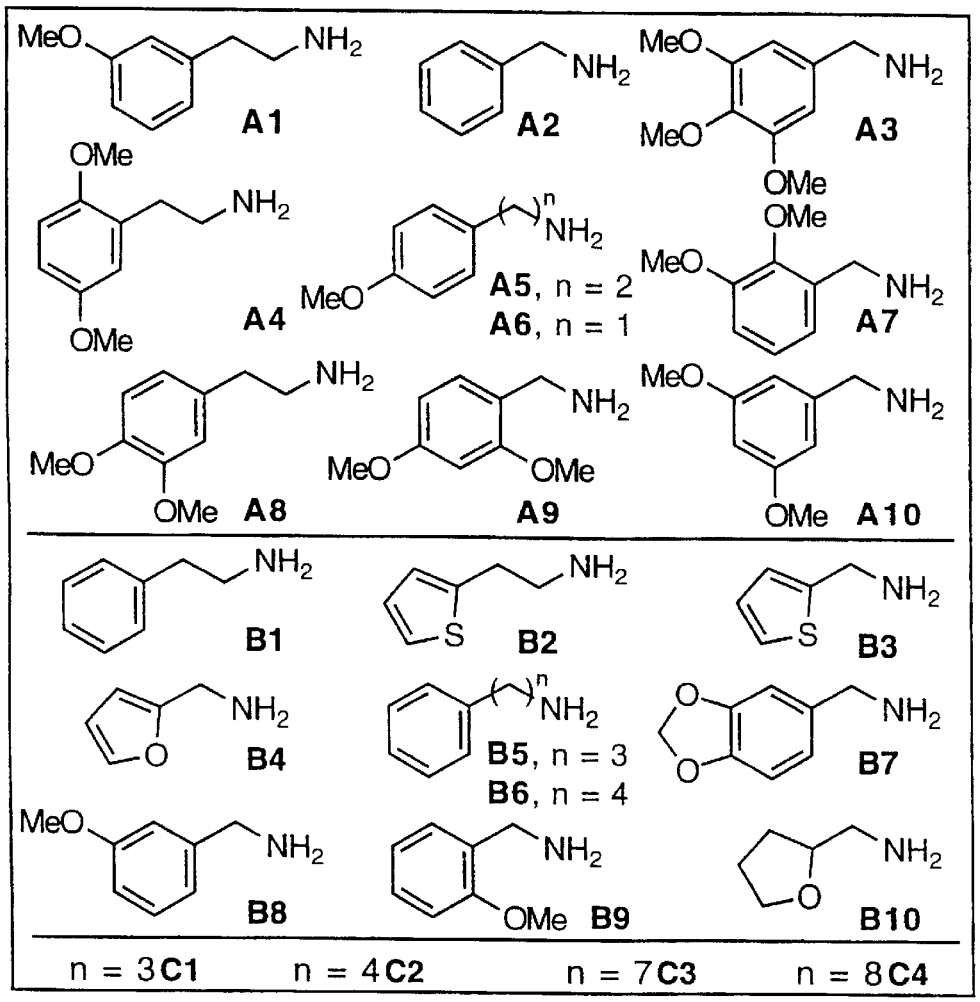
FIG. 18 illustrates the synthesis of libraries (example 2) enlisting 10 or 20 amines (A1–A5/A1–A10 and B1–B5/B1–B10) and 4 ω-alkene carboxamide derivatives of N-BOC-iminodiacetic acid (C1–C4).
Figure 19:
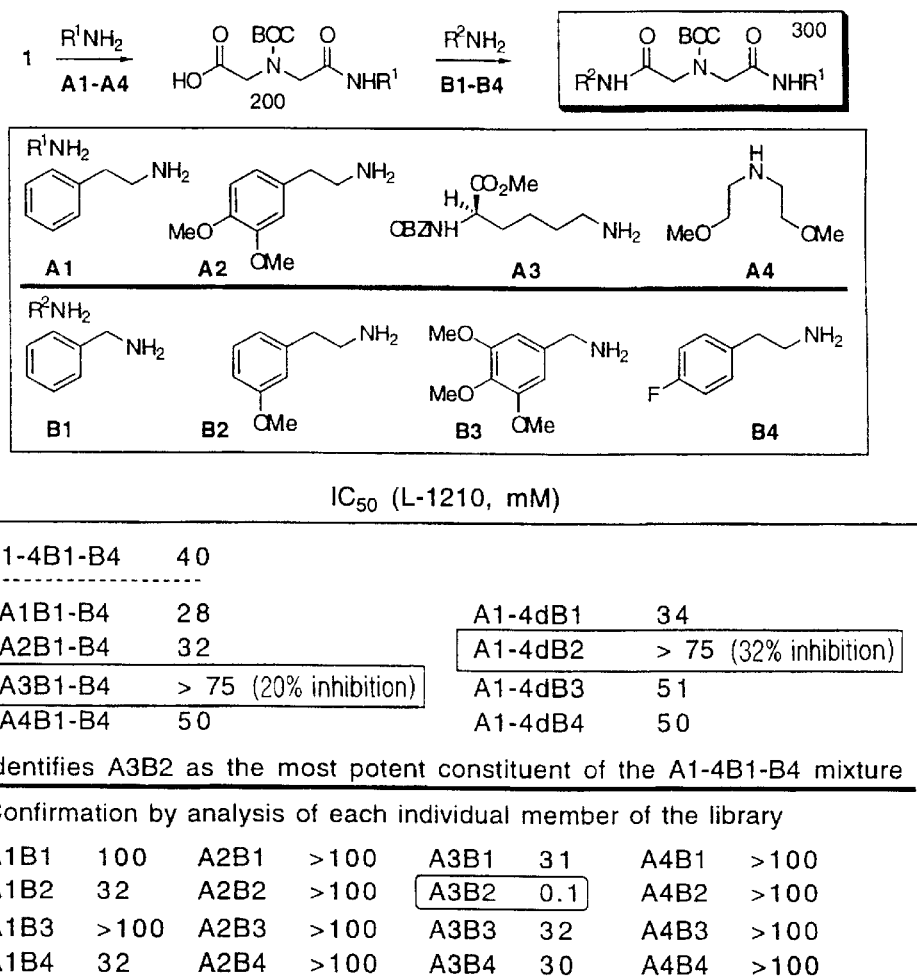
FIG. 19 illustrates the synthesis of iminodiacetic acid diamide libraries with cytoxicities of some of the active compounds shown—activities represented as $IC_{50}$ values from L-1210 $\mu$M cell lines.

General Procedure for the Individual Tetra-amides using the example of N,N'-Bis(N-(2-(3-methoxyphenyl)ethyl)carboxamidomethyl)-N,N'-bis(N-(2-phenyl)ethyl)carboxamidomethyl)-N"-(8-nonenylcarbonyl)iminodiacetic Acid Diamide (A1B1C3) as illustrated in FIG. 17 (functional amines and acids are shown in FIG. 18). The Boc-derivative A1B1 (174 mg, 0.371 mmol) was stirred in a solution of 4 M HCl-dioxane (2 mL) at 25° C. for 4 h. Removal of the solvent under N2 and in vacuo gave the deprotected material as a pale yellow solid. The crude amine hydrochoride was dissolved in anhydrous DMF (2 mL) and C3 (35 mg, 0.124 mmol), i-Pr2NEt (0.194 mL, 1.11 mmol) and PyBrOP (173 mg, 0.371 mmol) were added sequentially. The reaction mixture was stirred for 16 h at 25° C. before being diluted with EtOAc (20 mL) and washed with 10% aqueous HCl (2×20 mL), saturated aqueous NaHCO3 (2 ¥ 20 mL), saturated aqueous NaCl (20 mL), and dried (Na2SO4). The solvent was removed under reduced pressure to provide 73 mg (60%) of the title substance as an oil: 1H NMR (CDCl3, 400 MHz) d 7.24–7.14 (m, 12H), 6.73 (m, 6H), 6.80 (m, 1H), 4.89 (m, 2H), 4.15–3.72 (m, 18 H), 3.48 (m, 8H), 2.80 (m, 8H), 2.12 (m, 2H), 1.94 (m, 2H), 1.52 (m, 2H), 1.24 (m, 8H); IR (film) vmax 3273, 3077, 2931, 2859, 1647, 1554, 1451, 1259, 1202, 1150, 1041, 964, 912, 839, 782, 746, 700 cm−1; FABHRMS (NBA-CsI) m/z 1120.4578 (M+Cs+, C56H73N7O9 requires 1120.4524).

Data for N,N'-Bis(N-(2-(3-methoxyphenyl)ethyl)carboxamidomethyl)-N,N'-bis-(N-(2-phenyl)ethyl)carboxamidomethyl)-N"-(4-pentenylcarbonyl)iminodiacetic Acid Diamide (A1B1C1): Synthesized according to the general procedure above using the respective amines and acid shown in FIG. 18. 1H NMR (CDCl3, 500 MHz) d 7.28–7.14 (m, 12H), 6.73 (m, 6H), 6.80 (m, 1H), 4.92 (m, 2H), 4.15–3.73 (m, 18 H), 3.51 (m, 8H), 2.82 (m, 8H), 2.16 (m, 2H), 2.03 (m, 2H), 1.65 (m, 2H); IR (film) vmax 3272, 3067, 2933, 1666, 1585, 1564, 1467, 1440, 1256, 1195, 1154, 1036, 964, 918, 785, 749, 692 cm−1; FABHRMS (NBA-CsI) m/z 1064.3940 (M+Cs+, C52H65N7O9 requires 1064.3898).

Data for N,N'-Bis(N-(2-(3-methoxyphenyl)ethyl)carboxamidomethyl)-N,N'-bis(N-(2-phenyl)ethyl)carboxamidomethyl)-N"-(5-hexenylcarbonyl)iminodiacetic Acid Diamide (A1B1C2): Synthesized according to the general procedure above using the respective amines and acid shown in FIG. 18. 1H NMR (CDCl3, 400 MHz) d 7.24–7.14 (m, 12H), 6.73 (m, 6H), 6.80 (m, 1H), 4.92 (m, 2H), 4.14–3.72 (m, 18 H), 3.47 (m, 8H), 2.80 (m, 8H), 2.14 (m, 2H), 2.00 (m, 2H), 1.56 (m, 2H), 1.37 (m, 2H); IR (film) vmax 3280, 3060, 2935, 2861, 1651, 1547, 1489, 1447, 1431, 1259, 1196, 1154, 1092, 1039, 961, 914, 846, 783, 746, 699 cm−1; FABHRMS (NBA-CsI) m/z 1078.4096 (M+Cs+, C53H67N7O9 requires 1078.4055).

Data for N,N'-Bis(N-(2-(3-methoxyphenyl)ethyl)carboxamidomethyl)-N,N'-bis(N-(2-phenyl)ethyl)carboxamidometyl)-N"-(8-decenylcarbonyl)iminodiacetic Acid Diamide (A1B1C4): Synthesized according to the general procedure above using the respective amines and acid shown in FIG. 18. 1H NMR (CDCl3, 400 MHz) d 7.24–7.14 (m, 12H), 6.73 (m, 6H), 6.80 (m, 1H), 4.92 (m, 2H), 4.15–3.72 (m, 18 H), 3.46 (m, 8H), 2.82 (m, 8H), 2.12 (m, 2H), 1.96 (m, 2H), 1.53 (m, 2H), 1.23 (m, 10H); IR (film) vmax 3273, 3066, 2921, 2849, 1657, 1557, 1458, 1259, 1201, 1154, 1039, 966, 914, 846, 783, 746, 699 cm−1; FABHRMS (NBA-CsI) m/z 1134.4747 (M+Cs+, C57H75N7O9 requires 1134.4681).

General Procedure for the Third Diversification: Preparation of A1B1C1–4 as shown in FIG. 17. A stock solution was prepared by dissolving a mixture of 0.2 mmol of each w-alkene iminodiacetic acid (C1–C4) and 7.2 mmol of i-Pr2NEt in 8 mL of anhydrous DMF. A 1.90 mL of this stock solution (0.19 mmol of CX) was added to A1B1.HCl (0.57 mmol). After the addition of PyBrOP (266 mg, 0.57 mmol), the mixture was stirred for 16 h at 25° C. Work-up as described provided 184 mg (66%) of the title substance as a light yellow oil. The 1H NMR spectrum shows the vinyl protons (CH=CH2) as two multiplets at 5.80 and 4.92 ppm, respectively. The MS exhibited all the expected molecular ions: (M+H+) 932, 947, 989, 1003.

General Procedure for the Synthesis of Individual Homodimer Sub-Library Entries: Preparation of A1B1C3-A1B1C3 as shown in FIG. 17. A solution of A1B1C3 (25 mg, 0.025 mmol) and RuCl2(PCy3) 2=CHPh (3.3 mg, 0.0040 mmol) in CHCl3 (2 mL) was warmed at reflux for 16 h. The solvent was removed in vacuo and chromatography (SiO2, 1.5 to 20 cm, 50–100% EtOAc-hexane and 5% CH3OH-EtOAc) afforded 15 mg (60%) of A1B1C3-A1B1C3 as a yellow oil: 1H NMR (CDCl3, 400 MHz) d 7.25–7.14 (m, 24H), 6.99–6.71 (m, 12H), 5.24 (apparent br s, 2H), 4.15–3.72 (m, 36H), 3.49 (m, 16H), 2.82 (m, 16H), 2.13 (m, 4H), 1.87 (m, 4H), 1.40 (m, 4H), 1.23 (m, 16H); IR (film) vmax 3280, 3071, 2924, 2851, 1651, 1573, 1458, 1405, 1259, 1201, 1154, 1086, 1039, 966, 919, 846, 778, 736, 699 cm−1; FABHRMS (NBA-CsI) m/z 2079.9866 (M+Cs+, C110H142N14O18 requires 2079.9681).

A1B1C1–A1B1C1: 1H NMR (CDCl3, 500 MHz) d 7.25–7.17 (m, 24H), 6.71 (m, 12H), 5.24 (apparent broad s, 2H), 4.18–3.72 (m, 36H), 3.45 (m, 16H), 2.87 (m, 16H), 2.16 (m, 4H), 1.90 (m, 4H), 1.50 (m, 4H); IR (film) vmax 3276, 3073, 2930, 1658, 1579, 1460, 1257, 1150, 1038, 967, 906, 779, 739, 698 cm−1; FABHRMS (NBA-CsI) m/z 1967.8584 (M+Cs+, C102H126N14O18 requires 1967.8429).

A1B1C2-A1B1C2: 1H NMR (CDCl3, 400 MHz) d 7.25–7.14 (m, 24H), 6.71 (m, 12H), 5.24 (apparent br s, 2H), 4.15–3.72 (m, 36H), 3.46 (m, 16H), 2.78 (m, 16H), 2.12 (m, 4H), 1.90 (m, 4H), 1.40 (m, 4H), 1.29 (m, 4H); IR (film) vmax 3282, 3067, 2923, 1656, 1560, 1462, 1446, 1410, 1262, 1200, 1149, 1036, 964, 841, 785, 749, 697 cm−1; FABHRMS (NBA-CsI) m/z 1995.8910 (M+Cs+, C104H130N14O18 requires 1995.8742).

A1B1C4-A1B1C4: 1H NMR (CDCl3, 400 MHz) d 7.26–7.16 (m, 24H), 6.71 (m, 12H), 5.24 (apparent br s, 2H), 4.15–3.73 (m, 36H), 3.46 (m, 16H), 2.80 (m, 16H), 2.15 (m, 4H), 1.97 (m, 4H), 1.51 (m, 4H), 1.20 (m, 20 H); IR (film) vmax 3271, 3067, 2923, 2851, 1662, 1456, 1251, 1195, 1149, 1036, 961, 841, 774, 739, 697 cm−1; FABHRMS (NBA-CsI) m/z 2108.0195 (M+Cs+, C112H146N14O18 requires 2107.9994).

General Procedure for the Synthesis of a Homodimer Sub-Library as illustrated in FIG. 17: A solution of A1B1Cl-4 (50 mg, 0.052 mmol) and RuCl2(PCy3) 2=CHPh (6.8 mg, 0.0082 mmol) in CHCl3 (2 mL) was warmed at reflux for 16 h. Then the solvent was removed in vacuo and chromatography (SiO2, 1.5 ¥ 20 cm, 50–100% EtOAc-hexane and 5% CH3OH-EtOAc) afforded 32 mg (64%) of the homodimer sub-library as a yellow oil. The 1H NMR spectrum exhibited the olefinic protons (CH═CH) as a multiplet at d 5.24. The MS exhibited all the expected molecular ions (10 different components with 9 different molecular weights): ESMS (M+Na+) m/z 1858, 1873, 1887, 1914, 1929, 1943, 1971, 1984, 1999.

General Procedure for the Hydrogenation of Individual Homodimer Sub-Library Entries as illustrated in FIG. 17: Using the example for preparation of A1B1C4-A1B1C4. A solution of A1B1C4-A1B1C4 (11 mg, 0.0056 mmol) and 10% Pd-C (0.1 wt equiv) in CH3OH (2 mL) was stirred under H2 at 25° C. for 40 h. After filtration, the solvent was removed in vacuo to afford 10 mg (91%) of the title compound as a yellow oil: 1H NMR (CDCl3, 400 MHz) d 7.26–7.16 (m, 24H), 6.71 (m, 12H), 4.15–3.73 (m, 36H), 3.46 (m, 16H), 2.80 (m, 16H), 2.15 (m, 4H), 1.51 (m, 4H), 1.20 (m, 28H); IR (film) vmax 3276, 3062, 2920, 2839, 1668, 1582, 1460, 1262, 1262, 1196, 1155, 1033, 962, 693 cm−1; FABHRMS (NBA-CsI) m/z 2110.0292 (M+Cs+, C112H148N14O18 requires 2110.0150).

A1B1C1–A1B1C1: 1H NMR (CDCl3, 500 MHz) d 7.25–7.17 (m, 24H), 6.71 (m, 12H), 4.18–3.72 (m, 36H), 3.45 (m, 16H), 2.87 (m, 16H), 2.16 (m, 4H), 1.50 (m, 4H), 1.20 (m, 8H); IR (film) vmax 3275, 3076, 2932, 1649, 1554, 1455, 1432, 1261, 1193, 1153, 1035, 963, 855 cm−1; FABHRMS (NBA-CsI) m/z (M+Cs+, C102H128N14O18 requires).

A1B1C2–A1B1C2: 1H NMR (CDCl3, 400 MHz) d 7.25–7.14 (m, 24H), 6.71 (m, 12H), 4.15–3.72 (m, 36H), 3.46 (m, 16H), 2.78 (m, 16H), 2.12 (m, 4H), 1.40 (m, 4H), 1.24 (m, 12H); IR (film) vmax 3280, 3071, 2924, 2851, 1657, 1557, 1453, 1411, 1259, 1196, 1149, 1039, 961, 919, 840, 783, 736, 694 cm−1; FABHRMS (NBA-CsI) m/z 1997.9079 (M+Cs+, C104H132N14O18 requires 1997.8898).

A1B1C3–A1B1C3: 1H NMR (CDCl3, 400 MHz) d 7.25–7.14 (m, 24H), 6.99–6.71 (m, 12H), 4.15–3.72 (m, 36H), 3.49 (m, 16H), 2.82 (m, 16H), 2.13 (m, 4H), 1.40 (m, 4H), 1.23 (m, 24H); IR (film) vmax 3280, 3071, 2924, 2851, 1651, 1562, 1458, 1254, 1196, 1154, 1034, 961, 914, 788, 741, 694 cm−1; FABHRMS (NBA-CsI) m/z 2081.9968 (M+Cs+, C110H144N14O18 requires 2081.9837).

General Procedure for the Hydrogenation of a Homodimer Sub-Library as illustrated in FIG. 17: A solution of A1B1Cl-4-A1B1C1-4 (11 mg, 0.00577 mmol) and 10% Pd-C (0.1 wt. equiv) in CH3OH (2 mL) was stirred under H2 at 25° C. for 40 h. After filtration, the solvent was removed in vacuo afforded 9 mg (82%) of the title sub-library as a yellow oil. The 1H NMR spectrum exhibited no olefinic protons (CH═CH). The MS exhibited all the expected molecular ions (9 different components with 9 different molecular weights): ESMS (M+H+) m/z 1859, 1874, 1888, 1916, 1931, 1945, 1972, 1987, 2001.

SYNTHETIC PROTOCALS FOR EXAMPLE 3

General Procedure for the First Diversification: N-((tert-Butyloxy)carbonyl)-N'-(2-(4-mothoxyphenyl)ethyl) iminodiacetic Acid Monoamide (Library 1, A3) as illustrated in FIGS. 24/26. A mixture of N-((tert-butyloxy)carbonyl) iminodiacetic acid (4.66 g, 20 mmol) and EDCI (3.8 g, 20 mmol) in 60 mL of anhydrous DMF was stirred for 1 h at 25° C. 4-Methoxyphenethyl amine (A3, 3.0 g, 20 mmol) was added to the resulting solution in four portions (slightly exothermic). The reaction mixture was stirred for 20 h at 25° C. before it was poured into 250 mL of 10% aqueous HCl. The product was extracted into EtAOc (3 to 200 mL) and the combined organic phases were washed with 10% aqueous HCl (2×200 mL), saturated aqueous NaCl (2×200 mL), dried (Na2SO4) and the solvent removed in vacuo to afford 7.3 g (99%) of the title compound as a white solid: Rf=0.6 (10% HOAc-EtOAc); 1H NMR (DMSO-d6, 500 MHz) d 8.27 (m, 1H), 7.12 (m, 2H), 6.84 (m, 2H), 3.91, 3.87, 3.83 and 3.80 (four s, 4H), 3.70 (s, 3H), 3.25 (m, 2H), 2.64 (m, 2H), 1.35 and 1.32 (two s, 9H); IR (film) vmax 2976, 2931, 1705, 1635, 1513, 1456, 1393, 1368, 1248, 1164, 1032, 824, 600 cm−1; FABHRMS (NBA-NaI) m/z 367.1862 (M+H+, C18H26N2O6 requires 367.1869).

N-((tert-Butyloxy)carbonyl)-N'-(benzyl)iminodiacetic Acid Monoamide (A1): 1H NMR (CDCl3, 500 MHz) d 8.03 and 7.13 (two s, 1H, NH), 7.27 (m, 5H), 4.47 (m, 2H), 3.97 (m, 4H), 1.43 and 1.34 (two s, 9H); IR (film) vmax 3292, 2974, 2933, 1708, 1636, 1569, 1456, 1395, 1369, 1251, 1164, 1031, 964, 908, 856, 780, 739, 697 cm−1; FABHRMS (NBA-CsI) m/z 455.0599 (M+Cs+, C16H22N2O5 requires 455.0583).

N-((tert-Butyloxy)carbonyl)-N'-(2-(3-methoxyphenyl) ethyl)iminodiacetic Acid Monoamide (A2): 1H NMR (DMSO-d6, 500 MHz) d 8.26 (m, 1H), 7.19 (m, 1H), 6.76 (m, 3H), 3.90, 3.87, 3.84 and 3.81 (four s, 4H), 3.73 (s, 3H), 3.32 (m, 2H), 2.69 (q, 2H, J=10 Hz), 1.35 and 1.32 (two s, 9H); IR (film) vmax 3853, 3744, 3675, 3648, 3294, 2976, 1700, 1653, 1635, 1584, 1559, 1506, 1490, 1457, 1394, 1368, 1259, 1165, 1038, 963, 877, 781, 697 cm−1; FAB-HRMS (NBA-NaI) m/z 367.1860 (M+H+, C18H26N2O6 requires 367.1869).

N-((tert-Butyloxy)carbonyl)-N'-(2-(2,5-dimethoxyphenyl)ethyl)iminodiacetic Acid Monoamide (A4): 1H NMR (CDCl3, 500 MHz) d 7.54 and 6.90 (two s, 1H, NH), 6.72 (m, 3H), 3.94 (m, 4H), 3.77 (two s, 3H), 3.74 (two s, 3H), 3.52 (m, 2H), 2.81 (m, 2H), 1.43 and 1.38 (two s, 9H); IR (film) vmax 3307, 2974, 2933, 2831, 1708, 1631, 1503, 1451, 1390, 1364, 1226, 1164, 1041, 979, 928, 908, 877, 856, 805, 780, 733, 708 cm−1; FABHRMS (NBA-CsI) m/z 529.0938 (M+Cs+, C19H28N2O7 requires 545.0951).

N-((tert-Butyloxy)carbonyl)-N'-(3,4,5-trimethoxybenzyl) iminodiacetic Acid Monoamide (A5): 1H NMR (CDCl3, 500 MHz) d 8.30 and 7.62 (two s, 1H, NH), 6.55 and 6.48 (two s, 2H), 4.37 (m, 2H), 3.96 (m, 4H), 3.82, 3.81, 3.79, and 3.78 (four s, 9H), 1.42, 1.40, and 1.30 (three s, 9H); IR (film) vmax 3293, 2974, 2933, 1702, 1636, 1590, 1508, 1456, 1421, 1390, 1364, 1328;1236, 1164, 1123, 1005 cm−1; FABHRMS (NBA-CsI) m/z 545.0873 (M+Cs+, C19H28N2O8 requires 545.0900).

N-((tert-Butyloxy)carbonyl)-N'-(2-(4-fluorophenyl)ethyl) iminodiacetic Acid Monoamide (A6): 1H NMR (DMSO-d6, 500 MHz) d 8.23 (m, 1H), 7.24 (m, 2H), 7.09 (m, 2H), 3.89, 3.86, 3.82 and 3.80 (four s, 4H), 3.30 (m, 2H), 2.71 (m, 2H), 1.35 and 1.32 (two s, 9H); IR (film) vmax 3852, 3744, 3675, 3648, 3295, 2978, 1700, 1684, 1653, 1635, 1559, 1540, 1510, 1457, 1394, 1368, 1222, 1161, 896, 772 cm−1; FABHRMS (NBA-NaI) m/z 355.1661 (M+H+, C17H23N2O5 requires 355.1669).

General Procedure for the Second Diversification using the example of N-((tert-Butyloxy)carbonyl)-N'-(3,4,5-trimethoxybenzyl)-N"-(N-a-CBZ-L-lysine Methyl Ester) iminodiacetic Acid Diamide (Library 1, A5B5) as illustrated in FIG. 24. The monoamide A5 (0.237 g, 0.575 mmol) was dissolved in DMF (6 mL) and added to a flask containing i-Pr2NEt (0.223 g, 1.7 mmol) and CBZ-Lys-OCH3 (B5, 0.209 g, 0.632 mmol). PyBOP (0.33 g, 1.73 mmol) was added in portions and the resulting mixture was stirred overnight at 25° C. (16 h). The reaction mixture was poured into 60 mL of 10% aqueous HCl and extraction into EtOAc (3×40 mL) followed by washing of the combined organic phases with 10% aqueous HCl (2×60 mL), saturated aqueous NaCl (1×60 mL), saturated aqueous NaHCO3, (2×60 mL) and saturated aqueous NaCl (1×60 mL), drying (Na2SO4) and evaporation provided 0.355 g (93%) of A5B5 as an oil: 1H NMR (CDCl3, 500 MHz) d 8.59 and 8.20 (two s, 1H, NH), 7.25 (m, 5H), 6.60 and 6.52 (two s, 2H), 5.54 (apparent d, 1H), 5.08 (apparent d, 2H), 4.38 (m, 3H), 3.88 (m, 13H), 3.32 (s, 3H), 3.25 (m, 2H), 1.80 (m, 2H), 1.74 (m, 2H), 1.68 (m, 2H), 1.38 and 1.29 (two s, 9H); IR (film) vmax 3426, 2995, 1641, 1508 cm−1; FABHRMS (NBA-CsI) m/z 821.2398 (M+Cs+, C34H48N4O11 requires 821.2374).

All DXEX were similarly characterized providing an assessment of each of the coupling reactions.

N-((tert-Butyloxy)carbonyl)-N'-benzyl-N"-(4-methoxybenzyl)iminodiacetic Acid Diamide (A1B1): 1H NMR (CDCl3, 500 MHz) d 8.60 (m, 1H, NH), 8.20 (m, 1H, NH), 7.26 (m, 7H), 6.75 (m, 2H), 4.39 and 4.32 (two s, 4H), 3.75 (m, 7H), 1.32 (s, 9H); IR (film) vmax 3241, 3067, 2974, 2833, 1703, 1656, 1559, 1513, 1452, 1390, 1369, 1246, 1174, 1139, 1031, 959, 897, 846, 744, 697 cm−1; FABHRMS (NBA-CsI) m/z 574.1296 (M+Cs+, C24H31N3O5 requires 574.1318).

N-((tert-Butyloxy)carbonyl)-N'-(2-(3-methoxyphenyl) ethyl)-N"-(2-phenylethyl)iminodiacetic Acid Diamide (A2B2): 1H NMR (CDCl3, 500 MHz) d 8.40 (m, 1H, NH), 7.80 (m, 1H, NH), 7.21 (m, 6H), 6.78 (m, 3H), 3.76 (apparent two s, 7H), 3.50 (m, 4H), 2.82 (m, 4H), 1.38 (s, 9H); IR (film) vmax 3245, 3070, 2974, 2933, 1704, 1654, 1654, 1585, 1564, 1487, 1452, 1395, 1369, 1256, 1164, 1036, 903, 780, 749, 697 cm−1; FABHRMS (NBA-CsI) m/z 601.1611 (M+Cs+, C26H35N3O5 requires 602.1631).

N-((tert-Butyloxy)carbonyl)-N'-(2-(4-methoxyphenyl) ethyl)-N"-(2-(3,4-dimethoxyphenyl)ethyl)iminodiacetic Acid Diamide (A3 A3): 1H NMR (DMSO-d6, 400 MHz) d 8.67 (m, 2H), 7.13 (m, 2H), 6.84 (m, 4H), 6.72 (d, 1H, J=8.0 Hz), 3.79 and 3.76 (two s, 2H), 3.73 (s, 3H), 3.72 and 3.70 (two s, 2H), 3.70 (s, 6H), 3.33 (m, 4H), 2.65 (m, 4H), 1.31 (two s, 9H); IR (film) vmax 3250, 3074, 2935, 2835, 2056, 1650, 1212, 1571, 1514, 1454, 1417, 1393, 1367, 1301, 1247, 1159, 1141, 1029, 960, 895, 848, 809, 762, 665 cm−1; FABHRMS (NBA-CsI) m/z 662.1850 (M+Cs+, C28H39N3O7 requires 662.1842).

N-((tert-Butyloxy)carbonyl)-N'-(2-(2,5-dimethoxyphenyl)ethyl)-N"-(3-fluoro-5-(trifluoromethyl) benzyl)iminodiacetic Acid Diamide (A4B4): 1H NMR (CDCl3, 500 MHz) d 9.84 and 9.18 (two t, 1H, NH), 7.25 (m, 3H), 7.09 and 6.59 (two t, 1H, NH), 6.73 (m, 3H), 4.49 (d, 2H, J=6 Hz) 3.77 (m, 10H), 3.48 (apparent dd, 2H), 2.80 (apparent dd, 2H), 1.35 (s, 9H); IR (film) vmax 3231, 3067, 2974, 2933, 2831, 1703, 1656, 1564, 1503, 1456, 1390, 1364, 1339, 1246, 1221, 1169, 1128, 1092, 1044, 977, 960, 874, 801, 700 cm−1; FABHRMS (NBA-CsI) m/z 704.1379 (M+Cs+, C27H33N3O6F4 requires 704.1360).

N-((tert-Butyloxy)carbonyl)-N'-(2-(4-fluorophenyl) ethyl)-N"-di(2-methoxyethyl)iminodiacetic Acid Diamide (A6B6): 1H NMR (CDCl3, 500 MHz) d 9.20 and 9.96 (two t, 1H, NH), 7.05 (m, 2H), 6.80 (m, 2H), 4.05, 3.92, 3.76, and 3.66 (four s, 4H), 3.38 (m, 8H), 3.17 (m, 6H), 2.68 (m, 2H), 1.27 (s, 9H); IR (film) vmax 3508, 3241, 3077, 2974, 2923, 1702, 1641, 1564, 1508, 1441, 1390, 1364 1251, 1221, 1164, 111, 1010, 964, 928, 892, 826 cm−1; FABHRMS (NBA-CsI) m/z 602.1634 (M+Cs+, C23H36N3O6 requires 602.1642).

General Procedure for the Third Diversification for Library 1, Individual Components: Preparation of N-(4 Pentenylcarbonyl)-N'-benzyl-N"-(4-methoxybenzyl) iminodiacetic Acid Diamide (A1B1C1) as illustrated in FIG. 24. The BOC derivative A1B1 (146 mg, 0.33 mmol) was stirred in a solution of 4 M HCl-dioxane (2.5 mL) at 25° C. for 4 h. Removal of the solvent under N2 and in vacuo gave the deprotected material as a pale yellow solid. The crude amine hydrochloride was dissolved in anhydrous DMF (4.5 mL) and F1 (25 mg, 0.22 mmol—see chart on FIG. 24 for the other viable acids used), i-Pr2NEt (173 μL, 0.99 mmol) and PyBrOP (154 mg, 0.33 mmol) were added sequentially. The reaction mixture was stirred for 16 h at 25° C. before being diluted with EtOAc (100 mL) and washed (3×100 mL) with acidic saturated aqueous NaCl (20% aqueous HCl/saturated aqueous NaCl: 1/1), saturated aqueous NaHCO3 (2×100 mL), saturated aqueous NaCl (100 mL), and dried (Na2SO4). The solvent was removed under reduced pressure to provide 80 mg (83%) of the A1B1C1 as an oil: 1H NMR (CDCl3, 500 MHz) d 9.60 (m, 1H, NH), 7.25 (m, 7H), 7.15 (m, 1H, NH), 6.82 (m, 2H), 5.69 (m, 1H), 4.95 (m, 2H), 4.39 (m, 4H), 3.85 (m, 4H), 3.76 (s, 3H), 2.15 (m, 2H), 1.97 (m, 2H), 1.60 (m, 2H); IR (film) vmax 3272, 3067, 2933, 1646, 1554, 1508, 1456, 1246,1174, 1026, 917, 815, 744, 697 cm−1; FABHRMS (NBA-CsI) m/z 570.1375 (M+Cs+, C25H31N3O4 requires 570.1369).

N-(5-Hexenylcarbonyl)-N'-benzyl-N"-(4-methoxybenzyl)iminodiacetic Acid Diamide (A1B1C2): 1H NMR (CDCl3, 500 MHz) d 9.55 (m, 1H, NH), 7.26 (m, 7H), 6.83 (m, 2H), 6.27 (two s, 1H, NH), 5.75 (m, 1H), 4.95 (m, 2H), 4.44 (m, 4H), 4.03 and 4.01 (two s, 2H), 3.89 and 3.88 (two s, 2H), 3.79 (m, 3H), 2.20 (m, 2H), 1.56 (m, 2H), 1.32 (m, 2H); IR (film) vmax 3272, 3067, 2933, 1646, 1554, 1513, 1456, 1246, 1174, 1031, 641, 821 cm−1; FABHRMS (NBA-CsI) m/z 584.1535 (M+Cs+, C26H33N3O4 requires 584.1535).

N-(8-Nonenylcarbonyl)-N'-benzyl-N"-(4-methoxybenzyl)iminodiacetic Acid Diamide (A1B1C3): 1H NMR (CDCl3, 500 MHz) d 9.65 (m, 1H, NH), 7.25 (m, 7H), 6.84 (m, 2H), 6.32 (two s, 1H, NH), 5.80 (m, 1H), 4.94 (m, 2H), 4.43 (m, 4H), 4.03 (m, 2H), 3.89 (m, 2H), 3.79 (m, 3H), 2.21 (m, 2H), 2.04 (m, 2H), 1.55 (m, 2H), 1.36 (m, 2H), 1.21 (m, 6H); IR (film) vmax 3272, 3067, 2923, 2851, 1656, 1636, 1564, 1549, 1513, 1462, 1246, 1174, 1031 cm−1; FABHRMS (NBA-CsI) m/z 626.2006 (M+Cs+, C29H39N3O4 requires 626.1995).

N-(9-Decenylcarbonyl)-N'-benzyl-N"-(4-methoxybenzyl)iminodiacetic Acid Diamide (A1B1C4): 1H NMR (CDCl3, 500 MHz) d 9.50 (m, 1H), 7.27 (m, 7H), 6.83 (m, 2H), 6.50 (two s, 1H), 5.81 (m, 1H), 4.96 (m, 2H), 4.43 (m, 4H), 4.01 (apparent d, 2H), 3.88 (broad s, 2H), 3.77 (m, 3H), 2.18 (m, 2H), 2.03 (m, 2H), 1.52 (m, 2H), 1.25 (m, 2H), 1.25 and 1.22 (two s, 8H); IR (film) vmax 3262, 3077, 2923, 2851, 1656, 1641, 1564, 1549, 1513, 1462, 1246, 1174, 1031 cm−1; FABHRMS (NBA-CsI) m/z 640.2165 (M+Cs+, C30H41N3O4 requires 640.2151).

General Procedure for the Third Diversification of Library 1: Preparation of A2B2C1-4 as illustrated in FIG. 24. A stock solution was prepared by diluting a mixture of 2.5 mmol of each w-alkene carboxylic acid (C1–C4) and 45 mmol of i-Pr2NEt to 100 mL in anhydrous DMF. A 4.97 mL sample of this stock solution (0.497 mmol of CX) was added to A2B2.HCl (0.746 mmol). After the addition of PyBrOP (348 mg, 0.746 mmol), the mixture was stirred for 16 h at 25° C. Work-up as described provided 102 mg (41%) of the title mixture as a light yellow oil. The 1H NMR spectrum showed the vinyl protons (CH=CH2) as two multiplets at d 5.70 and 4.96, respectively. The MS exhibited all the expected molecular ions: ESMS (M+H+) m/z 536, 522, 480, 466.

General Procedure for the Synthesis of Individual Homodimer Sublibrary Entries in Library 1 as illustrated in FIG. 24: Preparation of A1B1C1–A1B1C1. A solution of A1B1C1 (22 mg, 0.050 mmol) and RuCl2(PCy3) 2=CHPh (10 mg, 0.12 mmol) in CHCl3 (2 mL) was warmed at reflux for 16 h. The solvent was removed in vacuo and chromatography (SiO2, 1.5 ¥ 20 cm, 50–100% EtOAc-hexane and 5% CH3OH-EtOAc) afforded 14 mg (66%) of A1B1C1–A1B1C1 as a yellow oil: 1H NMR (CDCl3, 500 MHz) d 9.47 (broad s, 2H, NH), 7.23 (m, 16H, fourteen aromatic and two NH), 6.81 (m, 4H), 5.20 (two br s, 2H), 4.40 (m, 8H), 3.77 (m, 14H), 2.18 (m, 4H), 1.90 (m, 4H), 1.52 (m, 4H); IR (film) vmax 3272, 3067, 2933, 2851, 1651, 1559, 1513, 1456, 1400, 1400, 1303, 1246, 1174, 1026, 1026, 959, 821, 739, 697 cm−1; FABHRMS (NBA-CsI) m/z 979.3337 (M+Cs+, C48H58N6O8 requires 979.3370).

A1B1C2-A1B1C2: 1H NMR (CDCl3, 500 MHz) d 9.60 (m, 2H), 7.26 (m, 16H, fourteen aromatic and two NH), 6.81 (m, 4H), 5.28 (br s, 2H), 4.40 (m, 8H), 3.77 (m, 14H), 2.17 (br s, 4H), 1.94 (br s, 4H), 1.50 (br s, 4H), 1.27 (m, 4H); the trans:cis ratio was established by 1H NMR integration (600 MHz, C6D6) d 5.37 and 5.42 (3.2:1); IR (film) vmax 3272, 3067, 2933, 2851, 1652, 1558, 1514, 1456, 1431, 1303, 1249, 1203, 1180, 1133, 1026, 964, 805, 697 cm−1; FABHRMS (NBA-CsI) m/z 1007.3638 (M+Cs+, C50H62N6O8 requires 1007.3683).

A1B1C3-A1B1C3: 1H NMR (CDCl3, 500 MHz) d 9.65 (m, 2H, NH), 7.27 (m, 14H), 6.82 (m, 4H), 6.60 (m, 2H, NH), 5.37 (m, 2H), 4.40 (m, 8H), 4.00 (m, 4H), 3.86 (br s, 4H), 3.78 and 3.77 (two s, 6H), 2.19 (m, 4H), 1.60 (m, 4H), 1.53 (m, 4H), 1.32 (m, 4H), 1.22 (m, 12H); IR (film) vmax 3262, 3056, 2923, 2851, 1662, 1651, 1564, 1513, 1451, 1246, 1174, 1144, 1113, 1026, 959, 892, 856, 821 cm−1; FABHRMS (NBA-CsI) m/z 1091.4671 (M+Cs+, C56H74N6O8 requires 1091.4622).

A1B1C4-A1B1C4: 1H NMR (CDCl3, 500 MHz) d 9.60 (m, 2H, NH), 7.26 (m, 14H), 6.82 (m, 4H), 6.60 (m, 2H, NH), 5.38 (m, 2H), 4.40 (m, 8H), 4.00 (m, 4H), 3.86 (br s, 4H), 3.78 and 3.77 (two s, 6H), 2.19 (m, 4H), 1.97 (m, 4H), 1.52 (m, 4H), 1.32 (m, 4H), 1.22 (m, 16H); IR (film) vmax 3272, 3067, 2923, 1646, 1559, 1513, 1451, 1246, 1174, 1031 cm−1; FABHRMS (NBA-CsI) m/z 1119.4985 (M+Cs+, C58H78N6O8 requires 1119.4985).

General Procedure for the Synthesis of a Homodimer Sublibrary for Library 1 as illustrated in FIG. 24. A solution of A1B1C1–4 (39 mg, 0.082 mmol) and RuCl2(PCy3) 2=CHPh (17 mg, 0.021 mmol) in CHCl3 (2 mL) was warmed at reflux for 16 h. The solvent was removed in vacuo and chromatography (SiO2, 1.5 ¥ 20 cm, 50–100% EtOAc-hexane and 5% CH3OH-EtOAc) afforded 26 mg (67%) of the homodimer sub-library as a yellow oil. The 1H NMR spectrum exhibited the olefinic protons (CH=CH) as a multiplet at d 5.35. The MS exhibited all the molecular ions (10 different components with 9 different molecular weights): ESMS (M+H+) m/z 987, 973, 959, 931, 917, 903, 875, 861, 847.

General Procedure for the Synthesis of a Homodimer/Heterodimer Sublibrary for Library 1 as illustrated in FIG. 24. A solution of A3B3C1–4 (11 mg, 0.020 mmol), A4B4C1–4 (12 mg, 0.020 mmol), and RuCl2(PCy3) 2=CHPh (8.2 mg, 0.01 mmol) in CHCl3 (2 mL) was warmed at reflux for 16 h. The solvent was evaporated and chromatography (SiO2, 1.5 to 20 cm, 50–100% EtOAc-hexane and 5–15% CH3OH-EtOAc) afforded 14 mg (62%) of the sub-library as a yellow oil. The 1H NMR spectrum showed the olefinic protons (CH=CH) as a multiplet at d 5.35. The MS exhibited all the expected molecular ions (36 different components which have 17 different molecular weights): ESMS (M+H+) m/z 1248, 1234, 1220, 1206, 1192, 1178, 1164, 1150, 1136, 1122, 1108, 1094, 1080, 1066, 1052, 1038, 1024.

General Procedure for Preparation of 700 (Library 2) as illustrated in FIG. 24: N,N'-Bis(N-(2-(3,4-dimethoxyphenyl)ethyl) carboxamidomethyl)-N,N'-bis(N-(2-(4-fluorophenyl)ethyl)carboxamidomethyl)-N"-((tert-butyloxy)carbonyl)iminodiacetic Acid Diamide (Library 2, 700: A1B9). The Boc derivative 3 (A1B9 1.29 g, 2.50 mmol) was stirred in a solution of 4 M HCl-dioxane (13 mL) at 25° C. for 4 h. Removal of the solvent under N2 and in vacuo gave the deprotected material as a pale yellowish solid, which was dissolved in anhydrous DMF (10 mL). N-BOC-Iminodiacetic acid (194 mg, 0.83 mmol), i-Pr2NEt (1.30 mL, 7.49 mmol) and PyBrOP (1.16 g, 2.50 mmol) were added sequentially. The reaction mixture was stirred for 16 h at 25° C. before being diluted with EtOAc (100 mL) and washed with 10% aqueous HCl (2 to 100 mL), saturated aqueous NaHCO3 (2 to 100 mL), saturated aqueous NaCl (100 mL), and dried (Na2SO4). The solvent was removed under reduced pressure to provide 859 mg (100%) of the title substance in oil: 1H NMR (CDCl3, 500 MHz) d 8.90–7.70 (m, 4H, NH), 7.09 (apparent br s, 4H), 6.90 (apparent br s, 4H), 6.71 (apparent br s, 6H), 4.01 (m, 8H), 3.77 (apparent br s, i6 H), 3.40 (m, 8H), 2.74 (m, 8H), 1.35 (apparent br s, 9H); IR (film) vmax 3276, 3074, 2939, 1661, 1565, 1509, 1464, 1414, 1369, 1333, 1256, 1236, 1154, 1026, 831, 759 cm−1; FABHRMS (NBA-CsI) m/z 1164.3933 (M+Cs+, C53H67N7O12 F2 requires 1164.3870).

N,N'-Bis(N-(2-(3-methoxyphenyl)ethyl) carboxamidomethyl)N,N'-bis(N-(2-(4-methoxyphenyl)ethyl)carboxamidomethyl)-N"-((tert-butyloxy)carbonyl) iminodiacetic Acid Diamide (7: A2B2): 1H NMR (CDCl3, 500 MHz) d 8.90–7.30 (m, 4H, NH), 7.07 (m, 6H), 6.78 (m, 10H), 4.02 (m, 8H), 3.74 (m, 16H), 3.45 (m, 8H), 2.76 (m, 8H), 1.41 (m, 9H); IR (film) vmax 3272, 3076, 2933, 2831, 1662, 1610, 1585, 1513, 1462, 1405, 1364, 1303, 1246, 1164, 1036, 964, 903, 841, 780, 739, 697 cm−1; FABHRMS (NBA-CsI) m/z 1128.4125 (M+Cs+, C53H69N7O12 requires 1128.4059).

N,N'-Tetra(N-(2-(N-a-CBZ-L-lysine Methyl Ester) carboxamidomethyl)-N"-((tert-butyloxy)carbonyl) iminodiacetic Acid Diamide (7: A3B11): 1H NMR (CDCl3, 500 MHz) d 7.31 (m, 20 H), 5.80 (m, 4H), 5.07 (d, 8H), 4.28 (m, 4H), 4.10 (m, 24H), 3.20 (m, 8H), 1.70 (m, 8H), 1.40 (m, 25H); IR (film) vmax 3301, 3077, 2944, 2862, 1713, 1656, 1539, 1456, 1436, 1344, 1256, 1215, 1169, 1051, 1031, 913, 846, 780, 739, 697 cm−1; FABHRMS (NBA-NaI) m/z 1590.7336 (M+Na+, C77H105N11O24 requires 1590.7232).

General Procedure for the Preparation of 800 (Library 2): A1B13C1–4 as illustrated in FIG. 24. A stock solution was prepared through diluting a mixture of 2.5 mmol of each w-alkene carboxylic acid (C1–C4) and 45 mmol of i-Pr2NEt to 100 mL of anhydrous DMF. A 0.591 mL sample of this stock solution (0.0591 mmol of CX) was added to A1B13.HCl (0.887 mmol) followed by PyBrOP (41.3 mg, 0.887 mmol) and the mixture was stirred at 25° C. for 16 h. Work-up as described above provided 50 mg (88%) of the title substance as a light yellow oil. The 1H NMR spectrum shows the vinyl protons (CH=CH2) as two multiplets at d 5.70 and 4.96, respectively. The MS exhibited all the expected molecular ions: ESMS (M+Na+) m/z 1027, 998, 956, 928.

A1B4C1-4: The 1H NMR spectrum shows the vinyl protons (CH=CH2) as two multiplets at d 5.70 and 4.96, respectively. The MS exhibited all the expected molecular ions: ESMS (M+Na+) m/z 1159, 1131, 1089, 1061.

A3B14C1–4: The 1H NMR spectrum shows the vinyl protons (CH=CH2) as two multiplets at d 5.70 and 4.96, respectively. The MS spectrum exhibited all the expected molecular ions: ESMS (M+Na+) m/z 1369, 1341, 1299, 1271.

General Procedure for the Synthesis of a Homodimer Sublibrary for Library 2 (Tetramers) as illustrated in FIG. 24 900/1000. A solution of A1B13C1–4 (36 mg, 0.038 mmol), and RuCl2(PCy3) 2=CHPh (6.2 mg, 0.0075 mmol) in CHCl3 (3 mL) was warmed at reflux for 16 h. The solvent was evaporated and chromatography (SiO2, 1.5 ¥ 20 cm, 50–100% EtOAc-hexanes and 5–25% CH3OH-EtOAc) afforded 24 mg (68%) of the sublibrary as a yellow oil. The 1H NMR spectrum shows the olefinic protons (CH=CH) as a broad singlet at d 5.30. The MS exhibited all the expected molecular ions (10 different components which have 9 different molecular weights): ESMS (M+Na+) m/z 2003, 1975, 1947, 1933, 1905, 1877, 1863, 1834, 1806).

What is claimed is:

1. A convergent process for synthesizing a dimerized combined library, the process comprising the following steps:

Step A: Constructing a first combinational library of N-BOC iminodiacetic acid diamides by reacting N-BOC-iminodiacetic acid anhydride with six or more primary or secondary amine reagents; the carboxylic acid is then reacted with six or more primary or secondary amine reagents in the presence of a reagent suitable for amide bond formation to give N-BOC iminodiacetic acid diamides; and then Step B: Constructing a second combinatorial library of N-BOC iminodiacetic acid diamides by reacting N-BOC-iminodiacetic acid anhydride with six or more primary or secondary amine reagents; the carboxylic acid is then reacted with six or more primary or secondary amine reagents in the presence of a reagent suitable for amide bond formation to give N-BOC iminodiacetic acid diamides; and then Step C: Joining the first combinatorial library with the second combinatorial library by forming amide bonds with both the deprotected iminodiacetic acid diamides of said Step A and the deprotected iminodiacetic acid diamides of said Step B with a cyclohexyl dicarboxylic acid for constructing the dimerized combinatorial library.

2. A dimerized combinatorial library constructed by the following convergent process:

Step A: Constructing a first combinatorial library of N-BOC iminodiacetic acid diamides by reacting N-BOC-iminodiacetic acid anhydride with six or more primary or secondary amine reagents; the carboxylic acid is then reacted with six or more primary or secondary amine reagents in the presence of a reagent suitable for amide bond formation to give N-BOC iminodiacetic acid diamides; and then Step B: Constructing a second combinatorial library of N-BOC iminodiacetic acid diamides by reacting N-BOC-iminodiacetic acid anhydride with six or more primary or secondary amine reagents; the carboxylic acid is then reacted with six or more primary or secondary amine reagents in the presence of a reagent suitable for amide bond formation to give N-BOC iminodiacetic acid diamides; and then Step C: Joining the first combinatorial library with the second combinatorial library by forming amide bonds with both the deprotected iminodiacetic acid diamides of said Step A and the deprotected iminodiacetic acid diamides of said Step B with a cyclohexyl dicarboxylic acid for constructing the dimerized combinatorial library.

* * * * *